US006096545A

United States Patent [19]
Lefebvre et al.

[11] Patent Number: 6,096,545
[45] Date of Patent: Aug. 1, 2000

[54] PHOSPHATE STARVATION-INDUCIBLE PROTEINS

[75] Inventors: Daniel D. Lefebvre; Mohammed A. Malboobi, both of Kingston, Canada

[73] Assignee: Queen's University at Kingston, Kingston, Canada

[21] Appl. No.: 08/688,988

[22] Filed: Jul. 31, 1996

[51] Int. Cl.$^7$ .............................. C12N 1/20; C07H 21/04
[52] U.S. Cl. ................. 435/410; 435/252.33; 435/320.1; 435/194; 536/23.2; 536/23.1; 536/23.6
[58] Field of Search .................................. 435/194, 252.3, 435/252.33, 419, 320.1, 410; 536/23.1, 23.2, 23.6

[56] References Cited

U.S. PATENT DOCUMENTS

| | | | |
|---|---|---|---|
| 5,098,838 | 3/1992 | Goodman et al. | 435/183 |
| 5,188,958 | 2/1993 | Moloney et al. | 435/240.4 |
| 5,268,288 | 12/1993 | Pharr et al. | 435/190 |
| 5,401,836 | 3/1995 | Baszczynski et al. | 536/24.1 |
| 5,413,920 | 5/1995 | Wanner et al. | 435/71.2 |

FOREIGN PATENT DOCUMENTS

| | | |
|---|---|---|
| 2071473 | 12/1992 | Canada . |
| WO 95/05731 | 3/1995 | WIPO . |
| 9804701 | 5/1998 | WIPO . |

OTHER PUBLICATIONS

U.S. provisional 60/022,391, Jul. 29, 1996, Raghothama, et al.

Bariola et al. "The arabidopsis ribonuclease gene RNS1 is tightly controlled in response to phosphate limitation" The Plant Journal 6(5), 673–685, 1994.

Cock et al. "cDNA structure and regulatory properties of a family of starvation–induced ribonuclease from tomato" Plant Mol. Biol. 27, 477–485, Feb. 1995.

Budicky et al. "Identification of a putative phosphate starvation inducible protein kinase from *Brassica nigra*" Plant Physiol. 102(1), Supp. S, pp. 68, abstract No. 371, May 1993.

Bariola et al. "The arabidopsis ribonuclease gene RNS1 is tightly controlled in response to phosphate limitation" The Plant Journal 6(5), 673–685, 1994.

Cock et al. "cDNA structure and regulatory properties of a family of starvation–induced ribonuclease from tomato" Plant Mol. Biol. 27, 477–485, Feb. 1995.

Budicky et al. "Identification of a putative phosphate starvation inducible protein kinase from *Brassica nigra*" Plant Physiol. 102(1), Supp. S, pp. 68, abstract No. 371, May 1993.

B.L. EPEL. et al., Database EMBL Nucleotide Sequence, Hinxton, GB, "A41kDa protein isolated from maize mesocotyl cell walls immunolocalizes to plamodesmata" *Protoplasma*, 191:70–78 (1996).

Database WP1, Week 9745, Derwent Publications Ltd., London, GB, WO 97 35984 A (Mitsui Plant Biotechnology Res Inst) 27–31 and 72–74.

Database EMBL Nucleotide Sequence, Hinxton, GB, "Inorganic phosphate transporters from higher plants" *Plant Cell* 9:381–392 (1997).

N. Mitsukawa, et al. "Overexpression of an *Arabidopsis thaliana* high–affinity affinity phosphate transproter gene in tobacco cultured cells enhances cell growth under phosphate–limited conditions" Proceedings of the National Academy of Sciences, 94:70998–7102 (1997).

U.S. Muchal, et al. "Phosphate transporters from the higher plant *Arabidopsis thaliana*", Proceedings from the National Academy of Sciences 93(*19*):1051199–10523 (1996).

T. Newman, et al. "Genes galore: a summary of methods for accessing results from large–scale partial sequencing of anymous Arabidopsis cDNA clones", *Plant Physiology* 106:1241–1255 (1994).

Malboobi, M.A. and Lefebvre, D.D. "Idifferential gene expression at the transcriptional level in response to phosphate starvation in *Brassica–nigra* suspension cells", *Plant Physiology*, 102(1)(suppl):9 (1993).

Park, Y.S., et al. "Frequent in–frame length variations are found in the diverged simple repeat sequences of the protein–coding regions of two putative protein kinase genes of *Brassica napus*", *Plant Molecular Biology*, 27:829–833 (1995).

Malboobi, M.A., et al. "Identification and nucleotide sequences of cDNA clones of phosphate inducible beta–glucosidase genes of Brassicaceae (Accession Nos. U72153 and U72154) (PGR96–114)", *Plant Physiology*, 112(26):1399 (1996).

Malboobi, M.A. and Lefebvre, D.D. "A phosphate–starvation inducible beta–glucosidase gene (psr3.2) isolated from *Arabidopsis thaliana* is a member of a distinct subfamily of the BGA family" *Plant Molecular Biology*, 34(1):57–68.

Taylor, Crispin B., et al. "RNS1: A senescence–associated RNase of Arabidopsis that diverged from the S–RNases before speciation" *Proc. Natl. Acad. Sci. USA* 90:5118–5122 (1993).

Löffler, Andreas, et al. "Amino acid sequence of an intracellular, phosphate–starvation–induced ribonuclease from cultured tomato (*Lycopersicon esculentum* ) cells" *Eur. J. Biochem.* 214(*3*):627–633 (1993).

Jost, Wolfgang, et al. "Amino acid sequence of an extracellular, phosphate–starvation–induced ribonuclease from cultured tomato (*Lycopersicon esculentum*) cells" *Eur. J. Biochem.* 198(*1*):1–6 (1991).

(List continued on next page.)

*Primary Examiner*—Ponnathapu Achutamurthy
*Assistant Examiner*—Nashaat T. Nashed
*Attorney, Agent, or Firm*—Hamilton, Brook, Smith & Reynolds, P.C.

[57] ABSTRACT

This invention provides proteins, especially protein kinases and glucosidases, which are expressed under conditions of phosphate deprivation. Further provided are nucleic acids and nucleic acid constructs encoding these proteins, cells containing the nucleic acids described and transgenic photosynthetic organisms with altered phosphate-inducible enzyme activity.

25 Claims, 28 Drawing Sheets

OTHER PUBLICATIONS

Dodds, Peter N., et al. "Molecular characterisation of an S–like RNase of *Nicotiana alata* that is induced by phosphate starvation" *Plant Molecular Biology* 31:227–238 (1996).

Glund, K., and Goldstein, A.H., "Regulation, synthesis, and excretion of a phosphate starvation inducible RNase by plant cells", In Verma (ed.), *Control of Plant Gene Expression*, CRC Press, Boca Raton, FL, pp. 311–323 (1993).

Malboobi, M.A., and Lefebvre, D.D., "Isolation of cDNA clones of genes with altered expression levels in phosphate–starved *Brassica nigra* suspension cells", *Plant Mol. Biol.* 28: 859–870 (1995).

Park, Y.S. et al., "Two putative protein kinases from *Arabidopsis thaliana* contain highly acidic domains", *Plant Mol. Biol.* 22: 615–624 (1993).

Poirier, Y., Thoma, S., Somerville, C., and Schiefelbein, J., "A mutant of Arabidopsis deficient in xylem loading of phosphate", *Plant Physiol.* 97: 1097–1093 (1991).

Rao, I.M., Fredeen, A.L., and Terry, N., "Leaf phosphate status, photosynthesis, and carbon partitioning in sugar beet. Diurnal changes in carbon partitioning and carbon export" *Plant Physiol.* 92: 29–36 (1990).

Dumont, F., Joris, B., Gumusboga, A., Bruyninx, M., and Loppes, R., "Isolation and characterization of cDNA sequences controlled by inorganic phosphate in *Chlamydomonas reinhardtii*", *Plant Science* 89, 55–67 (1993).

Ezaki, B., Yamamoto, Y., and Matsumoto, H., "Cloning and sequencing of the cDNAs induced by aluminum treatment and $P_i$ starvation in cultured tobacco cells", *Physiologia Plantarum* 93, 11–18 (1995).

Falk, A., and Rask, L., "Expression of a zeatin–O–glucoside–degrading β–glucosidase in *Brassica napus*", *Plant Physiol.* 108, 1369–1377 (1995).

Liu, C., and Raghothama, K.G., "Cloning and characterization of pTPS11, a cDNA (Accession No. U34808) for a phosphate–starvation induced gene from tomato (PGR95–093)", *Plant Physiol.* 109: 1126 (1995).

Oxtoby, E., Dunn, M. A., Pancoro, A., and Hughes, M. A., "Nucleotide and derived amino acid sequence of the cyanogenic β–glucosidase (linamarase) from white clover (*Trifolium repen* L.)", *Plant Mol. Biol.* 17: 209–219 (1991).

Zhang, R., and Walker, J.C., "Structure and expression of the S locus–related genes of amize", *Plant Mol. Biol.* 21:1171–1174 (1993).

Gräbnitz, F. et al., "Structure of the β–glucosidase gene bglA of *Clostridium thermocellum*", *Eur. J. Biochem.*, 200, 301–309 (1991).

Hughes, M.A. et al., "A molecular and biochemical analysis of the structure of the cyanogenic β–glucosidase (Linamarase) from Cassava (*Manihot esculenta* Cranz)", *Arch. Biochem. Biophys.* 295:273–279 (1992).

Jenkins, J. et al., "β–Glucosidase, β–galactosidase, family A cellulases, family F xylanases and two barley glycanases form a superfamily of enzymes with 8–fold β/α architecture and with two conserved glutamates near the carboxy–terminal ends of β–strands four and seven", *FEBS Lett.* 362:281–285 (1995).

Leah, R., et al., "Biochemical and molecular characterization of a barley seed β–glucosidase", *J. Biol. Chem.*, 270: 15789–15797 (1995).

Pelham, H.R.B., "Control of protein exit from the endoplasmic reticulum", *Annu. Rev. Cell Biol.* 5:1–23 (1989).

Andeberg, R.J., and Walker–Simmons, M.K., "Isolation of a wheat cDNA clone for an abscisic acid–inducible transcript with homology to protein kinases", *Proc. Natl. Acad. Sci. USA* 89:10183–10187 (1992).

Aoyagi, K. et al., "The pea rbcS–3A enhancer–like element directs cell–specific expression in transgenic tobacco", *Mol. Gen. Genet.* 213:179–185 (1988).

Ashihara, H., Li, X.–N., and Ukaji, T., "Effect of inorganic phosphate on the biosynthesis of purine and pyrimidine nucleotides in suspension–cultured cells of *Catharanthus roseus*", *Ann. Bot.* 61: 225–232 (1988).

Ballou, L.M., and Fisher, E.H., "Phosphoprotein phosphatases", In Boyer et al. (eds.), *The Enzymes*, vol. 17, pp. 311–361, Academic Press, NY (1986).

Bieleski, R.L., "Phosphate pools, phosphate transport, and phosphate availability", *Ann. Rev. Plant. Physiol.* 24: 225–252 (1973).

Brisson, N. et al., "Expression of a bacterial gene in plants by using a viral vector", *Nature* 310:511–514 (1984).

Broglie, R. et al., "Light–regulated expression of a pea ribolose–1,5–bisphosphate carboxylase small subunit gene in transformed plant cells", *Science*, 224:838–843 (1984).

Chappell, J., and Hahlbrock, K., "Transcription of plant defence genes in response to UV light or fungal elicitation", *Nature* 311: 76–78 (1984).

Chirgwin, J.M., Przybyla, A.E., MacDonald, R.J., and Rutter, W.J., "Isolation of biologically active ribonucleic acid from sources enriched in ribonuclease", *Biochemistry* 18: 5294–5299 (1979).

Cordes, S. et al., "Interaction of a developmentally regulated DNA–binding factor with sites flanking two different fruit–ripening genes from tomato", *Plant Cell* 1:1025–1034 (1989).

Coruzzi, G. et al., "Tissue–specific and light–regulated expression of a pea nuclear gene oncoding the small subunit or ribulose–1,5–bisphosphate carboxylase", *EMBO J.* 3:1671–1679 (1984).

de Feyter, R., Young, M., Schroeder, K., Dennis, E.S., and Gerlach, W., "A ribozyme gene and an antisense gene are equally effective in conferring resistance to tobacco mosaic virus on transgenic tobacco", *Mol. Gen. Genet.* 250: 329–338 (1996).

de Pater, S. et al., "A 22–bp fragment of the pea lectin promoter containing essential TGAC–like motifs confers seed–specific gene expression", *Plant Cell* 5:877–866 (1993).

Delhaize, E., and Randall, P.J., "Characterization of a phosphate–accumulator mutant of *Arabidopsis thaliana*", *Plant Physiol.* 107: 207–213 (1995).

Duff, S.M.G., Lefebvre, D.D., and Plaxton, W.C., "Purification and characterization of a phosphoenolpyruvate phosphatase from *Brassica nigra* suspension cells", *Plant Physiol.* 90: 734–741 (1989).

Duff, S.M.G., Moorhead, G.B.G., Lefebvre, D.D., and Plaxton, W.C., "Phosphate starvation inducible 'bypasses' of adenylate and phosphate dependent glycolytic enzymes in *Brassica nigra* suspension cells", *Plant Physiol.* 90: 1275–1278 (1989).

Duff, S.M.G., Plaxton, W.C., and Lefebvre, D.D., "Phosphate–starvation response in plant cells: de novo synthesis and degradation of acid phosphatases", *Proc. Natl. Acad. Sci. USA* 88: 9538–9542 (1991).

Duff, S.M.G., Sarath, G., and Plaxton, W.C., "The role of acid phosphatases in plant phosphorus metabolism", *Physiol. Plant.* 90: 791–800 (1994).

Edwards, J.W. et al., "Cell–specific expression in transgenic plants reveals nonoverlapping roles for chloroplast and cytosolic glutamine synthetase", *Proc. Natl. Acad. Sci. USA*, 87:3459–3463 (1990).

Fife, C.A., Newcomb, W., and Lefebvre, D.D., "The effect of phosphate deprivation on protein synthesis and fixed carbon storage reserves in *Brassica nigra* suspension cells", *Can. J. Bot.* 68: 1840–1847 (1990).

Freeling, M. et al., "Maize Adh1" *Ann. Rev. Genetics*, 19:297–323 (1985).

Frisch, D.A. et al., "Chromosomal integration is required for spatial regulation of expression from the β–phaseolin promoter", *Plant J.* 7:503–512 (1995).

Gellatly, K.S., Moorhead, G.B.G., Duff, S.M.G., Lefebvre, D.D., and Plaxton,W.C., "Purification and characterization of a potato tuber acid phosphatase having significant phosphotyrosine phosphatase activity", *Plant Physiol.* 106: 223–232 (1994).

Gish, W., and States, D.J., "Identification of protein coding regions by database similarity search", *Nature Genet.* 3: 266–272 (1993).

Gogarten, J.P., Fichmann, J., Braun, Y., Morgan, L., Styles, P., Taiz, S.L., DeLapp, K., and Taiz, L., "The use of antisense mRNA to inhibit the tonoplast H+ATPase in carrot", *Plant Cell* 4: 851–864 (1992).

Goldstein, A.H., Mayfield, S.P., Danon, A., and Tibbot, B.K., "Phosphate starvation inducible metabolism in *Lycopersicon esculentum*. III. Changes in protein secretion under nutrient stress", *Plant Physiol.* 91: 175–182 (1989).

Goldstein, A.H., "Phosphate starvation inducible enzymes and proteins in higher plants", In Wray (ed.), *Inducible Plant Proteins*, Cambridge University Press, pp. 25–44 (1992).

Gurley, W.B. et al., "Upstream sequences required for efficient expression of a soybean heat shock gene", *Mol. Cell. Biol.* 6:559–565 (1986).

Hattori, T. et al., "Regulation of the Osem gene by abscisic acid and the transcriptional activator VP1: analysis of cis––acting promoter elements required for regulation by abscisic acid", *Plant J.* 7:913–925 (1995).

Hawkesford, M.J., and Belcher, A.R., "Differential protein synthesis in response to sulphate and phosphate deprivation: identification of possible components of plasma–membrane transport systems in cultured tomato roots", *Planta* 185: 323–329 (1991).

Heinrich, J.–C., Tabler, M., and Lois, C., "Influence of chromosomal position and copy number of a white–directed ribozyme gene on the suppression of eye pigmentation in *Drosophila melanogaster*", *Antisense Res. Dev.* 5: 155–160 (1995).

Hoefnagel, M.H.N., van Iren, F., and Libbenga, K.R., "In suspension culture of *Catharanthus roseus* the cyanide–resistant pathway is engaged in respiration by excess sugar in combination with phosphate or nitrogen starvation", *Physiol. Plant.* 87: 297–304 (1993).

Katavic, V. et al., "In planta transformation of *Arabidopsis thaliana*", *Mol. Gen. Genet.* 245:363–370 (1994).

Kieber, J.J. et al., "CTR1, a negative regulator of the ethylene response pathway in Arabidopsis, encodes a member of the Raf family of protein kinases", *Cell* 72:427–441 (1993).

Konat, G., Laszkiewicz, I., Bednarczuk, T., Kanoh, M., and Wiggins, R.C., "Generation of radioactive and nonradioactive ssDNA hybridization probes by polymerase chain reaction" *Technique* 3: 64–68 (1991).

Kosugi, S. et al., "Two of three promoter elements identified in a rice gene for proliferating cell nuclear antigen are essential for meristematic tissue,specific expression", *Plant J.* 7: 877–886 (1995).

Lee, R.B., Ratcliffe, R.G., and Southon, T.E., "$^{31}$P NMR measurements of the cytoplasmic and vacuolar $P_i$ content of mature maize roots: relationships with phosphorus status and phosphate fluxes", *J. Exp. Bot.* 41: 1063–1078 (1990).

Lefebvre, D.D. and Glass, A.D.M., "Regulation of phosphate influx in barley roots: Effects of phosphate deprivation and reduction of influx with provision of orthophosphate", *Physiol. Plant.* 54: 199–206 (1982).

Lefebvre, D.D., Duff, S.M.G., Fife, C.A., Julien–Inalsingh, C., and Plaxton, W.C., "Response to phosphate deprivation in *Brassica nigra* suspension cells. Enhancement of intracellular, cell surface, and secreted phosphatase activities compared to increases in $P_i$–absorption rate", *Plant Physiol.* 93: 504–511 (1990).

Löfler, A., Abel, S., Jost, W., Beintema, J.J., and Glund, K., "Phosphate–regulated induction of intracellular ribonucleases in cultured tomato (*Lycopersicon esculentum*) cells", *Plant Physiol.* 98: 1472–1478 (1992).

Manser, E. et al., "A brain serine/threonine protein kinase activated by Cdc42 and Rac1", *Nature* 367:40–46 (1994).

Manser, E. et al., "Diversity and versatility of GTPase activating proteins for the p21rho subfamily of ras G proteins detected by a novel overlay assay", *J. Biol. Chem.* 267:16025–16028 (1992).

Manser, E. et al., "Purification and assay of kinases that interact with Rac/Cdc42", *Methods in Enzymol.* 256:215–227, (1995).

Marcotte, Jr., W.R. et al., "Abscisic acid–responsive sequences from the Em gene of wheat", *Plant Cell* 1:969–976 (1989).

Martin, T. et al., "Expression of an Arabidopsis sucrose synthase gene indicates a role in metabolization of sucrose both during phloem loading and in sink organs", *Plant J.* 4:367–377 (1993).

Meyer, P., and Saedler, H., "Homology–dependent gene silencing in plants", *Annu. Rev. Plant Physiol. Plant Mol. Biol.* 47:23–48 (1996).

Mimura, T., Dietz, K.–J., Kaiser, W., Schramm, M.J., Kaiser, G., and Heber, U., "Phosphate transport across biomembranes and cytosolic phosphate homeostasis in barely leaves", *Planta* 180: 136–146 (1990).

Muller–Rober, B. et al., "A truncated version of an ADP–glucose pyrophosphorylase promoter from potato specifies guard cell–selective expression in transgenic plants", *Plant Cell* 6:601–612 (1994).

Murashige, T., and Skoog, F., "A revised medium for rapid growth and bio assays with tobacco tissue cultures", *Physiol. Plant* 15:473–497 (1962).

Nagano, M., and Ashihara, H., "Long–term phosphate starvation and respiratory metabolism in suspension–cultured *Catharanthus roseus* cells", *Plant Cell Physiol.* 34: 1219–1228 (1993).

Nagao, R.T. et al., "The heat shock response: a comparative analysis", *Oxford Surveys of Plant Molecular and Cell Biology*, Miflin, B.J., Ed., 3:384–438, Oxford University Press, Oxford (1986).

Nürnberger, T., Abel, S., Jost, W., and Glund, K., "Induction of an extracellular ribonuclease in cultured tomato cells upon phosphate starvation", *Plant Physiol.* 92: 970–976 (1990).

Rebeille, F., Bligny, R., Martin, J.-B., and Douce, R., "Relationship between the cytoplasm and the vacuole phosphate pool in *Acer pseudoplatanus* cells", *Arch. Biochem. Biophys.* 225: 143–148 (1983).

Rodrigues–Pousada, R.A. et al., "The Arabidopsis 1–aminocyclopropane–1–carboxylate synthase gene 1 is expressed during early development", *Plant Cell* 5:897–911 (1993).

Rychter, A.M., and Mikulska, M., "The relationship between phosphate status and cyanide–resistant respiration in bean roots", *Physiol. Plant* 79: 663–667 (1990).

Rychter, A.M., Chauveau, M., Bomsel, J.–L., and Lance, C., "The effect of phosphate deficiency on mitochondrial activity and adenylate levels in bear roots", *Physiol. Plant.* 84: 80–86 (1992).

Sachay, J.E., Wallace, R.L., and Johns, M.A., "Phosphate stress response in hydroponically grown maize", *Plant & Soil* 132: 85–90 (1991).

Sadka, A., DeWald, D.B., May, G.D., Park, W.D., and Mullet, J.E., "Phosphate modulates transcription of soybear VspB and other sugar–inducible genes", *Plant Cell* 6: 737–739 (1994).

Saleki, R. et al., "Mutants of *Arabidopsis thaliana* capable of germination under saline conditions", *Plant Physiol.* 101:839–845 (1993).

Salisbury, F.B., and Ross, C.W., "Mineral Nutrition", in *Plant Physiology* (3rd ed.), Wadsworth, Belmont, CA, pp. 96–113 (1985).

Shotkoski, F.A., and Fallon, A.M., "Expression of an antisense dihydrofolate reductase transcript in transfected mosquito cells: effects on growth and plating efficiency", *Am. J. Trop. Med. Hyg.* 50: 433–439 (1994).

Somssich, I.E. et al., "Differential early activation of defence–related genes in elicitor–treated parsley cells", *Plant Mol. Biol.* 12: 227–234 (1989).

Sugaya, S. et al., "Cell–specific expression of the rolC gene of the TL–DNA of Ri Plasmid in transgenic tobacco plants", *Plant Cell Physiol.*, 30:649–653 (1989).

Takamatsu, N. et al., "Expression of bacterial chloramphenical acetyltransferase gene in tobacco plants mediated by TMV–RNA", *EMBO J.* 6:307–311 (1987).

Tantikanjana, T. et al., "An alternative transcript of the S locus glycoprotein gene in a Class II pollen–recessive self–incompatibility haplotype of *Brassica oleracea* encodes a membrane–anchored protein", *Plant Cell* 5:657–666 (1993).

Theodorou, M.E., Cornel, F.A., Duff, S.M.G., and Plaxton, W.C., "Phosphate starvation–inducible synthesis of the α–subunit of the pyrophosphate–dependent phosphofructokinase in black mustard suspension cells", *J. Biol. Chem.* 267: 21901–21905 (1992).

Theodorou, M.E., and Plaxton, W.C., "Metabolic adaptations of plant respiration to nutritional phosphate deprivation", *Plant Physiol.* 101: 339–344 (1993).

Thomas, T.L., "Gene expression during plant embryogenesis and germination: an overview", *Plant Cell* 5:1401–1410 (1993).

Tu, S.–I., Cavanaugh, J.R., and Boswell, R.T., "Phosphate uptake by excised maize root tips studied by in vivo $^{31}$P nuclear magnetic resonance spectroscopy", *Plant Physiol.* 93: 778–784 (1990).

Uesono, Y. et. al., "Negative regulators of the PHO system of *Saccharomyces cerevisiae*: characterization of PHO80 and PHO85", *Mol. Gen. Genet.* 231:426–432 (1992).

Unger, E. et al., "Dominant negative mutants of Opaque2 suppress transactivation of a 22–kD Zein promoter by Opaque2 in maize endosperm cells", *Plant Cell* 5:831–841 (1993).

Usuda, H., and Shimogawara, K., "Phosphate deficiency in maize. IV. Changes in amount of sucrose phosphate synthase during the course of phosphate deprivation", *Plant Cell Physiol.* 34: 767–770 (1993).

Vorst, O. et al., "The promoter of the *Arabidopsis thaliana* plastocyanin gene contains a far upstream enhancer–like element involved in chloroplast–dependent expression", *Plant J.* 4 :933–945 (1993).

Wang, H. et. al., "Promoters from kin1 and cor6.6, two homologous *Arabidopsis thaliana* genes: transcriptional regulation and gene expression induced by low temperature, ABA, osmoticum and dehydration", *Plant Mol. Biol.* 28:605–617 (1995).

Wang, H., and Cutler, A.J., "Promoters from kin1 and cor6.6, two homologous *Arabidopsis thaliana* low–temperature– and ABA–inducible genes, direct strong β–glucuronidase expression in guard cells, pollen and young developing seeds", *Plant Mol. Biol.* 28:619–634 (1995).

Weterings, K. et al., "Functional dissection of the promoter of the pollen–specific gene NTP303 reveals a novel pollen–specific, and conserved cis–regulatory element", *Plant J.* 8:55–63 (1995).

White, T.C. et al., "Regulation of BN115, a low–temperature–responsive gene from Winter *Brassica napus*", *Plant Physiol.* 106:917–928 (1994).

Wiersma, P.A., and Fils–Lycaon, B.R., "Molecular cloning and nucleotide suquence (Accession No. U39228) of a beta–glucosidase cDNA from ripening sweet cherry fruit (PGR95–127)", *Plant Physiol.* 110:337–(_).

Willmitzer, L., and Wagner, K.G., "The isolation of nuclei from tissue–cultured plant cells", *Exp. Cell Res.* 135: 64–77 (1981).

Wissenbach, M. et al. "Myb genes from *Hordeum vulgare*: tissue–specific expression of chimeric Myb promoter/Gus genes in transgenic tobacco", *Plant J.* 4:411–422 (1993).

Yang, N.–S. et al., "Maize sucrose synthase–1 promoter directs phloem cell–specific expression of Gus gene in transgenic tobacco plants", *Proc. Natl. Acad. Sci., USA* 87:4144–4148 (1990).

Zheng, L., and Poulton, J.E., "Temporal and spatial expression of amygdalin hydrolase and (R)–(+)–mandelonitrile lyase in black cherry seeds", *Plant Physiol.* 109:31–39 (1995).

Glycine max protein kinase 3 (SPK–3) mRNA Locus–GenBank: SOYSPK3 Accession# L19361.

*Brassica napus* serine/threonine protein kinase (BSK2) mRNA Locus–GenBank: BNASRKINB Accession# L12394.

*Arabidopsis thaliana* serine/threonine kinase mRNA Locus–GenBank: ATHSERTHR Accession# M91548.

*Arabidopsis thaliana* mRNA for protein kinase Locus–GenBank: ATPROKIN Accession# Z12120.

*Brassica napus* serine/threonine protein kinase (BSK1) mRNA Locus–GenBank: BNASRKINA Accession# L12393.

Glycine max protein kinase 2 (SPK–2) mRNA Locus–GenBank: SOYSPK2 Accession# L19360.

*A. thaliana* mRNA for thioglucoside glucohydrolase Locus–GenBank: ATPYK10 Accession# X89413.

*B. napus* mRNA for beta–glucosidase Locus–GenBank: BNBGL Accession# X82577.

*T. repens* mRNA for cyanogenic beta–glucosidase (linamarase) Locus–GenBank: TRBG104 Accession# X56733 S46824

*Prunus serotina* amygdalin hydrolase isoform AH I precursor, mRNA Locus–GenBank: PSU26025 Accession# U26025.

linamarase=beta–glucosidase [*Manihot esculenta*=cassava, Cranz, mRNA] Locus–GenBank: S35175 Accession# S35175.

*Prunus avium* beta–glucosidase mRNA Locus–GenBank: PAU39228 Accession #U39228.

*Hordeum vulgare* L. Beta–glucosidase (BGQ60) gene Locus–GenBank: BLYBGQ6 Accession# L41869.

*B. napus* mRNA for myurosinase Locus–GenBank: BNMYRO Accession# X60214.

*A. thaliana* TGG2 gene for myrosinase Locus–GenBank: ATTGG22 Accession# X79195.

*Arabidopsis thaliana* thioglucosidase mRNA Locus–GenBank: ATHTHIOGL Accession# L11454.

*S. turberosum* mRNA for inorganic phosphate transporter, Pho1 Locus–GenBank: STPHO1 Accession# X98890.

*S. tuberosum* mRNA for inorganic phosphate transporter, Pho2 Locus–GenBank: STPHO2 Accession# X98891.

Baszcynski, C.L., and Falis, L., "Isolation and nucleotide sequence of a genomic clone encoding a new *Brassica napus* napin gene", *Plant Mol. Biol.* 14: 633–635 (1990).

Goldstein, A.H., Baertlein, D.A., and Danon, A., "Phosphate starvation stress as an experimental system for molecular analysis", *Plant Mol. Biol. Rep.* 7(1): 7–16 (1989).

Kodama, H., Ito, M., Hattori, T., Nakamura, K., and Komamine, A., "Isolation of genes that are preferentially expressed at the $G_1/S$ boundary during the cell cycle in synchronized cultures of *Catharanthus roseus* cells", *Plant Physiol.* 95: 406–411 (1991).

Lambais, M.R., and Mehdy, M.C., "Suppresion of endochitinase, β–1,3–endoglucanase, and chalcone isomerase expression in bean vesicular–arbuscular mycorrhizal roots under different soil phosphate conditions", *MPMI* 6(1): 75–83 (1993).

Rao, N.N., and Torriani, A., "Molecular aspects of phosphate transport in *Escherichia coli*", *Mol. Microbiol.* 4(7): 1083–1090 (1990).

Vogel, K., and Hinnen, A., "The yeast phosphatase system", *Mol. Bicrobiol.* 4(12): 2013–2017 (1990).

Wanner, B.L., "Gene regulation by phosphate in enteric bacteria", *J. Cell. Biochem.* 51: 47–54 (1993).

Yoshida, K., Kuromitsu, Z., Ogawa, N., Ogawa, K., and Oshima, Y., "Regulatory circuit for phosphatase systhesis in *Saccharomyces cerevisiae*", In *Phosphate metabolism and cellular regulation in microorganisms*, (Ed.) Toriani–Gorine et al., Am. Soc. Microbiol., Washington, DC. pp. 49–55 (1987).

Soybean protein kinase (SPK–1) mRNA Locus–GenBank: SOYKINASE Locus–EMBL: GMKINASE Accession# L01453.

*M. crystallinum* MCPK9 gene for protein kinase Locus–GenBank: MCGEPK Locus–EMBL: MCGEPK Accession# Z26846.

*Arabidopsis thaliana* protein kinase mRNA Locus–GenBank: ATHPROKINB Locus–EMBL: ATPROKINB Accession# L05562.

*Arabidopsis thaliana* protein kinase mRNA Locus–GenBank: ATHPROKINA Locus–EMBL: ATPROKINA Accession# L05561.

Wheat protein kinase mRNA Locus–GenBank: TAPKABA1 Locus–EMBL: TAABAC Accession# M94726.

*S. typhimiurium* glutamate dehydrogenase (GDHA) gene Locus–GenBank: STYGDHA Locus–EMBL: STGDHA Accession# M24021 J04814.

Ovomucoid (fragment) Entry–Swiss: IOVO_DACNO Accession# P05617 (PIR: 131442).

Ovumucoid (fragment) Entry–Swiss: IOVO_ARGAR Accession# P05608 (PIR: C31443).

Ovomucoid (fragment) Entry–Swiss: IOVO_NYCNY Accession# P05566 (PIR: F31436).

Simian immunodeficiency virus complete genome Locus–GenBank: SIVCOMGNM Locus EMBL: SIVCOMGNM Accession# L06042.

*M. smegmatis* aspartokinase alpha and beta subunits Locus–GenBank: MSASDASK Entry–Swiss: AKAB_MYCM Accession# Z17372 (Swiss: P41403).

*Bacillus subtilis* aspartokinase 2 alpha and beta subunits Locus–GenBank: BCACPKII Entry–Swiss: AK2_BACSU Accession# J03294 (Swiss: P08495; P08496).

*Corynebacterium flavum* aspartokinase alpha and beta subunits Locus–GenBank: CORASKD Entry–Swiss: AKAB_CORFL Accession# L16848 (Swiss: P41398).

*Corynebacterium glutamicum* aspartokinase alpha and beta subunits Locus–GenBank: CGLYS Entry–Swiss: AKAB_CORGL Accession# X57226 (Swiss: P26512).

*Disintegrin eristicophin* (platelet aggregation activation inhibitor) Entry–Swiss: DISI_ERIMA Accession# P22826.

*Glomus versiforme* phospate transporter mRNA Locus–GenBank: GVU38650 Locus–EMBL: GV38650 Accession#U38650.

*S. cerevisiae* PHO84 gene for inorganic phosphate transporter Locus–GenBank: YSCPHO84 Locus–EMBL: SCPHO84 Accession#D90346 (Swiss: P25297).

Putative inorganic phosphate transporter C23D3.12, *S. pombe* chromosome I cosmid c23D3 Swiss–Prot locus: YAEC_SCHPO Accession# Q0852 Locus–GenBank: SPAC23D3 Locus–EMBL: SPAC23D3 Accession# Z64354.

Hypothetical sensor–like histidine kinase, *Bacillus subtilis* 15 kb chromosome segment contains the iol operon Swiss–Prot locus: YXDK_BACSU Accession# P42422 Locus–GenBank: BACIOLO Locus–EMBL: BSE83A Accession# D14399.

*Bacillus subtilis* genome sequence between the iol and hut operon Locus–GenBank: D45912 Accession# D45912.

Ryanodine receptor, skeletal muscle (skeletal muscle calcium release channel) Entry–Swiss: RYNR_HUMAN Locus–GenBank: HUMRYR Locus–EMBL: HSRYR Accession# J05200 (Swiss: P21817).

Ryanodine receptor (human) Locus–GenBank: A20359 Locus–EMBL: A20359 Accession# A20359.

Ryanodine receptor—pig, *S. scrofa* mRNa for calcium release channel (CRC) Entry–PIR: S18135 Locus–GenBank: SSCRCRNA Locus–EMBL: SSCRCRNA Accession# X62880 (PIR: S18135).

*Sus scrofa* ryanodine receptor (RYR1) mRNA Locus–GenBank: PIGRYRMH Locus–EMBL: SSRYRMH Accession# M91451.

*Sus scrofa* ryanodine receptor (RYR1) gene Locus–GenBank: PIGRYRN Locus–EMBL: SSRYRN Accession# M91452.

ATP synthase protein 8 Entry–Swiss: ATP8_DROYA Accession# P03933 Locus–GenBank: MIDYCOX Accession# X00924 Locus–GenBank: MIDYRRN Accession# X03240.

ATP synthase protein 8, *D. melanogaster* mitochondrial cytochrome c oxidase Locus–GenBank: DROMTM1 Locus–EMBL: MIDMM1 Accession# J01404 (Swiss: P03932).

Adenylate cyclase, *N. crassa nac* gene coding for adenylate cyclase Entry–Swiss: CYAA_NEUCR Locus–GenBank: NEUNAC Locus–EMBL: NCNAC Accession# D00909 (Swiss: Q01361).

Lyase, Corn smut fungus uac1 gne Entry–Swiss: CYAA_USTMA Locus–GenBank: USMUAC1A Locus–EMBL: USMUAC1A Accession#L33918 (Swiss: P49606).

*S. cerevisiae* chromosome X DNA (cosmid 83) Locus–GenBank: SCXCOSM83 Locus–EMBL: SCXCOSM83 Accession# X87611.

Yeast (*S. cerevisiae*) adenylate cyclase gene (CYR1) Locus–GenBank: YSCCYR1 Locus–EMBL: SCCYR1 Accession# M12057.

Adenylate cyclase (ATP pyrophosphate lyase), *S. cerevisiae* chromosome X reading frame ORF YJL005w Entry–Swiss: CYAA_YEAST Locus–GenBank: SCYJL005W Locus–EMBL: SCYJL005W Accession# Z49280 (Swiss: P08678).

Probable calcium–transporting ATPase 4, *Saccharomyces cerevisiae* chromosome I left arm Entry–Swiss: ATC4_YEAST Locus–GenBank: SCU12980 Locus–EMBL: SC12980 Accession# U12980 (Swiss: P39524).

*H. vulgaris ras*1 mRNA Locus–GenBank: HVRAS1 Accession# X78597.

1–phosphatidylinositol 3–kinase homolog DRR1–yeast (*Saccharomyces cerevisiae*) Entry–PIR: A54428 Locus–GenBank: YSCDRR1A Locus–EMBL: SCDRR1A Accession# L19540 (PIR# A54428).

Tor1 protein–yeast (*S. cerevisiae*), *S. cerevisiae* TOR1 gene Entry–PIR: S43490 Locus–GenBank: SCTOR1 Locus–EMBL: SCTOR1 Accession# X74857 (PIR# S43490).

Phosphatidylinositol 3–kinase TOR1 Entry–Swiss: TOR1_YEAST Accession# P35169.

*S. cerevisiae* chromosome X reading frome ORF YJR066w Locus–GenBank: SCYJR066W Locus–EMBL: SCYJR066W Accession# Z49566.

*Saccharomyces cerevisiae* DRR1 gene Locus–GenBank: YSCDRR1A Locus–EMBL: SCDRR1A Accession# L19540.

*Homo sapiens* tripetydyl peptidase II mRNA Locus–GenBank: HUMTPPII Locus–EMBL: HSTPPII Accession# M55169 J05299.

Tripeptidyl–peptidase II Entry–Swiss: TPP2_HUMAN Locus–GenBank: HUMTPPIIA Locus–EMBL: HSTPPIIA1 Accession# M73047 (Swiss: P29144).

*Rattus norvegicus* tripeptidylpeptidase II mRNA Locus–GenBank: RNU50194 Accession# U50194.

*M. musculus* mRNA for tripeptidyl peptidase II Locus–GenBank: MMTPII Locus–EMBL: MMTPII Accession# X81323.

```
CCACGCGTCCGAGAAGATTCATCAAAAAGAAAAAAAAAATAATAAAGGACCATTTTAGGGAAGTGAGAACAAAAACAAAA  80

GTGGTAGCTATGGAGAAGTATGAGATGGTGAAGGATTTAGGATTTGGTAATTTCGGATTGGCTCGGCTTATCCGTAATAA 160
         M  E  K  Y  E  M  V  K  D  L  G  F  G  N  F  G  L  A  R  L  I  R  N  K

GCAAACAAACGAGCTTGTGGCTGTCAAATTCATCGATCGAGGCTACAAGATAGATGAGAACGTTGCAAGAGAAATAATCA 240
  Q  T  N  E  L  V  A  V  K  F  I  D  R  G  Y  K  I  D  E  N  V  A  R  E  I  I

ATCATAGAGCTCTCAACCATCCGAATATTGTTCGGTTTAAAGAGGTTGTTTTAACTCCGACACATCTTGGAATAGTAATG 320
  N  H  R  A  L  N  H  P  N  I  V  R  F  K  E  V  V  L  T  P  T  H  L  G  I  V  M

GAGTATGCAGCTGGAGGAGAACTGTTCGAGCGGATATCTAGCGTGGGTCGATTTAGCGAACGTGAGGCAAGATATTTCTT 400
  E  Y  A  A  G  G  E  L  F  E  R  I  S  S  V  G  R  F  S  E  R  E  A  R  Y  F  F

TCAACAACTCATTTGTGGAGTCCATTACTTACATGCATTGCAAATATGCCATAGAGATCTGAAATTAGAAAACACATTGC 480
  Q  Q  L  I  C  G  V  H  Y  L  H  A  L  Q  I  C  H  R  D  L  K  L  E  N  T  L

TTGATGGAAGCCCAGCACCACGTTTAAAAATTTGTGATTTTGGCTACTCAAAGTCTTCTGTTCTGCACTCCAACCCAAAA 560
  L  D  G  S  P  A  P  R  L  K  I  C  D  F  G  Y  S  K  S  S  V  L  H  S  N  P  K

TCAACGGTGGGAACTCCGGCATATATAGCACCGGAAGTTTTTTGTCGATCGGAATACGACGGAAAGTCAGTTGATGTGTG 640
  S  T  V  G  T  P  A  Y  I  A  P  E  V  F  C  R  S  E  Y  D  G  K  S  V  D  V  W

GTCTTGTGGAGTGGCCCTCTATGTTATGTTGGTAGGAGCTTATCCATTCGAAGACCCTAAAGACCCTCGCAATTTCCGAA 720
  S  C  G  V  A  L  Y  V  M  L  V  G  A  Y  P  F  E  D  P  K  D  P  R  N  F  R

AAACTGTTCAGAAAATAATGGCCGTAAACTACAAGATTCCAGGATATGTTCACATATCCGAAGACTGCAGAAAGTTACTA 800
  K  T  V  Q  K  I  M  A  V  N  Y  K  I  P  G  Y  V  H  I  S  E  D  C  R  K  L  L

TCTCGTATATTTGTTGCCAATCCGTTACATAGAAGTACGCTTAAAGAGATTAAGAGTCATGCATGGTTCCTAAAGAATTT 880
  S  R  I  F  V  A  N  P  L  H  R  S  T  L  K  E  I  K  S  H  A  W  F  L  K  N  L

GCCAAGAGAATTAAAGGAGCCAGCACAAGCAATCTATTACCAAAGGAATGTTAATCTTATTAATTTTTCTCCTCAAAGAG 960
  P  R  E  L  K  E  P  A  Q  A  I  Y  Y  Q  R  N  V  N  L  I  N  F  S  P  Q  R

TAGAGGAGATTATGAAGATAGTTGGTGAGGCAAGACCGATTCCAAACCTTTCTCGCCCGGTCGAATCGCTTGGATCAGAT 1040
  V  E  E  I  M  K  I  V  G  E  A  R  P  I  P  N  L  S  R  P  V  E  S  L  G  S  D

AAAAAAGATGATGATGAAGAAGAATATTTGGATGCTAATGATGAAGAATGGTATGATGATTACGCATAGACAATAAAAAT 1120
  K  K  D  D  D  E  E  Y  L  D  A  N  D  E  E  W  Y  D  D  Y  A

GTATTATATGTTGTCAAATTATGAACGGTACGAACATGAACGGTACGTTCGTATTTGTAATTATCTATATGAATTTCGGT 1200

TTTTCTTTTTCATAATCACCAAATTAGTTTAAATGAAAAAAAAAAAAAAA 1250
```

FIGURE 5

```
psr1 A. thaliana cDNA  CCACGCGTCCGAGAAGATTCATCAAAAAGAAAAAAAAAATAATAAAGGACCATTTTAGGGAAGTGAGAAG  70
psr1 B. nigra cDNA     ---------------------------------------------------------------------  1 psr1 A. thaliana cDNA  AAAAACAAAAGTGGTAGCTATGGAGAAGTATGAGATGGTGAAGGATTTAGGATTTGGTAATTTCGGATTG  140
psr1 B. nigra cDNA     ---------------------------------------------------------------------  1 psr1 A. thaliana cDNA  GCTCGGCTTATCCGTAATAAGCAAACAAACGAGCTTGTGGCTGTCAAATTCATCGATCGAGGCTACAAGA  210
psr1 B. nigra cDNA     ---------------------------------------------------------------------  1 psr1 A. thaliana cDNA  TAGATGAGAACGTTGCAAGAGAAATAATCAATCATAGAGCTCTCAACCATCCGAATATTGTTCGGTTTAA  280
psr1 B. nigra cDNA     ---------------------------------------------------------------------  1 psr1 A. thaliana cDNA  AGAGGTTGTTTTAACTCCGACACATCTTGGAATAGTAATGGAGTATGCAGCTGGAGGAGAACTGTTCGAG  350
psr1 B. nigra cDNA     ------------------------------------------------------------------CGG  3 psr1 A. thaliana cDNA  CGGATATCTAGCGTGGGTCGATTTAGCGAACGGTGAGGCAAGATATTTCTTTCAACAACTCATTTGTGGAG  420
psr1 B. nigra cDNA     CGGATATCAAGCGCGGGTCGATTCAGCGAACCTGAGGCTAGATATTTCTTTCAACAACTCATTTGCGGAG  73 psr1 A. thaliana cDNA  TCCATTACTTACATGCATTGCAAATATGCCATAGAGATCTGAAATTAGAAAACACATTGCTTGATGGAAG  490
psr1 B. nigra cDNA     TGCATTACTTACATGCAATGCAAATATGCCATAGAGATCTGAAATTAGAAAACATTTTGCTTGATGGAAG  143 psr1 A. thaliana cDNA  GCCAGCACGACGTTTAAAAATTTGTGATTTTGGCTACTGAAAGTCTTCTGTTCTGCAGTCCAACCGAAAA  560
psr1 B. nigra cDNA     TCCAGCACCCCGTCTAAAAATTTGTGATTTTGGCTACTCGAAGTCTTCTATTCTGCATTGAAACCCTAAA  213 psr1 A. thaliana cDNA  TCAACGGTGGGAACTCCGGCATATATAGCACCGGAAGTTTTTTGTCGATCGGAATACGACGGAAAGTGAG  630
psr1 B. nigra cDNA     TCAACGGTGGGGAGCCCGGCATATATAGCACCGGAAGTTTTTGGTCGTTCGGAATACGACGGGAAGTCTG  283 psr1 A. thaliana cDNA  TTGATGTGTGGTCTTGTGGAGTGGCCCTCTATGTTATGTTGGTAGGAGCTTATCGATTCGAAGACCCTAA  700
psr1 B. nigra cDNA     TTGATGTGTGGTCTTGTGGAGTGGCACTCTATGTTATATTGGTAGGAGCTTACCCTTTCGAAGACCGAA  353 psr1 A. thaliana cDNA  AGACCCTCGCAATTTCCGAAAAACTGTTCAGAAAATAATGGCGGTAAACTACAAGATTCCAGGATATGTT  770
psr1 B. nigra cDNA     AGATCCTCGCAATTTCCGAAAAACTGTCCAGAAAATAATGGCTGTTAAGTACAAGATTCAAGGATATGTT  423 psr1 A. thaliana cDNA  CACATATCCGAAGACTGCAGAAAGTTAGTATCTCGTATATTTGTTGCCAATCCGTTACATAGAAGTACGC  840
psr1 B. nigra cDNA     CACATATCTGAAGATTGCAGGAACTTATTATCTCGTATATATGTTGCCAATCGATCACATAGAATTACGC  493 psr1 A. thaliana cDNA  TTAA---AGAGATTAAGAGTCATGCATGGTTCCTAAAGAATTTGCCAAGAGAATTAAAGGAGCCAGCACA  907
psr1 B. nigra cDNA     CTATCATAGAGATTAGGAGTCATGCATGGTTCCTAAAGAATTTGCCAAGAGAACTAAAGGAGTCCGCACA  563 psr1 A. thaliana cDNA  AGCAATCTATTAGCAAAGGAATGTTAATCTTATTAATTTTTCTCCTCAAACAGTAGAGGAGATTATGAAG  977
psr1 B. nigra cDNA     AGCAGTCTATTATCAAAGGAATGTTAATCTTATTAACCTTTCTCCTCAAAGGGTAGAGGAGATTATGAAG  633 psr1 A. thaliana cDNA  ATAGTTGGTGAGGCAAGAC-CGATTCCAAACCTTTCTCGCCCGGTCGAATCGCTTGGATGAGATAAAAAA  1046
psr1 B. nigra cDNA     ATACTGGGTAAGGCAAGAAAGCATTCCAGACCTTTCGACGCCCACTCGA-TCCGATGGAAATGGTGAAAAA  702 psr1 A. thaliana cDNA  GATGATG---ATG------AAGAAGAATATTTGGATGCTAATGATGAAGAATGGTATGATGATTACGCAT  1107
psr1 B. nigra cDNA     GATGATGTAGATGCTGAAGAAGAAGAATATTTGGATGCTAATGATGAAGAATGTGATGATGAATATCCAT  772 psr1 A. thaliana cDNA  AGACAATAAAAATGTATTATATGTTGTCAAATTATGAACGGTACGAACATGAACGGTACGTTCGTATTTG  1177
psr1 B. nigra cDNA     AGACAA-AAATAT-TACTA-ATGTTGTGAAATTATGAGAAGTACTTGTA---ATTTTATTTTTGAATTT-  836 psr1 A. thaliana cDNA  TAATTATCTATATGAATTTCGGTTTTTCTTTTTCATAATCACCAAATT-AGTTTAAATG---AAAAAAAA  1243
psr1 B. nigra cDNA     CGGTTAAAGTTATTAAGTTAAGAGAACATAACAAATTAAAATAAAATTTATTTTGAGTACCAAAAAAAAA  905 psr1 A. thaliana cDNA  AAAAAAA                                                                 1250
psr1 B. nigra cDNA     AAAAAAA                                                                 912
```

FIGURE 6

```
ccacgcgtccgagaagattcatcaaaaagaaaaaaaaataataaaggaccattttaggg    60
aagtgagaacaaaaacaaaagtggtagctatggagaagtatgagatggtgaaggatttag  120
gatttggtaatttcggattggctcggcttatccgtaataagcaaacaaacgagcttgtgg  180
ctgtcaaattcatcgatcgaggctacaagatagatgagaacgttgcaagagaaataatca  240
atcatagagctctcaaccatccgaatattgttcggtttaaagaggttgttttaactccga  300
cacatcttggaatagtaatggagtatgcagctggaggagaactgttcgagcggatatcta  360
gcgtgggtcgatttagcgaacgtgaggcaagatatttctttcaacaactcatttgtggag  420
tccattacttacatgcattgcaaatatgccatagagatctgaaattagaaaacacattgc  480
ttgatggaagcccagcaccacgtttaaaaatttgtgattttggctactcaaagtcttctg  540
ttctgcactccaacccaaaatcaacggtgggaactccggcatatatagcaccggaagttt  600
tttgtcgatcggaatacgacggaaagtcagttgatgtgtggtcttgtggagtggccctct  660
atgttatgttggtaggagcttatccattcgaagaccctaaagaccctcgcaatttccgaa  720
aaactgttcagaaaataatggccgtaaactacaagattccaggatatgttcacatatccg  780
aagactgcagaaagttactatctcgtatatttgttgccaatccgttacatagaagtacgc  840
ttaaagagattaagagtcatgcatggttcctaaagaatttgccaagagaattaaaggagc  900
cagcacaagcaatctattaccaaggaatgttaatcttattaattttctcctcaaagag    960
tagaggagattatgaagatagttGGTGAGGCAAGACCGATTCCAAACCTTTCTCGCCCGG 1020
TCGAATCGCTTGGATCAGATAAAAAAGATGATGATGAAGAAGAATATTTGGATGCTAATG 1080
ATGAAGAATGGTATGATGATTACGCATAGACAATAAAAATGTATTATATGTTGTCAAATT 1140
ATGAACGGTACGAACATGAACGGTACGTTCGTATTTGTAATTATCTATATGAATTTCGGT 1200
TTTCTTTTTCATAATCACCAAATTAGTTTAAATGAAAAAAAAAAAAAA             1250
```

FIGURE 7

```
psr1 A. thaliana  ME-KYEMVKDLGFGNFGLARLIRNKQTNELVAVKFIDRGYKIDENVAREIINHRALNHPNIVRFKEVVLTPTHLGIVMEY  79
PSR1 B. nigra     -------------------------------------------------------------------------------   1
SPK3 Soybean      MD-KYEAVKDLGAGNFGVARLMRNKEIKELVAMKYIERGQKIDENVAREIINHRSLRHPNIIRFKEVVLTPTHLAIVMEY  79
BSK2 B. napus     ME-KYELVKDIGAGNFGVARLMKVKNSKELVAMKYIERGPKIDENVAREIINHRSLRHPNIIRFKEVVLTPTHLAIAMEY  79
ASK1 A. thaliana  MD-KYELVKDIGAGNFGVARLMKVKNSKELVAMKYIERGPKIDENVAREIINHRSLRHPNIIRFKEVVLTPTHLAIAMEY  79
ASK2 A. thaliana  MD-KYDVVKDLGAGNFGVARLLHKDIKELVAMKYIERGRKIDENVAREIINHRSFKHPNIIRFKEVILTPTHLAIVMEY   79
BSK1 B. napus     ME-KYELVKDIGAGNFGVARLMKVKDSKELVAMKYIERGPKIDENVAREIYNHRSLRHPNIIRFKEVVLTPTHLAIAMEY  79
SPK2 Soybean      MDERYETLKELGSGNFGVARLAKDKEIIGELVAIKYIERGKKIDANVQREIVNHRSLRHPNIIRFKEVFLTPTHLAIVLEY 80 psr1 A. thaliana  AAGGELFERISSVGRFSEREARYFFQQLICGVHYLHALQICHRDLKLENTLLDGSPAPRLKICDFGYSKSSVLHSNPKST  159
PSR1 B. nigra     --------RISSAGRFSEAEARYFFQQLICGVHYLHAMQICHRDLKLENILLDGSPAPRLKICDFGYSKSSILHSNPKST   72
SPK3 Soybean      AAGGELFERICNAGRFSEDEARYFFQQLISGVHYCHAMQICHRDLKLENTLLDGSPAPRLKICDFGYSKSSLLHSRPKST  159
BSK2 B. napus     AAGGELFERICSAGRFSEDEARYFFQQLISGVSYCHAMQICHRDLKLENTLLDGSPAPRLKICDFGYSKSSLLHSRPKST  159
ASK1 A. thaliana  AAGGELFERICSAGRFSEDEARYFFQQLISGVSYCHAMQICHRDLKLENTLLDGSPAPRLKICDFGYSKSSLLHSRPKST  159
ASK2 A. thaliana  ASGGELFDRICTAGRFSEAEARYFFQQLICGVDYCHSLQICHRDLKLENTLLDGAPAPLLKICDFGYSKSSILHSRPKST  159
BSK1 B. napus     AAGGELFERICGAGRFSEDEARYFFQQLISGVSYCHAMQICHRDLKLENTLLDGSPAPRLKICDFGYSKSSLLHSRPKST  159
SPK2 Soybean      AAGGELFERICNAGRLSEDEARFFFQQLISGVSYCHSMQICHRDLKLENTLLDGNPAPRLKICDFGFSKSALLHSQPKST  160 psr1 A. thaliana  VGTPAYIAPEVFCRSEYDGKSVDVWSCGVALYVMLVGAYPFEDPKDPRNFRKTVQKIMAVNYKIPGYVHISEDCRKLLSR  239
PSR1 B. nigra     VGTPAYIAPEVFGRSEYDGKSVDVWSSGVALYVILVGAYPFEDPKDPRNFRKTVQKIMAVKYKIQGYVHISEDCRNLLSR  152
SPK3 Soybean      VGTPAYIAPEVLSRREYDGKLADVWSCGVTLYVMLVGAYPFEDQDDPRNFRKTIDRIMAVQYKIRDYVHISQDCRHLLSR  239
BSK2 B. napus     VGTPAYIAPEVLSRREYDGKMADVWSCGVTLYVMLVGAYPFEDQEDPKNFRKTIQKIMAVQYKIRDYVHISQDCKHLLSR  239
ASK1 A. thaliana  VGTPAYIAPEVLSRREYDGKMADVWSCGVTLYVMLVGAYPFEDQEDPKNFRKTIDKIMAVQYKIRDYVHISQDCKNLLSR  239
ASK2 A. thaliana  VGTPAYIAPEVLSRREYDGKHADVWSCGVTLYVMLVGAYPFEDPNDPKNFRKTIQRIMAVQYKIRDYVHISQECKHLLSR  239
BSK1 B. napus     VGTPAYIAPEVLSRREYDGKMADVWSCGVTLYVMLVGAYPFEDQEDPKNFRKTIDKIMAVQYKIRDYVHISQDCKHLLSR  239
SPK2 Soybean      VGTPAYIAPEVLSRKEYDGKVADVWSCGVTLYVMLVGAYPFEDPEDPKNFRKSIGRIMSVQYAIRDYVRVSKECRHUISR  240 psr1 A. thaliana  IFVANPLHRST-LKEIKSHAWFLKNLPRELKEPAQAIYYQRNVLINFSPQRVEEIMKIVGEARPIPNLSRPVESLGSDK   318
PSR1 B. nigra     IIYVANRSHRIIPIIEIRSHAWFLKNLPRELKESAQAVYYQRNVNLINLSPQRVEEIMKILGKARTILPDLSRPLESHGNGE 232
SPK3 Soybean      IFVANPLRRIS-LKEIKSHPWFLKNLPRELTESAQAVYYQRGNP--SFSIQSVEEIMKIVGEARDPFPVSRPVKGFGWDG  316
BSK2 B. napus     IFVANSLKRIT-IAEIKKHPWFLKNLPRELTETAQAANFKKENP--TFSPQTAEEIMKIVDDAKTPFPVSRSIGGFGWGG  316
ASK1 A. thaliana  IFVANSLKRIT-IAEIKKHSWFLKNLPRELTETAQAANFKKENP--TFSLQTVEEIMKIVADAKTPFPVSRSIGGFGWGG  316
ASK2 A. thaliana  IFVINSAKRIT-LKEIKNHPWYLKNLPKELLESAQAAYYKRDT---SFSLQSVEDIMKIVGEARNPAPSTSAVKSSGSGA  315
BSK1 B. napus     IFVANSLKRIT-IAEIKKHPWFTKNLPRELTETAQAANFKKENP--TFSAQTAEEIMKIVDDAKTPFPVSRSIGGFGWGG  316
SPK2 Soybean      IFVANRAKRIN-ISEIKQHLWFRKNLPREIIEAERRGYEETQKDQ---PSQSVEEIMQIIQEARTKIHTGEQAGT---GT  313 psr1 A. thaliana  KDD---DEEEYLDANDEEW--------YDDYA.                                                340
PSR1 B. nigra     KDDVDAEEEEYLDANDEEC--------DDENP                                                 256
SPK3 Soybean      EED------------EGHEDVEEEEDEEDEYDKRVKEVHASGEFQIS                                  351
BSK2 B. napus     KGD---EEEGEVD---EEEVVEEEEDEEDEYDKTVKEAHASGEV                                     354
ASK1 A. thaliana  NGDADGKEEDAEDVEEEEEEVEEEEDDEDEYDKTVKEVHASGEVRIS                                  391
ASK2 A. thaliana  D------EEEEEDVEAE---VEEEEDDEDEYEKHVKEAQSCQESDKA                                  353
BSK1 B. napus     EGDLEGKEEEEVD---EEEV-EEEEDEEDEYDKTVKEVHASGEVRIS                                  359
SPK2 Soybean      SDVVRGDEAN-----------EEVDINCHFAKYLTLD                                            339
```

Decoration 'Decoration #1': Box residues that match psr1 A. thaliana exactly.

Sense Construct with Constitutive Promoter

Anti-Sense Construct with Constitutive Promoter

Sense Construct with Seed-Specific Promoter

Anti-Sense Construct with Seed-Specific Promoter

```
AATCATCATAAACTTGTTCTCTTCCAGAAGAAACTAAAAACAAAAATGGCATTGCAAAAGTTTCCTCTCATGGGGCTGCT  80
+1                                              MetAlaLeuGlnLysPheProLeuMetGlyLeuLe

TTTGCTCCTAACCATCCTCGTCTCTGTGACAACAGCGGTTGATGATCCTGTTTGCCCGGCGACTTCCAAGCTAAGCCGAG 160
uLeuLeuLeuThrIleLeuValSerValThrThrAlaValAspAspProValCysProAlaThrSerLysLeuSerArgA

CAAGTTTCCCTAATGGGTTTTTGTTTGGCACGGCTACTGCTGCGTTTCAGGTACAACAGATTTACTAAATCATAGTTCAA 240
laSerPheProAsnGlyPheLeuPheGlyThrAlaThrAlaAlaPheGln

AAAACAAAAAGTAGTGTCGTTATTGTGTTTCTATCTGAATTCAAATCCATATTTTTAAAATATGGTTTTTTTTTATGTAA 320
AAGTTGCTCAAAATATGTTATACCTATCATTTGAAATCATTTGTGCATGTGATATTCCTCAACTCATCAACTATTTTTG 400
TTATGTCATTAGGTCGAAGGTGCAATTAATGAAACTTGTCGTGGACCGGCTCTATGGGATATCTACTGTAGAAGAAATCC 480
                        ValGluGlyAlaIleAsnGluThrCysArgGlyProAlaLeuTrpAspIleTyrCysArgArgAsnPr

AGGTGAGTGTACTCGTATAATCTACATTCTCAATACAGTATGTTTAAATATTAAATTAAATTTAACTAATTAATATCAAT 560
oGlyGluCysThrG

ACATAGCCATTAATTTTCTTAATTACTTTCAAATTACAGAGAGATGTAGTGGCGACCACGCCGATGTGGCCGTTGATTTC 640
lnArgCysSerGlyAspHisAlaAspValAlaValAspPhe

TTCCATCGTTATAAGGTATATATTAATATAAATTTAAGACAAACATAACTTATATTCTCGAGATGTTATTGAAATTTTGC 720
PheHisArgTyrLys

CTTGTCTTAAAAATGTTTGTAGGAAGATATTCAGCTAATGAAGAATCTAAACACAGATGCATTCAGACTCTCAATCGCAT 800
                        GluAspIleGlnLeuMetLysAsnLeuAsnThrAspAlaPheArgLeuSerIleAlaT

GGTCAAGAATATTTCCTCGTGAGTATATGTCTGCAGATCTCTAGTTTGATTTTGTTTTAATCGAATTTGGTGAAATTAGA 880
rpSerArgIlePheProH

TTTATGTGATTGTTATATAATACTAATAACCAATGAATTTAGATGATGTATATGTGAATGTTGAAGTATCAATAACTAAT 960
GAAACAAACTGTAATGCTTTATTAGATGGGAGAAAGGAGAAGGGAGTGAGTCAAGCTGGTGTGCAATTCTACCACGAGCT 1040
                        IsGlyArgLysGluLysGlyValSerGlnAlaGlyValGlnPheTyrHisGluLe

CATCGATGAACTCCTTAAAAATGGTTATATACATATAAAATACCTAGTTCACAAAAATACAAGTAATATAGTATCCTTAT 1120
uIleAspGluLeuLeuLysAsnG

TTAACATTTCTTTCTATTTTACGTCATAAATAGGTATAGTTCCGTTTGTGACTGTTTTCCATTGGGACACTCCACAAGAT 1200
                            lyIleValProPheValThrValPheHisTrpAspThrProGlnAsp

TTGGAAGACGAATATGGCGGTTTCTTAAGCCAAAACATTGTGTATGTTTTTGTAAATTAAACAAAATACATTTAGTTAAG 1280
LeuGluAspGluTyrGlyGlyPheLeuSerGlnAsnIleVa

TTTATATGGAAATTATTAATTTGGTATCTTTTTTTTTGCAAAAATACAGGAAAGATTTTCGAGAATATGCAGATTATGT 1360
                                                ILysAspPheArgGluTyrAlaAspTyrVa

TTTCACTGAATACGGTGGAAAAGTGAAAAACTGGATCACTTTCAACGAGCCATGGGTCTTTGCTCACGCAGGTTACGACT 1440
lPheThrGluTyrGlyGlyLysValLysAsnTrpIleThrPheAsnGluProTrpValPheAlaHisAlaGlyTyrAspL

TAGGAAAGAAAGCACCAGGACGTTGTTCTCGCTACGTTCCAGGTTGCGAAGACCGAGAGGGACAATCTGGTAAAGAGGCT 1520
euGlyLysLysAlaProGlyArgCysSerArgTyrValProGlyCysGluAspArgGluGlyGlnSerGlyLysGluAla

TATCTAGTCAGTCACAATCTCCTCAACGCTCACGCAGAAGCTGTTGAAGTTTTCCGCCAAAAGGTAGTTTACATTAGATA 1600
TyrLeuValSerHisAsnLeuLeuAsnAlaHisAlaGluAlaValGluValPheArgGlnLys
```

FIGURE 14A

```
TAAATCATAATTAATTATCAGGTCACATTAGATATAAATCACAATTAATTATCAGGTTTCGAATCTTAAAATAGGTTGTT 1680
TTGTGTTGTGTTTATGGACATAGGTTAAAGGTGGGAAAATCGGAATCGCACATAGTCCGGCTTGGTTCGAACCACATGAT 1760
                       ValLysGlyGlyLysIleGlyIleAlaHisSerProAlaTrpPheGluProHisAsp

CTTAAAGATTCAAATGACGCTCCAACTGTTAGCCGTGTACTTGACTTTATGTTGGGATGGTAAGTATATATTATGTTAGA 1840
LeuLysAspSerAsnAspAlaProThrValSerArgValLeuAspPheMetLeuGlyTr

AAATGGTTTCTCGTATATAATTTCATAAAAATTAATGTAGTTATTAATTTTGTGTAGGCATCTGGAGCCAACTACTTCGG 1920
                                                      pHisLeuGluProThrThrSerG

GAGATTATCCACAAATCATGAAAGACCTTCTTGGTTACAGATTGCCTCAATTTACTGCTGCACAAAAAGCAAAATTGAAA 2000
lyAspTyrProGlnIleMetLysAspLeuLeuGlyTyrArgLeuProGlnPheThrAlaAlaGlnLysAlaLysLeuLys

GATTCGACCGATTTCGTAGGGCTTAACTACTATACTTCGACATTTTCAAATTATAATGAGAaGCCAGATCCGtCTAAACC 2080
AspSerThrAspPheValGlyLeuAsnTyrTyrThrSerThrPheSerAsnTyrAsnGluLysProAspProSerLysPr

AAGTTGGAAGCAAGATTCTCTTGTTTCCTGGGAACGTAAGTTTTTTTTTGTTTTCCGTACATGAAACCAAACCAAGAAAC 2160
oSerTrpLysGlnAspSerLeuValSerTrpGluP

TAAAGATAAAAGGTTTTATAATACTAATTGATATGCATACATTTTCACTTTTTATTTTTCAGCTAAGAATGTAGATCACA 2240
                                                                roLysAsnValAspHisS

GCGCCATTGGTAGCATGGTAAGCGTTTGATTAAACTAGTCCTAGTTTGATTGTTAATTTTTGTCTACGACATAACATTTT 2320
erAlaIleGlySerMet

CACCATTGCTTTATTTCAGCCTCTTACTGCTGCATTGCCCGTCTACGCTAAAGGATTTAGAAAGCTTTTAAAGTACATCA 2400
               ProLeuThrAlaAlaLeuProValTyrAlaLysGlyPheArgLysLeuLeuLysTyrIleL

AGGACAAATACGCAAACCCGGAGATTATGATAATGGAAAATGGTAACTCGAGATTTATTGTTATATTTGTGTGTTGATTT 2480
ysAspLysTyrAlaAsnProGluIleMetIleMetGluAsnG

AATCTTAACTCTTAAGAGTAATATACTGATCATTATAATGTTGTTTTTCTAGGATATGGAGATAAACTTGGGACCACAG 2560
                                                    lyTyrGlyAspLysLeuGlyThrThrA

ATTCGGTTGACGTTGGTACTGCTGATCATAACAGGAAATATTATCTTCAGAGGCATCTTCTGGCTATGAACGAGGCTATT 2640
spSerValAspValGlyThrAlaAspHisAsnArgLysTyrTyrLeuGlnArgHisLeuLeuAlaMetAsnGluAlaIle

TGGTAAGCCTTTTATTATTTGATAGATTGACTAACGATTCTATTGAATGGTCTAATTAAGAACATAATTGTGTTTGTGCA 2720
Cy

GCATCGATAAGGTGAGAGTTACGGGATACTTTGTATGGTCATTGTTGGATAACTTCGAATGGCAAGATGGTTACAAAAAC 2800
   sIleAspLysValArgValThrGlyTyrPheValTrpSerLeuLeuAspAsnPheGluTrpGlnAspGlyTyrLysAsn

AGATTCGGACTCTATTACGTCGATTTCAAAAATAACCTCACACGTTATGAGAAAGAATCAGCCAAGTATTACAAAGATTT 2880
ArgPheGlyLeuTyrTyrValAspPheLysAsnAsnLeuThrArgTyrGluLysGluSerAlaLysTyrTyrLysAspPh

CCTCGCTCAAGGTGTTCGTCCATCCGCACTCAAGAGGGATGAGCTTTAAGTTATATTTTGAGGATTTCGTTTTCTATTCG 2960
eLeuAlaGlnGlyValArgProSerAlaLeuLysArgAspGluLeu *

ATGTTTTTCCTATGTTTTAGTTTGTGATTGACCACGCACGATTCATGAGTCGTGGTTAATAATAATAAAAGTGTTTCGTT 3040
TTCCTTCAATCTCTAGCTTATTCGACAAGATCAAAGAAGGCTTTAGTTTTAATGACGTTATCCTTTTTGAGAATCAATAT 3120
GTGAAGTTAAATATGTTTTACCTTCCAAACTTGAAGAAAAATTGAATCATACAACCTTAACATTAAAAAATTTATGAGTT 3200
ACAAAATGATGTAAGAAAATATCATTAGTTTTAGAAAATTAAAAATACGAATTTACCTCTATACATAGAAATAGATTAGG 3280
AAATAATTTGACGTCGTCTTAACAACTAAGTACAAACATTTCAAAAACTAACAACTTAAACGTTGGCGATGAAATAAACA 3360
ATGGCAATTCATTTTCCCAAACAGTTCTAATATTTTATTTTTGAAAGTCACTAGTTTAGATTAAAAAAACAGGACGACCAG 3440
CAAGAGAAGATATCTCTTTTTCACTCATTTGGCCAAGCGTATTTTCTATATACCTTAAGGAAATAAAATCCATGCATGAT 3520
GCAACCAAATAAATCCACCATGCAATACCAACATCATTCATTACTTTGGAAATTCATATTTCATTCTTAGCAAGCAAAAA 3600
AAAACAAAAAAAAACAATCAAACGTATGTGTTAATAATGAAATCATCACATTCTATCTTACTAGTAGTCACTTATCAAAA 3680
ACGATTTATGTAAATAGTGATTTTCAAGATTTTTTTTTAAAAGCAAAAAATTTAAAGGCCAACTCACTTTCAGACTGTT 3760
TCTTTTGTAAAATTGAGAATT 3781
```

FIGURE 14B

```
CCGGCGTTGATTTCTTCCATCGTTATAAGGAAGATATCCAACTTATGAAGAATCTAAACA  60
          G  V  D  F  F  H  R  Y  K  E  D  I  Q  L  M  K  N  L  N
CAGATGCCTTCAGAATGTCTATCGCATGGCCAAGAATATTTCCCCATGGGAGAAAGGAGA  120
 T  D  A  F  R  M  S  I  A  W  P  R  I  F  P  H  G  R  K  E
AAGGGGTGAGTCAAGCTGGTGTGCAATTTTACCACGACCTTATCGACGAGCTCAAAAGAA  180
 K  G  V  S  Q  A  G  V  Q  F  Y  H  D  L  I  D  E  L  K  R
ATGGTATAACTCCGTTCGTGACAGTCTTTCACTGGGACACTCCACAAGATTTAGAGGACG  240
 N  G  I  T  P  F  V  T  V  F  H  W  D  T  P  Q  D  L  E  D
AATATGGTGGCTTTTTAAGTGAAAGGATTGTGAAAGATTTCCGAGAGTATGCAGATTTTG  300
 E  Y  G  G  F  L  S  E  R  I  V  K  D  F  R  E  Y  A  D  F
TTTTTCAAGAATATGGTGGAAAAGTGAAACATTGGATCACTTTCAACGAGCCATGGGTTT  360
 V  F  Q  E  Y  G  G  K  V  K  H  W  I  T  F  N  E  P  W  V
TCTCCCACGCTGGTTACGATGTAGGCAAGAAAGCACCAGGACGTTGCTCAAAGTACGTCA  420
 F  S  H  A  G  Y  D  V  G  K  K  A  P  G  R  C  S  K  Y  V
AAGAAGAATGTCATGATGGACGATCAGGATTCGAGGCTTACCTCGTCACCCACAATCTCC  480
 K  E  E  C  H  D  G  R  S  G  F  E  A  Y  L  V  T  H  N  L
TTAACTCTCACGCTGAAGCCGTTGAAGCTTTCCGACAGTGCGAAAAGTGTAAAGGTGGTA  540
 L  N  S  H  A  E  A  V  E  A  F  R  Q  C  E  K  C  K  G  G
AGATTGGTATCGCACATAGTCCGGCTTGGTTTGAGCCACATGACCTTGCTGATTCACAAG  600
 K  I  G  I  A  H  S  P  A  W  F  E  P  H  D  L  A  D  S  Q
ACGGTGCATCCATTGACCGTGCACTTGACTTTATTTTGGGATGGCATCTGGACACAACTA  660
 D  G  A  S  I  D  R  A  L  D  F  I  L  G  W  H  L  D  T  T
TGTATGGAGATTATCCGCAGATCATGAAAGATATTGTTGGACATAGATTGCCTAAATTTA  720
 M  Y  G  D  Y  P  Q  I  M  K  D  I  V  G  H  R  L  P  K  F
CCGAAGCACAGAAAGCAAAACTGAAAAACTCAGCCGATTTCGTCGGGCTCAACTATTATA  780
 T  E  A  Q  K  A  K  L  K  N  S  A  D  F  V  G  L  N  Y  Y
CTTCGATGTTTTCAAACCATCTGGAGAAGCCAGATCCTGCTAAACCAAGATGGATGCAAG  840
 T  S  M  F  S  N  H  L  E  K  P  D  P  A  K  P  R  W  M  Q
ATTCTCTTATTAACTGGGAAACTAAGAATGCGTACAATTACAGCATTGGTAGCAAGCCTA  900
 D  S  L  I  N  W  E  T  K  N  A  Y  N  Y  S  I  G  S  K  P
TCACCGGTGCACTTCCCGTTTTTGCCGAGAGGCTTTAGAAGTCTTTTGAAGTACATCAAGG  960
 I  T  G  A  L  P  V  F  A  R  G  F  R  S  L  L  K  Y  I  K
ATAAGTATGGCAACCCAGAAATTATGATCATGGAAAACGGATATGGAGAAGAACTTGGGG  1020
 D  K  Y  G  N  P  E  I  M  I  M  E  N  G  Y  G  E  E  L  G
CTGCAGATTCAATTGAAGTTGGTACAGCTGATCACAACAGGAAATATTATCTTCAGAGGC  1080
 A  A  D  S  I  E  V  G  T  A  D  H  N  R  K  Y  Y  L  Q  R
ATCTTTTGAGCATGAATGAAGCTATTTGCATCGACAAGGTGAATGTTACCGGATACTTTG  1140
 H  L  L  S  M  N  E  A  I  C  I  D  K  V  N  V  T  G  Y  F
TATGGTCCTTGTTGGATAACTTTGAGTGGCAAGATGGTTACAAGAACAGATTCGGACTCT  1200
 V  W  S  L  L  D  N  F  E  W  Q  D  G  Y  K  N  R  F  G  L
ACTACATTGATTTCAAGAATAACCTCACACGATACGAGAAAGAGTCAGGCAGGTACTACA  1260
 Y  Y  I  D  F  K  N  N  L  T  R  Y  E  K  E  S  G  R  Y  Y
AAGACTTCCTAAGTCAAGGTGTTCGTCCATCCATGATCAACAGAGATGAGCTTTGAGCTT  1320
 K  D  F  L  S  Q  G  V  R  P  S  M  I  N  R  D  E  L  .
ACATTTGGAGGATTCAATTTCATGTTTTCTTTCTTTTGTATCCATCCGTTTGTGATTGAC  1380
CAAGATCCATGAGGTCTTGCCGGAATT 1407
```

FIGURE 15

```
AATTCCCGGGTCGACCCACGCGTCCGAGAATTACAAACAAAAATGGTTTTGCAAAAGCTT  60
                                         M  V  L  Q  K  L
CCTCTCATTGGGCTGCTTTTGCTCCTGACCATCGTCGCCTCTCCAGCAAATGCAGATGGA 120
 P  L  I  G  L  L  L  L  T  I  V  A  S  P  A  N  A  D  G
CCTGTTTGCCCGCCGTCGAACAAACTAAGCCGGGCAAGTTTCCCTGAAGGTTTTTTATTT 180
 P  V  C  P  P  S  N  K  L  S  R  A  S  F  P  E  G  F  L  F
GGCACGGCTACTGCGGCATACCAGGTACCAAGGTTCGATTTAATGAAACTTGTTCGTGGA 240
 G  T  A  T  A  A  Y  Q  V  P  R  F  D  L  M  K  L  V  R  G
CCAGCCTTATGGGACATCTACTGTAGAAGATATCCAGAGAGGTGCAATAACGATAACGGC 300
 P  A  L  W  D  I  Y  C  R  R  Y  P  E  R  C  N  N  D  N  G
GATGTGGCCGTTGATTTCTTCCATCGTTATAAGGAAGATATCCAACTAATGAAGAATCTA 360
 D  V  A  V  D  F  F  H  R  Y  K  E  D  I  Q  L  M  K  N  L
AACACAGACGCCTTTAGAATGTCTATCGCATGGCCAAGAATATTTCCTCATGGGAGAAAG 420
 N  T  D  A  F  R  M  S  I  A  W  P  R  I  F  P  H  G  R  K
GAGAAAGGAGTGAGTCAAGCTGGTGTGCAATTCTACCACGACCTCATCGACGAGCTCATA 480
 E  K  G  V  S  Q  A  G  V  Q  F  Y  H  D  L  I  D  E  L  I
AAAAATGGTATAACTCCATTCGTTACTGTTTTTCACTGGGACACTCCACAAGATTTAGAA 540
 K  N  G  I  T  P  F  V  T  V  F  H  W  D  T  P  Q  D  L  E
GATGAATATGGCGGCTTTTTAAGCGAAAGGATTGTGAAGGATTTCCGAGAGTATGCAGAT 600
 D  E  Y  G  G  F  L  S  E  R  I  V  K  D  F  R  E  Y  A  D
TTTGTTTTCCAAGAATACGGTGGAAAAGTGAAACATTGGATCACTTTCAATGAGCCATGG 660
 F  V  F  Q  E  Y  G  G  K  V  K  H  W  I  T  F  N  E  P  W
GTTTTCTCGCACGCTGGCTATGACGTAGGCAAAAAGGCACCTGGTCGTTCCTCTTCTTAC 720
 V  F  S  H  A  G  Y  D  V  G  K  K  A  P  G  R  S  S  S  Y
GTCAATGCTAAATGCCAAGACGGACGATCAGGATACGAGGCTTACCTTGTCACTCACAAT 780
 V  N  A  K  C  Q  D  G  R  S  G  Y  E  A  Y  L  V  T  H  N
CTCCTTATCTCTCACGCAGAAGCAGTTGAAGCTTACCGGAAATGCGAAAAGTGTAAAGGT 840
 L  L  I  S  H  A  E  A  V  E  A  Y  R  K  C  E  K  C  K  G
GGGAAGATCGGAATTGCACATAGTCCTGCTTGGTTCGAAGCACATGACCTTGCTGATTCA 900
 G  K  I  G  I  A  H  S  P  A  W  F  E  A  H  D  L  A  D  S
CAAGACGGTGCGTCCATCGACCGTGCACTTGACTTTATTTTGGGATGGCATCTAGACACA 960
 Q  D  G  A  S  I  D  R  A  L  D  F  I  L  G  W  H  L  D  T
ACTACATTTGGAGATTATCCACAGATCATGAAAGACATTGTTGGACATAGATTGCCTAAA 1020
 T  T  F  G  D  Y  P  Q  I  M  K  D  I  V  G  H  R  L  P  K
TTTACAACTGAGCAGAAAGCAAAACTGAAAGCTTCTACCGATTTCGTTGGGCTCAACTAC 1080
 F  T  T  E  Q  K  A  K  L  K  A  S  T  D  F  V  G  L  N  Y
TATACTTCAGTGTTTTCAAACCATTTGGAGAAACCTGATCCTTCAAAACCAAGATGGATG 1140
 Y  T  S  V  F  S  N  H  L  E  K  P  D  P  S  K  P  R  W  M
CAAGATTCTCTTATTACATGGGAGTCTAAGAATGCGCAAAATTACGCCATTGGTAGCAAG 1200
 Q  D  S  L  I  T  W  E  S  K  N  A  Q  N  Y  A  I  G  S  K
CCTTTGACCGCTGCATTGAACGTTTACTCGAGAGGTTTTAGAAGTCTTTTGAAGTACATT 1260
 P  L  T  A  A  L  N  V  Y  S  R  G  F  R  S  L  L  K  Y  I
AAGGACAAATACGCAAATCCGGAAATTATGATCATGGAAAACGGATATGGAGAAGAACTA 1320
 K  D  K  Y  A  N  P  E  I  M  I  M  E  N  G  Y  G  E  E  L
GGGGCCTCAGATTCTGTTGCTGTTGGTACCGCTGATCATAACAGGAAATATTATCTTCAG 1380
 G  A  S  D  S  V  A  V  G  T  A  D  H  N  R  K  Y  Y  L  Q
AGGCATCTTTTGAGTATGCAAGAAGCTGTTTGCATCGACAAAGTGAATGTTACAGGATAC 1440
 R  H  L  L  S  M  Q  E  A  V  C  I  D  K  V  N  V  T  G  Y
TTTGTATGGTCATTGTTGGATAACTTCGAGTGGCAAGATGGTTACAAAAACAGATTTGGA 1500
 F  V  W  S  L  L  D  N  F  E  W  Q  D  G  Y  K  N  R  F  G
CTCTACTACGTTGATTTCAAAAATAACCTCACACGTTACGAGAAAGAATCCGGCAAGTAT 1560
 L  Y  Y  V  D  F  K  N  N  L  T  R  Y  E  K  E  S  G  K  Y
TACAAGGATTTCCTCAGTCAAGGTGTTCGTCCATCCGCGCTCAAGAAGGATGAGCTTTAA 1620
 Y  K  D  F  L  S  Q  G  V  R  P  S  A  L  K  K  D  E  L  .
GCTATTTCTGTTTCAATGTGTTTTTCCTATGTTTTACTTTGTGAGTGACCAAGATTCATG 1680

AGGTCTTGGTTCTAATAAAAAGAGTTTATTTTTCTTCTCATTTTTCATTGTCTACATGAT 1740

TTGCCAGATCTATAAGGCTCTGGTTATAATAAAATGATCCTTTGTGCCTAAAAAAAAAAA 1800

AAAAAAAAAAAAAAAAAAAAAAAAAGGGC 1829
```

```
PSR3.2     HSA---IGSMPLTAALPVYAKGFRKLLKYIKDRYANPEIMIMENGYGDHLGTTDSV-DVGTADHNRKYYLQRHLLAIHEA 458
PSR3.1A    NYA---IGSKPLTAALNVISRGFRSDLKYIKDRYANPEIMIMENGYCEELGASDSN-AVGTADHNRKYYLQRHLLSRGEA 455
PSR3.1B    NYS---IGSKPLTGALFPFRGFISDLKYIKDRYGNPEIMIMENGYCERGAADSI-EVGTADHNRKYYLQRHLLSQNEA 367
ATPyk10    NYA---IGSKPLTAALNVISRGFFSDLKYIKDRYANPEIMIMENGYCELGASDSN-AVGTADHNRKYYLQRHLLSQCEA 454
Bgl4       SVK---IGSQESNEKMAKYEALRKIVHYIERGNPEIIENGYGEKETDHSKALNDHNRKYIHDPHLLSLHQA 455
TRE104     K-P---IGFAASSWCIAPQEIDKHILVANHRNEVKYETENGRNSSTINMVTSRIPF· 425
pAH1       V-P---IGFKAASGWEVYPKCIHDEVLITEMYNIDLKYETENGVDEFNDPKISMEE-ALNCINRIDFYYRHICYLQAP 457
pCAS5      N-L---IGPQAYSSWFYIFPKCIEHFENITLATNDLVLYVTENCVDNYNNESQPIEE-ALQCDFRISGYKKLMWNALGS 449
PGR95      V-P---IGPQAASDWYKYPKCLYDEVLITENRYNIDIMYTENCMDEFNNPKIBLEQ-ALNISNRIDICYRHICYLQEA 449
BGQ60      V-P---IGPRANSDWRYIVPWRMNRAVIDVKERKCNETMILSENCMDQ--PGNVSIRE-EVHCTVRIRKYRDYITELKKA 449
MYR1       EFLGPLFVEDKVNGNSYYERPKCIYYVMDFFPTKYGDELKYVTENCFSTPSSENR-EQ--AIDLYKRIDYLCSHICFLRKV 463
TGG2       QPPGPPF-----SKGSYYHPRCMLNVMEHFRTKYGDELKYVTENCFSTCGEPIPFTE--AFHKVNRIDLCSHICFLRKA 454
AT-MYR     EAPGPPF-----NEASYYBPKCIYYVMDFRTTMGDELKYVTENCFSTPGDE-EFEK--AEVAYKRIDYLCSHICFLSKV 454

PSR3.2     ICIDKVRVTGYFVWSLLDNFEWQDGYKNRFGLYYVDFKNNLT-RYEKESAKYYKDFLAQGVRPSALKRDEI·   529
PSR3.1A    VCIDKVNVTGYFVWSLLDNFEWQDGYKNRFGLYYVDFKNNLT-RYEKESGKYYKDFISQGVRPSALKKDEI·   526
PSR3.1B    ICIDKVNVTGYFVWSLLDNFEWQDGYKNRFGLYYIDFKNNLT-RYEKESGRYYKDFISQGVRPSMINRDEI·   438
ATPyk10    VCIDKVNVTGYFVWSLLDNFEWQDGYKNRFGLYYVDFKNNLT-RYEKESGKYYKDFISQGVRPSALKKDEI·   524
Bgl4       ICEDKVNVTISYFVWSLMDNFELDGYTARFGLYIDFQNNLI-EMEKESATCSLNSSNRA·   514
TRE104                                                                    425
pAH1       EKK-GSKVKGYEAWSFLDNFEFDAGYTVRFGINMVDYNDNIK-EHSSLETYWFTSEIKKYBESTKEIQMFVESKLEHQKF 535
pCAS5      LKNYGVKLKGYEAWSYLDNFELNIGYTSRFGLYYVDYKNNLT-RYPKKSAHWFTKELNISVNANNIYELTSKDSRVGKF 528
PGR95      EIE-GANVCGYEAWSLLDNFEVSEGYTVRFGINMVDYDNGHK-EHSELETHWFRNELKRSSISKEKIRRCGNNNARARKF 527
BGQ60      EDN-GAFVAGYEAWSLLDNFEFRILGYTARFGIVVVDFNT--EK-RYPKDSALWFKNMESEKKES   509
MYR1       EKEKGVNVRGYEAELGDNYEFCKCFTVRFGISYVNWEDL-DDRNLKESGWYQREINGTVKNAVKQDFLRSSLSSQSQK 542
TGG2       EKEKRVNVKGYFVWSIGDNYEFCNGYTVRFGLSYVDENVTADEDLKAEGLWYQSEIRDTTKNQDILRSSEPFKNGDRKS 534
AT-MYR     EKEKNVNVKGYEAWSIGDNYEFCNGFTVRFGISYVDFAKITGDEDLRAEGRWFQKEINVTDEDETNQDLLRSSVSSKNRD 534

PSR3.2                                  529
PSR3.1A                                 526
PSR3.1B                                 438
ATPyk10                                 524
Bgl4                                    514
TRE104                                  425
pAH1       ESQMMNKVQSSLAVVV·            551
pCAS5      YVM·                          531
PGR95      VYRI·                        531
BGQ60                                   509
MYR1       KRFADA·                      548
TGG2       LTEND·                       539
AT-MYR     RKSLAD·                      540
```

FIGURE 17B

Name: *psr2*

Insert size: 950 bp mRNA size: 1.5 kb

Estimated protein size: 42 kD

T3)
```
AATTCCXXGGCAATGATCATGAATAAXCCTGTGAACTTCTTTGTGGTTGA 50
TGCGTTCACTGAGTCAXCTTTCAAAGGGAACCCAGCAGCAGTGTGCATTC 100
TTGAAGAGGATTATGAGAGAGACXACGCATGGCTTCAGTCTCTTXCCGCA 150
GAGTTTAACGTTTCTGAAACTTGTTTTGTGTXTCCCATTACTGGTCACGA 200
TGGTCXCXCCTCCGGTGGTTTACXCCTTCACTCGAGATGGATCTTTGTGG 250
TCATGGAACATTGGCATCTGCCTTATAGCCTCTTCCTCAAACGGXXGGTT 300
GATTCAGACAAGGCACGAGTTTXTAACACAATCAGGTATTCTTACAGGCC 350
```

T7)
```
AATTCCGGAGTCACAGCTTTTCCAGTGAGAAAAACTCTCTGCTCCTCCTT 50
ATCGtTAACGGAACCTTCgACTGTTCCACTCCTACACGAAGCCGAGTAAG 100
CTRcGAAATCACACTTGTTCATCTTGAGGCTCCAGTAATGTGCTAATGGA 150
CAATGTGCACTTCCACATACAGGGTCCTCATCCACTCCTAATCTGGGGGA 200
AAAGAACCGACTGCAGAAATCATACGCAGATCCTTCAGGAGCAGCAGCTG 250
TAACAATGATCAACTTTCGGGACATTTTGAAATTCA 286
```

FIGURE 18

Name: psr4

Clone No.: C53
Insert size: 0.8kb
mRNA size: 1.1kb
Estimated protein size: 32kD

T3)

```
AATTCCGGTTTTTTTTTTAATACATAAAAATGAAATTATTTTATTTCATT  50
TCATTGCAATACATTGCAGCATTTCATTTCATTACAATACATTXCAGCAT 100
TATGCATGCATGATGCATGACTAAGACCTGGTAACAGAAGTTACGACCAC 150
AATACTTTAAAACATAGAGACATACGCCTTATTATACCTTATTCATATTT 200
TTAGACCTTTTTCATGCATACACAAGCAAACATATTAGGTCATGACACAA 250
AACATAAAACAGCAGAACGGAAACACACCGTAACCAAACCAAGAAGGGAT 300
ACTTAATTTGTTTGAAATCGGAGTATTAAGGGTGACAGTGAGAGGGGTGA 350
CCAGTTCTCTGAATACCTTCCAGTTCAGCCGACGG 385
```

T7)

```
AATTCCGGTTTTTTTTTTTATACTCTCTACTCTTTGATATCCTAACAACAT  50
GGCAATGCTCGTCAGAAACAAAAACATAACCTTCTCACTGGTCTTGATAT 100
GTCTAATTGTGGTGTCTCCAGTGGCTAAGGCTCAACTTGATGGGCTTCTT 150
GGCAGGGATCCCAAAATCGTCAATATACAAGGGCGTATGATGTGCTCTAT 200
CGATGGTAATCCGAATTCCACTCCTCCAGTTGGTTCTCCCGTTATGCTTC 250
AGTGTGGTGGAAAAAATGTTGCAACTACGAATACGGTCGTTGGTGGAGGA 300
TTCTCGTCCTTCCGACACAGTGTCTACTATXCTTTCAGAACATCATCAAC 350
GA 352
```

FIGURE 19

Name: *psr5*

Clone No.: c28
Insert size: 1.9 kb
mRNA size: 1.4 kb
Estimated protein size: 40 kD

T3)

```
AATTCCGGAT CAAGAAAAGG TCTGAATCCA ATATCAAATA GAACATTTGC   50
AGAGATGACC ATGTATGTAG TCATGATTCA AAGGACAAAA CAATTGATTC  100
CAGACAAAAC AAAACGATGA TCACAACGTT ACGGCGAGGT GGCGCTGACG  150
TGACGGTGGC GTCCGTCGAG GCTCAGGTTG GCGTTGATGC TTGTCATGGT  200
ATTAAGATGG TCGCTGATAC TCTCCTCTCT GATATTACCG ATTCTGTTTT  250
CGACCTTATT GTGCTCCCCG GAXCTTCCCG XXXCGAGACT CTTAAAAACT  300
GTAAACTTTG GAGAATATGG TAAAGAAACA AGCACGAGAT GGACGACTTA  350
AAGACAAAAC  351
```

T7)

```
GATCGACGGT ATCGATAAGC TTGATATCGA ATXCCGGGCT CAACAGGAGA   50
TCATTTGCAC AGACCGTAGA GAATTTGTTC GCTCTATCTT TCTTGTCCAA  100
AGACGGACGA GTAGAGATCA TTGTTGATAA GAATGGCTCA CATTTTGCCT  150
TGCCGAGAAA CGCCACCAGC TGCGAACCTG GTGGCGTCAG GGGAAGTCAC  200
TTACAACCAC TTTGTGATTT AGATTCGATT CAAGACTGGA GATGATGTCT  250
GAAATGGTGC CGATGGGGGA AGAGCTAAGT TACCCACACA GAGAAA       296
```

FIGURE 20

Name: *psr6*

Clone No.: c44
Insert size: 1.0 kb
mRNA size: 2.3 kb
Estimated protein size: 64 kD

T3)

```
TTTTTTTTTTTTTXGTCTTTTTXTTTCCAGCAATTTAAGTTGTTTCTCGT   50
GTXAXTCCAGTGGTTGTACGGAATAGCCAAAGCAAACAAAGACCCGTCAT  100
GAAGAAGAATCCCATCATCTGAATXGCAAACCTTCCAATGACATCTATAC  150
ACXAACTGATGAACCAGTAACCAGA                            175
```

T7)

```
TCTCTTTTGGAGACAAACCAAAATTCCTGTGATGACCACGCTATGTTTCT   50
TTAGGTTTTGGCTAGGGTTTGGGATCGGTGGTGACTATCCTCTGTCCGCA  100
ACAATCATGTCTGAGTACGCTAACAAGAAAACTCGTGGAGCGTTCGTTTC  150
TGCGGTTTTCGCTATGCAAGGGTTTGGATCATGGCTGGTGGCACTTCGCT  200
ATAATCACTCCTCT                                       214
```

FIGURE 21

Name: *psr7*

Clone No.: c112
Insert size: ? kb
mRNA size: 1.5 kb
Estimated protein size: 36 kD

T3)

```
CTCCACCGCG GTGGCnnCGC TCTAGAACTA GTGGATCCCC CGGGCTGCAG   50
GTTTTTTTTT TTTTTTTTTT TGATTATATA TGATTTTATT ATTGAAACAA  100
AAAGCTCAGA GGATAGATTG TATCAGTCTT AAATAGAACT ACACATCACT  150
ATTTAAATAA ACnCCnGCGA CTTAACTGAA GAAnCGCCGG AAAATAAGAA  200
GAACAAAACA GGGAAGGAAG GTAGATGACT AGGTTAGCCT AATAAACAAA  250
ACTGCGGGCG   257
```

T7)

```
AATTCCGTTG AATCACGCCG CTTTGCTGAA GGATGAGCTC GACATTGTGA   50
TTCCTACCAT CCGTAACCTC GAGTTCCTCG AGATGTTGGA GGCCTCTTCT  100
CAGCTACATC TCATCATCGT CAGGACGGAG ATCTTAAGAC ATCGTGTTCT  150
GAAGGGTCGA TTACXAGCTC TACAACAGGA ACGACATTAC GATCTGGCCC  200
AAAGCTTCCT GCATTTCCTT CAAGGACTCT GCTTGT   236
```

FIGURE 22

**Name: *psr8***

Clone No.: c71
Insert size: 0.4 k
mRNA size: 1.5 kb
Estimated protein size: 42 kD

```
T3)
    CCTCCXCAAT XXCXXCGCTC TAGAACTAGT XXXTCCCCCG  40
    GGCTGCAGGA ATTCCGGATG TGATXGTCAT CTAGGAAGAA  80
    CGTAAATATG TGAAGAGTTT CGACAACAAC AGTCXXXGCA  120
    TATAGTAATC AAAAACTCTT TTTCAATCTA CCAAACAAAA  160
    CAAAATGAxX XCATAGGGAC XAAXCCCAGC CCATAAAGGA  200
    TCTCCACCTA GAGGCCAGAA AATTACT  227
```

FIGURE 23

Name: *psr9*

Clone No.: c100
Insert size: 1.6 kb
mRNA size: 2.6 and 1.7 kb
Estimated protein size: 72 and 47 kD

T3)

```
AATTCCGGCTTGGAGAAGAAGCACATCTGGACCCAGCTCTTCTTCGGCTC   50
TTAACCACTAGTGACTTCGCGTTTCTCGTCTCCACAAGATCATTCATGTA  100
CTGAACAACGGCCTGAGGGCCTTTTCGGCTATATCACGAGGAGGAACTTG  150
TAGCGGATTCTCCTGAGCACGAAACACACGCAGCTTCGTAAGCATTCTAA  200
AAGACTCAGGAAGAACACGGATCTGGTTATTGCTGATATCAAGCTCCTCG  250
AGCATCTCAAGGTTCCCTAACCGACCTCGGCAACGATATCATATCAGCAA  300
AGTTGTTCCCACAGCTTCACAAGCGAC  327
```

T7)

```
AATTCGCTGCAGCTGGATAAGCGTCTGGACACGACGGCAGCAAGTGGTGG   50
AAGAGATCGATGAGAATCCACAGATCTCTACCGCCGAGACCAGGCTCGAC  100
GAGGTCGAAGCCGCGAGGTCTCTGATACAGAACgtgGAGAAGGAAGACCA  150
ATCCTGGCTAGAAGccATTgCTAACcAGAGGAAACCCTCCGAGGTTCCCG  200
ACGAGCTATTCGCCGTGCTGCAGGAGATGAAGAGAGGTTCGTTCGGTTTC  250
GTAGCAAAGAGCAGATAAGAGAAGCCGCCAAGCTTCTCGATCTGGAAACG  300
GTCACTCTCACTTCGACGATTATCAGAGAGCTTCTGATTGCATTGCTTCT  350
CTTCTCGACGG  361
```

FIGURE 24

Name: *psr10*

Clone No.: c70
Insert size: 0.4 kb
mRNA size: 2.1 and 0.8 kb
Estimated protein size: 59 and 23 kD

T3)

```
ACCGCGGTGG CGCCGCTCTA GAACTAGTGG ATCCCCCGGG CTGCAGGTTT   50
TTTTTTTGTA TATAAGAAAA TGGTTGATTT ATATACATGA TTTACAACTA  100
GTAATTCCCC AAAAAATCAG CAGAGAGAAA AAGATATCGG AACAGGACTC  150
GATTGTTGAC CATGACCACT CGTCTCCATG GTCTTCATGG CGTCTCAGcC  200
CCCCCTAGCA CTTTAGTTTC TCTTGAA   227
```

T7)

```
TCAGCTCGCC GCCAAGATCC TAGGAAAGCT TTAGGGTTT TCGTGTCAGA   50
CTCTTCGTTT TTTTTTTTTT GGTTCACGAC CATCTTAAGA TCTTATTCTC  100
TTCTTTTCTT TGCCTTGGGC GAGCTTGATT ACGACGCATG TTGCGTTTTG  150
CTGTCTAAGT TTTTGATTCT CTTCAAAGTA AAAATAGTGA TACATTATAT  200
CTGGAAAGAA AACTAGTGAT TCCGATCT   228
```

FIGURE 25

Name: *psr11*

Clone No.: C59
Insert size: 0.8 kb
mRNA size: 4.1 and 1.1 kb
Estimated protein size: 115 and 32 kD T3)
```
AATTCCGGTT TTTTTCAATG AAATAACTGT ATGGTTAATA ACTTGATATA  50
GCAATATAGA GTCTAGACCA ACGTACAGTT TACAAAGAAA GAGAAGATGA  100
AAAGCAGTAC TTTGGGTTTC AGAACAAGGC TTTTATTGAA GGACCCTTTA  150
TTGAACCAAT ACCATAACCT ATAGGATCAA AGGCCTAAAA GAGAGGTAAG  200
CTTGTAGGGA AACGAACTTG CATCCACTGC TTCTCATACG TAACCAATGG  250
CTCCAGCCTA ACTCTCAGCA ACCAGTTCAT TGCAAGTTCT AGAGCG  296
```

T7)
```
AATTCCGGGG CAAGTCGACC TCCAGTTATT TCATTTCAAC AAATGTCTTT  50
CAACTCAGGC CACATTGAAC GAAGATTTAT GGAGGTACCA CTTGGGGCAA  100
CATGGGCTGA GGCTACGATG CGAACTTCGG GGTTTGATAC TACACGGAGA  150
TTTTATATTG ATGCGCTTCA GATTTGCCCG TTGAGAAGGC CTATCAAGTG  200
GGAGAACGCA ACAACATTTG CATCTCCATC TGCTAAAAGC TTTGCGTTTC  250
AGTGGTTAGT GGTCAAACGA TGGAACTAGC TCTAGCTCAA TCTGGGTCAG  300
TGGCTGGAGT GCAACCAAC  319
```

FIGURE 26

SEQUENCE LISTING

<160> NUMBER OF SEQ ID NOS: 48

<210> SEQ ID NO 1
<211> LENGTH: 1250
<212> TYPE: DNA
<213> ORGANISM: Aribidopsis Thaliana

<400> SEQUENCE: 1

```
ccacgcgtcc gagaagattc atcaaaaga aaaaaaaat aataaaggac cattttaggg      60
aagtgagaac aaaaacaaaa gtggtagcta tggagaagta tgagatggtg aaggatttag     120
gatttggtaa tttcggattg gctcggctta tccgtaataa gcaaacaaac gagcttgtgg     180
ctgtcaaatt catcgatcga ggctacaaga tagatgagaa cgttgcaaga gaaataatca     240
atcatagagc tctcaaccat ccgaatattg ttcggtttaa agaggttgtt ttaactccga     300
cacatcttgg aatagtaatg gagtatgcag ctggaggaga actgttcgag cggatatcta     360
gcgtgggtcg atttagcgaa cgtgaggcaa gatatttctt tcaacaactc atttgtggag     420
tccattactt acatgcattg caaatatgcc atagagatct gaaattagaa aacacattgc     480
ttgatggaag cccagcacca cgtttaaaaa tttgtgattt tggctactca aagtcttctg     540
ttctgcactc caacccaaaa tcaacggtgg gaactccggc atatatagca ccggaagttt     600
tttgtcgatc ggaatacgac ggaaagtcag ttgatgtgtg gtcttgtgga gtggccctct     660
atgttatgtt ggtaggagct tatccattcg aagaccctaa agaccctcgc aatttccgaa     720
aaactgttca gaaaataatg gccgtaaact acaagattcc aggatatgtt cacatatccg     780
aagactgcag aaagttacta tctcgtatat ttgttgccaa tccgttacat agaagtacgc     840
ttaaagagat taagagtcat gcatggttcc taaagaattt gccaagagaa ttaaaggagc     900
cagcacaagc aatctattac caaggaatg ttaatcttat taatttttct cctcaaagag      960
tagaggagat tatgaagata gttggtgagg caagaccgat tccaaacctt tctcgcccgg    1020
tcgaatcgct tggatcagat aaaaaagatg atgatgaaga agaatatttg gatgctaatg    1080
atgaagaatg gtatgatgat tacgcataga caataaaaat gtattatatg ttgtcaaatt    1140
```

-continued

```
atgaacggta cgaacatgaa cggtacgttc gtatttgtaa ttatctatat gaatttcggt    1200
ttttcttttt cataatcacc aaattagttt aaatgaaaaa aaaaaaaaaa              1250
```

<210> SEQ ID NO 2
<211> LENGTH: 339
<212> TYPE: PRT
<213> ORGANISM: Arabidopsis Thaliana

<400> SEQUENCE: 2

| Met | Glu | Lys | Tyr | Glu | Met | Val | Lys | Asp | Leu | Gly | Phe | Gly | Asn | Phe | Gly |
|---|---|---|---|---|---|---|---|---|---|---|---|---|---|---|---|
| 1 | | | | 5 | | | | | 10 | | | | | 15 | |

| Leu | Ala | Arg | Leu | Ile | Arg | Asn | Lys | Gln | Thr | Asn | Glu | Leu | Val | Ala | Val |
|---|---|---|---|---|---|---|---|---|---|---|---|---|---|---|---|
| | | | 20 | | | | | 25 | | | | | 30 | | |

| Lys | Phe | Ile | Asp | Arg | Gly | Tyr | Lys | Ile | Asp | Glu | Asn | Val | Ala | Arg | Glu |
|---|---|---|---|---|---|---|---|---|---|---|---|---|---|---|---|
| | | 35 | | | | | 40 | | | | | 45 | | | |

| Ile | Ile | Asn | His | Arg | Ala | Leu | Asn | His | Pro | Asn | Ile | Val | Arg | Phe | Lys |
|---|---|---|---|---|---|---|---|---|---|---|---|---|---|---|---|
| | 50 | | | | | 55 | | | | | 60 | | | | |

| Glu | Val | Val | Leu | Thr | Pro | Thr | His | Leu | Gly | Ile | Val | Met | Glu | Tyr | Ala |
|---|---|---|---|---|---|---|---|---|---|---|---|---|---|---|---|
| 65 | | | | | 70 | | | | | 75 | | | | | 80 |

| Ala | Gly | Gly | Glu | Leu | Phe | Glu | Arg | Ile | Ser | Ser | Val | Gly | Arg | Phe | Ser |
|---|---|---|---|---|---|---|---|---|---|---|---|---|---|---|---|
| | | | | 85 | | | | | 90 | | | | | 95 | |

| Glu | Arg | Glu | Ala | Arg | Tyr | Phe | Phe | Gln | Gln | Leu | Ile | Cys | Gly | Val | His |
|---|---|---|---|---|---|---|---|---|---|---|---|---|---|---|---|
| | | | 100 | | | | | 105 | | | | | 110 | | |

| Tyr | Leu | His | Ala | Leu | Gln | Ile | Cys | His | Arg | Asp | Leu | Lys | Leu | Glu | Asn |
|---|---|---|---|---|---|---|---|---|---|---|---|---|---|---|---|
| | | 115 | | | | | 120 | | | | | 125 | | | |

| Thr | Leu | Leu | Asp | Gly | Ser | Pro | Ala | Pro | Arg | Leu | Lys | Ile | Cys | Asp | Phe |
|---|---|---|---|---|---|---|---|---|---|---|---|---|---|---|---|
| | 130 | | | | | 135 | | | | | 140 | | | | |

| Gly | Tyr | Ser | Lys | Ser | Ser | Val | Leu | His | Ser | Asn | Pro | Lys | Ser | Thr | Val |
|---|---|---|---|---|---|---|---|---|---|---|---|---|---|---|---|
| 145 | | | | | 150 | | | | | 155 | | | | | 160 |

| Gly | Thr | Pro | Ala | Tyr | Ile | Ala | Pro | Glu | Val | Phe | Cys | Arg | Ser | Glu | Tyr |
|---|---|---|---|---|---|---|---|---|---|---|---|---|---|---|---|
| | | | | 165 | | | | | 170 | | | | | 175 | |

| Asp | Gly | Lys | Ser | Val | Asp | Val | Trp | Ser | Cys | Gly | Val | Ala | Leu | Tyr | Val |
|---|---|---|---|---|---|---|---|---|---|---|---|---|---|---|---|
| | | | 180 | | | | | 185 | | | | | 190 | | |

| Met | Leu | Val | Gly | Ala | Tyr | Pro | Phe | Glu | Asp | Pro | Lys | Asp | Pro | Arg | Asn |
|---|---|---|---|---|---|---|---|---|---|---|---|---|---|---|---|
| | | 195 | | | | | 200 | | | | | 205 | | | |

| Phe | Arg | Lys | Thr | Val | Gln | Lys | Ile | Met | Ala | Val | Asn | Tyr | Lys | Ile | Pro |
|---|---|---|---|---|---|---|---|---|---|---|---|---|---|---|---|
| | 210 | | | | | 215 | | | | | 220 | | | | |

| Gly | Tyr | Val | His | Ile | Ser | Glu | Asp | Cys | Arg | Lys | Leu | Leu | Ser | Arg | Ile |
|---|---|---|---|---|---|---|---|---|---|---|---|---|---|---|---|
| 225 | | | | | 230 | | | | | 235 | | | | | 240 |

| Phe | Val | Ala | Asn | Pro | Leu | His | Arg | Ser | Thr | Leu | Lys | Glu | Ile | Lys | Ser |
|---|---|---|---|---|---|---|---|---|---|---|---|---|---|---|---|
| | | | | 245 | | | | | 250 | | | | | 255 | |

| His | Ala | Trp | Phe | Leu | Lys | Asn | Leu | Pro | Arg | Glu | Leu | Lys | Glu | Pro | Ala |
|---|---|---|---|---|---|---|---|---|---|---|---|---|---|---|---|
| | | | 260 | | | | | 265 | | | | | 270 | | |

| Gln | Ala | Ile | Tyr | Tyr | Gln | Arg | Asn | Val | Asn | Leu | Ile | Asn | Phe | Ser | Pro |
|---|---|---|---|---|---|---|---|---|---|---|---|---|---|---|---|
| | | 275 | | | | | 280 | | | | | 285 | | | |

| Gln | Arg | Val | Glu | Glu | Ile | Met | Lys | Ile | Val | Gly | Glu | Ala | Arg | Pro | Ile |
|---|---|---|---|---|---|---|---|---|---|---|---|---|---|---|---|
| | 290 | | | | | 295 | | | | | 300 | | | | |

| Pro | Asn | Leu | Ser | Arg | Pro | Val | Glu | Ser | Leu | Gly | Ser | Asp | Lys | Lys | Asp |
|---|---|---|---|---|---|---|---|---|---|---|---|---|---|---|---|
| 305 | | | | | 310 | | | | | 315 | | | | | 320 |

| Asp | Asp | Glu | Glu | Glu | Tyr | Leu | Asp | Ala | Asn | Asp | Glu | Glu | Trp | Tyr | Asp |
|---|---|---|---|---|---|---|---|---|---|---|---|---|---|---|---|
| | | | | 325 | | | | | 330 | | | | | 335 | |

Asp Tyr Ala

<210> SEQ ID NO 3

-continued

```
<211> LENGTH: 912
<212> TYPE: DNA
<213> ORGANISM: Brassica Nigra

<400> SEQUENCE: 3
cggcggatat caagcgcggg tcgattcagc gaagctgagg ctagatattt ctttcaacaa      60
ctcatttgcg gagtgcatta cttacatgca atgcaaatat gccatagaga tctgaaatta     120
gaaaacattt tgcttgatgg aagtccagca ccccgtctaa aaatttgtga ttttggctac     180
tcgaagtctt ctattctgca ttcaaaccct aaatcaacgg tggggacccc ggcatatata     240
gcaccggaag ttttggtcg ttcggaatac gacgggaagt ctgttgatgt gtggtcttct      300
ggagtggcac tctatgttat attggtagga gcttacccct tcgaagaccc gaaagatcct     360
cgcaatttcc gaaaaactgt ccagaaaata atggctgtta agtacaagat tcaaggatat     420
gttcacatat ctgaagattg caggaactta ttatctcgta tatatgttgc caatccatca     480
catagaatta cgcctatcat agagattagg agtcatgcat ggttcctaaa gaatttgcca     540
agagaactaa aggagtccgc acaagcagtc tattatcaaa ggaatgttaa tcttattaac     600
ctttctcctc aaagggtaga ggagattatg aagatactgg gtaaggcaag aaaccattcc     660
agacctttca cgcccactcg atcccatgga aatggtgaaa agatgatgt agatgctgaa      720 gaagaagaat atttggatgc taatgatgaa gaatgtgatg atgaatatcc atagacaaaa     780
atattactaa tgttgtgaaa ttatgagaag tacttgtaat tttattttttg aatttcggtt    840 aaagttatta agtaagaga acataacaaa ttaaaataaa atttattttg agtaccaaaa      900
aaaaaaaaaa aa                                                         912

<210> SEQ ID NO 4
<211> LENGTH: 256
<212> TYPE: PRT
<213> ORGANISM: Brassica nigra

<400> SEQUENCE: 4

Arg Ile Ser Ser Ala Gly Arg Phe Ser Glu Ala Glu Ala Arg Tyr Phe
 1               5                  10                  15

Phe Gln Gln Leu Ile Cys Gly Val His Tyr Leu His Ala Met Gln Ile
                20                  25                  30

Cys His Arg Asp Leu Lys Leu Glu Asn Ile Leu Leu Asp Gly Ser Pro
            35                  40                  45

Ala Pro Arg Leu Lys Ile Cys Asp Phe Gly Tyr Ser Lys Ser Ser Ile
        50                  55                  60

Leu His Ser Asn Pro Lys Ser Thr Val Gly Thr Pro Ala Tyr Ile Ala
65                  70                  75                  80

Pro Glu Val Phe Gly Arg Ser Glu Tyr Asp Gly Lys Ser Val Asp Val
                85                  90                  95

Trp Ser Ser Gly Val Ala Leu Tyr Val Ile Leu Val Gly Ala Tyr Pro
            100                 105                 110

Phe Glu Asp Pro Lys Asp Pro Arg Asn Phe Arg Lys Thr Val Gln Lys
        115                 120                 125

Ile Met Ala Val Lys Tyr Lys Ile Gln Gly Tyr Val His Ile Ser Glu
    130                 135                 140

Asp Cys Arg Asn Leu Leu Ser Arg Ile Tyr Val Ala Asn Pro Ser His
145                 150                 155                 160

Arg Ile Thr Pro Ile Ile Glu Ile Arg Ser His Ala Trp Phe Leu Lys
                165                 170                 175
```

```
Asn Leu Pro Arg Glu Leu Lys Glu Ser Ala Gln Ala Val Tyr Tyr Gln
            180                 185                 190

Arg Asn Val Asn Leu Ile Asn Leu Ser Pro Gln Arg Val Glu Glu Ile
        195                 200                 205

Met Lys Ile Leu Gly Lys Ala Arg Thr Ile Pro Asp Leu Ser Arg Pro
    210                 215                 220

Leu Glu Ser His Gly Asn Gly Glu Lys Asp Asp Val Asp Ala Glu Glu
225                 230                 235                 240

Glu Glu Tyr Leu Asp Ala Asn Asp Glu Glu Cys Asp Asp Glu Tyr Pro
            245                 250                 255

<210> SEQ ID NO 5
<211> LENGTH: 3781
<212> TYPE: DNA
<213> ORGANISM: Arabidopsis Thaliana

<400> SEQUENCE: 5
```

| | | | | | |
|---|---|---|---|---|---|
| aatcatcata | aacttgttct | cttccagaag | aaactaaaaa | caaaaatggc | attgcaaaag | 60 |
| tttcctctca | tggggctgct | tttgctccta | accatcctcg | tctctgtgac | aacagcggtt | 120 |
| gatgatcctg | tttgcccggc | gacttccaag | ctaagccgag | caagtttccc | taatgggttt | 180 |
| ttgtttggca | cggctactgc | tgcgtttcag | gtacaacaga | tttactaaat | catagttcaa | 240 |
| aaaacaaaaa | gtagtgtcgt | tattgtgttt | ctatctgaat | tcaaatccat | attttttaaaa | 300 |
| tatggttttt | ttttatgtaa | aagttgctca | aaatatgtta | tacctatcat | ttgaaatcat | 360 |
| ttgtgcatgt | gatattcctc | aactcatcaa | ctattttttg | ttatgtcatt | aggtcgaagg | 420 |
| tgcaattaat | gaaacttgtc | gtggaccggc | tctatgggat | atctactgta | aagaaatcc | 480 |
| aggtgagtgt | actcgtataa | tctacattct | caatacagta | tgtttaaata | ttaaattaaa | 540 |
| tttaactaat | taatatcaat | acatagccat | taattttctt | aattactttc | aaattacaga | 600 |
| gagatgtagt | ggcgaccacg | ccgatgtggc | cgttgatttc | ttccatcgtt | ataaggtata | 660 |
| tattaatata | aatttaagac | aaacataact | tatattctcg | agatgttatt | gaaattttgc | 720 |
| cttgtcttaa | aaatgtttgt | aggaagatat | tcagctaatg | aagaatctaa | acacagatgc | 780 |
| attcagactc | tcaatcgcat | ggtcaagaat | atttcctcgt | gagtatatgt | ctgcagatct | 840 |
| ctagtttgat | tttgttttaa | tcgaatttgg | tgaaattaga | tttatgtgat | tgttatataa | 900 |
| tactaataac | caatgaattt | agatgatgta | tatgtgaatg | ttgaagtatc | aataactaat | 960 |
| gaaacaaact | gtaatgcttt | attagatggg | agaaaggaga | agggagtgag | tcaagctggt | 1020 |
| gtgcaattct | accacgagct | catcgatgaa | ctccttaaaa | atggttatat | acatataaaa | 1080 |
| tacctagttc | acaaaaatac | aagtaatata | gtatccttat | ttaacatttc | tttctatttt | 1140 |
| acgtcataaa | taggtatagt | tccgtttgtg | actgttttcc | attgggacac | tccacaagat | 1200 |
| ttggaagacg | aaatatggcgg | tttcttaagc | caaaacattg | tgtatgtttt | tgtaaattaa | 1260 |
| acaaaataca | tttagttaag | tttatatgga | aattattaat | ttggtatctt | ttttttttgc | 1320 |
| aaaaatacag | gaaagatttt | cgagaatatg | cagattatgt | tttcactgaa | tacggtggaa | 1380 |
| aagtgaaaaa | ctggatcact | ttcaacgagc | catgggtctt | tgctcacgca | ggttacgact | 1440 |
| taggaaagaa | agcaccagga | cgttgttctc | gctacgttcc | aggttgcgaa | gaccgagagg | 1500 |
| gacaatctgg | taaagaggct | tatctagtca | gtcacaatct | cctcaacgct | cacgcagaag | 1560 |
| ctgttgaagt | tttccgccaa | aagtagtttt | acattagata | taaatcataa | ttaattatca | 1620 |
| ggtcacatta | gatataaatc | acaattaatt | atcaggtttc | gaatcttaaa | ataggttgtt | 1680 |

-continued

```
ttgtgttgtg tttatggaca taggttaaag gtgggaaaat cggaatcgca catagtccgg    1740
cttggttcga accacatgat cttaaagatt caaatgacgc tccaactgtt agccgtgtac    1800
ttgactttat gttgggatgg taagtatata ttatgttaga aaatggtttc tcgtatataa    1860
tttcataaaa attaatgtag ttattaattt tgtgtaggca tctggagcca actacttcgg    1920
gagattatcc acaaatcatg aaagaccttc ttggttacag attgcctcaa tttactgctg    1980
cacaaaaagc aaaattgaaa gattcgaccg atttcgtagg cttaactac tatacttcga    2040 cattttcaaa ttataatgag aagccagatc cgtctaaacc aagttggaag caagattctc    2100
ttgtttcctg ggaacgtaag tttttttttg ttttccgtac atgaaaccaa accagaaaac    2160
taaagataaa aggttttata atactaattg atatgcatac atttttcactt tttatttttc    2220 agctaagaat gtagatcaca gcgccattgg tagcatggta agcgtttgat taaactagtc    2280
ctagtttgat tgttaatttt tgtctacgac ataacatttt caccattgct ttatttcagc    2340
ctcttactgc tgcattgccc gtctacgcta aaggatttag aaagctttta aagtacatca    2400
aggacaaata cgcaaacccg gagattatga taatggaaaa tggtaactcg agatttattg    2460
ttatatttgt gtgttgattt aatcttaact cttaagagta atatactgat cattataatg    2520 ttgtttttc taggatatgg agataaactt gggaccacag attcggttga cgttggtact    2580
gctgatcata acaggaaata ttatcttcag aggcatcttc tggctatgaa cgaggctatt    2640
tggtaagcct tttattattt gatagattga ctaacgattc tattgaatgg tctaattaag    2700
aacataattg tgtttgtgca gcatcgataa ggtgagagtt acgggatact ttgtatggtc    2760
attgttggat aacttcgaat ggcaagatgg ttacaaaaac agattcggac tctattacgt    2820
cgatttcaaa ataaccctca cacgttatga gaaagaatca gccaagtatt acaaagattt    2880
cctcgctcaa ggtgttcgtc catccgcact caagagggat gagctttaag ttatattttg    2940
aggatttcgt tttctattcg atgttttcc tatgttttag tttgtgattg accacgcacg    3000
attcatgagt cgtggttaat aataataaaa gtgtttcgtt ttccttcaat ctctagctta    3060
ttcgacaaga tcaaagaagg ctttagtttt aatgacgtta tccttttga gaatcaatat    3120 gtgaagttaa atatgtttta ccttccaaac ttgaagaaaa attgaatcat acaaccttaa    3180
cattaaaaaa tttatgagtt acaaaatgat gtaagaaaat atcattagtt ttagaaaatt    3240
aaaaatacga atttacctct atacatagaa atagattagg aaataatttg acgtcgtctt    3300
aacaactaag tacaaacatt tcaaaaacta acaacttaaa cgttggcgat gaaataaaca    3360
atggcaattc attttcccaa acagttctaa tatttatttt ttgaaagtca ctagtttaga    3420
ttaaaaaaca ggacgaccag caagagaaga tatctctttt tcactcattt ggccaagcgt    3480
attttctata taccttaagg aaataaaatc catgcatgat gcaaccaaat aaatccacca    3540
tgcaatacca acatcattca ttactttgga aattcatatt tcattcttag caagcaaaaa    3600
aaaacaaaaa aaaacaatca aacgtatgtg ttaataatga aatcatcaca ttctatctta    3660
ctagtagtca cttatcaaaa acgatttatg taaatagtga ttttcaagat tttttttta    3720 aaagcaaaaa atttaaaggc caactcactt tcagactgtt tcttttgtaa aattgagaat    3780
t                                                                    3781
```

<210> SEQ ID NO 6
<211> LENGTH: 528
<212> TYPE: PRT
<213> ORGANISM: Arabidopsis Thaliana

<400> SEQUENCE: 6

-continued

```
Met Ala Leu Gln Lys Phe Pro Leu Met Gly Leu Leu Leu Leu Thr
 1               5                   10                  15

Ile Leu Val Ser Val Thr Thr Ala Val Asp Asp Pro Val Cys Pro Ala
            20                  25                  30

Thr Ser Lys Leu Ser Arg Ala Ser Phe Pro Asn Gly Phe Leu Phe Gly
            35                  40                  45

Thr Ala Thr Ala Ala Phe Gln Val Glu Gly Ala Ile Asn Glu Thr Cys
        50                  55                  60

Arg Gly Pro Ala Leu Trp Asp Ile Tyr Cys Arg Arg Asn Pro Gly Glu
65                  70                  75                  80

Cys Thr Gln Arg Cys Ser Gly Asp His Ala Asp Val Ala Val Asp Phe
                85                  90                  95

Phe His Arg Tyr Lys Glu Asp Ile Gln Leu Met Lys Asn Leu Asn Thr
                100                 105                 110

Asp Ala Phe Arg Leu Ser Ile Ala Trp Ser Arg Ile Phe Pro His Gly
            115                 120                 125

Arg Lys Glu Lys Gly Val Ser Gln Ala Gly Val Gln Phe Tyr His Glu
            130                 135                 140

Leu Ile Asp Glu Leu Leu Lys Asn Gly Ile Val Pro Phe Val Thr Val
145                 150                 155                 160

Phe His Trp Asp Thr Pro Gln Asp Leu Glu Asp Glu Tyr Gly Gly Phe
                165                 170                 175

Leu Ser Gln Asn Ile Val Lys Asp Phe Arg Glu Tyr Ala Asp Tyr Val
            180                 185                 190

Phe Thr Glu Tyr Gly Gly Lys Val Lys Asn Trp Ile Thr Phe Asn Glu
            195                 200                 205

Pro Trp Val Phe Ala His Ala Gly Tyr Asp Leu Gly Lys Lys Ala Pro
210                 215                 220

Gly Arg Cys Ser Arg Tyr Val Pro Gly Cys Glu Asp Arg Glu Gly Gln
225                 230                 235                 240

Ser Gly Lys Glu Ala Tyr Leu Val Ser His Asn Leu Leu Asn Ala His
                245                 250                 255

Ala Glu Ala Val Glu Val Phe Arg Gln Lys Val Lys Gly Gly Lys Ile
                260                 265                 270

Gly Ile Ala His Ser Pro Ala Trp Phe Glu Pro His Asp Leu Lys Asp
            275                 280                 285

Ser Asn Asp Ala Pro Thr Val Ser Arg Val Leu Asp Phe Met Leu Gly
            290                 295                 300

Trp His Leu Glu Pro Thr Thr Ser Gly Asp Tyr Pro Gln Ile Met Lys
305                 310                 315                 320

Asp Leu Leu Gly Tyr Arg Leu Pro Gln Phe Thr Ala Ala Gln Lys Ala
                325                 330                 335

Lys Leu Lys Asp Ser Thr Asp Phe Val Gly Leu Asn Tyr Tyr Thr Ser
                340                 345                 350

Thr Phe Ser Asn Tyr Asn Glu Lys Pro Asp Pro Ser Lys Pro Ser Trp
            355                 360                 365

Lys Gln Asp Ser Leu Val Ser Trp Glu Pro Lys Asn Val Asp His Ser
            370                 375                 380

Ala Ile Gly Ser Met Pro Leu Thr Ala Ala Leu Pro Val Tyr Ala Lys
385                 390                 395                 400

Gly Phe Arg Lys Leu Leu Lys Tyr Ile Lys Asp Lys Tyr Ala Asn Pro
                405                 410                 415
```

```
Glu Ile Met Ile Met Glu Asn Gly Tyr Gly Asp Lys Leu Gly Thr Thr
                420                 425                 430

Asp Ser Val Asp Val Gly Thr Ala Asp His Asn Arg Lys Tyr Tyr Leu
            435                 440                 445

Gln Arg His Leu Leu Ala Met Asn Glu Ala Ile Cys Ile Asp Lys Val
        450                 455                 460

Arg Val Thr Gly Tyr Phe Val Trp Ser Leu Leu Asp Asn Phe Glu Trp
465                 470                 475                 480

Gln Asp Gly Tyr Lys Asn Arg Phe Gly Leu Tyr Tyr Val Asp Phe Lys
                485                 490                 495

Asn Asn Leu Thr Arg Tyr Glu Lys Glu Ser Ala Lys Tyr Tyr Lys Asp
            500                 505                 510

Phe Leu Ala Gln Gly Val Arg Pro Ser Ala Leu Lys Arg Asp Glu Leu
        515                 520                 525

<210> SEQ ID NO 7
<211> LENGTH: 1407
<212> TYPE: DNA
<213> ORGANISM: Brassica Nigra

<400> SEQUENCE: 7
ccggcgttga tttcttccat cgttataagg aagatatcca acttatgaag aatctaaaca      60
cagatgcctt cagaatgtct atcgcatggc caagaatatt tccccatggg agaaaggaga    120 aagggggtgag tcaagctggt gtgcaatttt accacgacct tatcgacgag ctcaaaagaa   180
atggtataac tccgttcgtg acagtctttc actgggacac tccacaagat ttagaggacg    240
aatatggtgg cttttttaagt gaaggattg tgaaagattt ccgagagtat gcagattttg    300
tttttcaaga atatggtgga aaagtgaaac attggatcac tttcaacgag ccatgggttt    360
tctcccacgc tggttacgat gtaggcaaga agcaccagg acgttgctca agtacgtca     420 aagaagaatg tcatgatgga cgatcaggat tcgaggctta cctcgtcacc cacaatctcc    480
ttaactctca cgctgaagcc gttgaagctt tccgacagtg cgaaaagtgt aaaggtggta    540
agattggtat cgcacatagt ccggcttggt ttgagccaca tgaccttgct gattcacaag    600
acggtgcatc cattgaccgt gcacttgact ttatttttggg atggcatctg acacaacta    660 tgtatggaga ttatccgcag atcatgaaag atattgttgg acatagattg cctaaattta    720
ccgaagcaca gaaagcaaaa ctgaaaaaact cagccgattt cgtcgggctc aactattata   780
cttcgatgtt ttcaaaccat ctggagaagc cagatcctgc taaaccaaga tggatgcaag    840
attctcttat taactgggaa actaagaatg cgtacaatta cagcattggt agcaagccta    900
tcaccggtgc acttcccgtt tttgcgagag ctttagaag tcttttgaag tacatcaagg    960
ataagtatgg caacccagaa attatgatca tggaaaacgg atatggagaa gaacttgggg   1020
ctgcagattc aattgaagtt ggtacagctg atcacaacag gaaatattat cttcagaggc   1080
atcttttgag catgaatgaa gctatttgca tcgacaaggt gaatgttacc ggatactttg   1140
tatggtcctt gttggataac tttgagtggc aagatggtta caagaacaga ttcggactct   1200
actacattga tttcaagaat aacctcacac gatacgagaa agagtcaggc aggtactaca   1260
aagacttcct aagtcaaggt gttcgtccat ccatgatcaa cagagatgag ctttgagctt   1320
acatttggag gattcaattt catgtttttct ttcttttgta tccatccgtt tgtgattgac   1380
caagatccat gaggtcttgc cggaatt                                         1407

<210> SEQ ID NO 8
```

<211> LENGTH: 437
<212> TYPE: PRT
<213> ORGANISM: Brassica Nigra

<400> SEQUENCE: 8

```
Gly Val Asp Phe Phe His Arg Tyr Lys Glu Asp Ile Gln Leu Met Lys
 1               5                  10                  15

Asn Leu Asn Thr Asp Ala Phe Arg Met Ser Ile Ala Trp Pro Arg Ile
            20                  25                  30

Phe Pro His Gly Arg Lys Glu Lys Gly Val Ser Gln Ala Gly Val Gln
        35                  40                  45

Phe Tyr His Asp Leu Ile Asp Glu Leu Lys Arg Asn Gly Ile Thr Pro
    50                  55                  60

Phe Val Thr Val Phe His Trp Asp Thr Pro Gln Asp Leu Glu Asp Glu
65                  70                  75                  80

Tyr Gly Gly Phe Leu Ser Glu Arg Ile Val Lys Asp Phe Arg Glu Tyr
                85                  90                  95

Ala Asp Phe Val Phe Gln Glu Tyr Gly Gly Lys Val Lys His Trp Ile
            100                 105                 110

Thr Phe Asn Glu Pro Trp Val Phe Ser His Ala Gly Tyr Asp Val Gly
        115                 120                 125

Lys Lys Ala Pro Gly Arg Cys Ser Lys Tyr Val Lys Glu Glu Cys His
    130                 135                 140

Asp Gly Arg Ser Gly Phe Glu Ala Tyr Leu Val Thr His Asn Leu Leu
145                 150                 155                 160

Asn Ser His Ala Glu Ala Val Glu Ala Phe Arg Gln Cys Glu Lys Cys
                165                 170                 175

Lys Gly Gly Lys Ile Gly Ile Ala His Ser Pro Ala Trp Phe Glu Pro
            180                 185                 190

His Asp Leu Ala Asp Ser Gln Asp Gly Ala Ser Ile Asp Arg Ala Leu
        195                 200                 205

Asp Phe Ile Leu Gly Trp His Leu Asp Thr Thr Met Tyr Gly Asp Tyr
    210                 215                 220

Pro Gln Ile Met Lys Asp Ile Val Gly His Arg Leu Pro Lys Phe Thr
225                 230                 235                 240

Glu Ala Gln Lys Ala Lys Leu Lys Asn Ser Ala Asp Phe Val Gly Leu
                245                 250                 255

Asn Tyr Tyr Thr Ser Met Phe Ser Asn His Leu Glu Lys Pro Asp Pro
            260                 265                 270

Ala Lys Pro Arg Trp Met Gln Asp Ser Leu Ile Asn Trp Glu Thr Lys
        275                 280                 285

Asn Ala Tyr Asn Tyr Ser Ile Gly Ser Lys Pro Ile Thr Gly Ala Leu
    290                 295                 300

Pro Val Phe Ala Arg Gly Phe Arg Ser Leu Leu Lys Tyr Ile Lys Asp
305                 310                 315                 320

Lys Tyr Gly Asn Pro Glu Ile Met Ile Met Glu Asn Gly Tyr Gly Glu
                325                 330                 335

Glu Leu Gly Ala Ala Asp Ser Ile Glu Val Gly Thr Ala Asp His Asn
            340                 345                 350

Arg Lys Tyr Tyr Leu Gln Arg His Leu Leu Ser Met Asn Glu Ala Ile
        355                 360                 365

Cys Ile Asp Lys Val Asn Val Thr Gly Tyr Phe Val Trp Ser Leu Leu
    370                 375                 380

Asp Asn Phe Glu Trp Gln Asp Gly Tyr Lys Asn Arg Phe Gly Leu Tyr
```

```
385                 390                 395                 400
Tyr Ile Asp Phe Lys Asn Asn Leu Thr Arg Tyr Glu Lys Glu Ser Gly
                    405                 410                 415

Arg Tyr Tyr Lys Asp Phe Leu Ser Gln Gly Val Arg Pro Ser Met Ile
            420                 425                 430

Asn Arg Asp Glu Leu
        435
```

<210> SEQ ID NO 9
<211> LENGTH: 1829
<212> TYPE: DNA
<213> ORGANISM: Arabidopsis Thaliana

<400> SEQUENCE: 9

| | | | | | |
|---|---|---|---|---|---|
| aattcccggg | tcgacccacg | cgtccgagaa | ttacaaacaa | aaatggtttt | gcaaaagctt | 60 |
| cctctcattg | ggctgctttt | gctcctgacc | atcgtcgcct | ctccagcaaa | tgcagatgga | 120 |
| cctgtttgcc | cgccgtcgaa | caaactaagc | cgggcaagtt | ccctgaagg | tttttatt | 180 |
| ggcacggcta | ctgcggcata | ccaggtacca | aggttcgatt | taatgaaact | tgttcgtgga | 240 |
| ccagccttat | gggacatcta | ctgtagaaga | tatccagaga | ggtgcaataa | cgataacggc | 300 |
| gatgtggccg | ttgatttctt | ccatcgttat | aaggaagata | tccaactaat | gaagaatcta | 360 |
| aacacagacg | cctttagaat | gtctatcgca | tggccaagaa | tatttcctca | tgggagaaag | 420 |
| gagaaaggag | tgagtcaagc | tggtgtgcaa | ttctaccacg | acctcatcga | cgagctcata | 480 |
| aaaaatggta | taactccatt | cgttactgtt | tttcactggg | acactccaca | agatttagaa | 540 |
| gatgaatatg | gcggcttttt | aagcgaaagg | attgtgaagg | atttccgaga | gtatgcagat | 600 |
| tttgttttcc | aagaatacgg | tggaaaagtg | aaacattgga | tcactttcaa | tgagccatgg | 660 |
| gttttctcgc | acgctggcta | tgacgtaggc | aaaaaggcac | ctggtcgttc | ctcttcttac | 720 |
| gtcaatgcta | aatgccaaga | cggacgatca | ggatacgagg | cttaccttgt | cactcacaat | 780 |
| ctccttatct | ctcacgcaga | agcagttgaa | gcttaccgga | aatgcgaaaa | gtgtaaaggt | 840 |
| gggaagatcg | gaattgcaca | tagtcctgct | tggttcgaag | cacatgacct | tgctgattca | 900 |
| caagacggtg | cgtccatcga | ccgtgcactt | gactttattt | tgggatggca | tctagacaca | 960 |
| actacatttg | gagattatcc | acagatcatg | aaagacattg | ttggacatag | attgcctaaa | 1020 |
| tttacaactg | agcagaaagc | aaaactgaaa | gcttctaccg | atttcgttgg | gctcaactac | 1080 |
| tatacttcag | tgttttcaaa | ccatttggag | aaacctgatc | cttcaaaacc | aagatggatg | 1140 |
| caagattctc | ttattacatg | gggagtctaag | aatgcgcaaa | attacgccat | tggtagcaag | 1200 |
| cctttgaccg | ctgcattgaa | cgtttactcg | agaggtttta | gaagtctttt | gaagtacatt | 1260 |
| aaggacaaat | acgcaaatcc | ggaaattatg | atcatggaaa | acggatatgg | agaagaacta | 1320 |
| ggggcctcag | attctgttgc | tgttggtacc | gctgatcata | caggaaata | ttatcttcag | 1380 |
| aggcatcttt | tgagtatgca | agaagctgtt | tgcatcgaca | aagtgaatgt | tacaggatac | 1440 |
| tttgtatggt | cattgttgga | taacttcgag | tggcaagatg | gttacaaaaa | cagatttgga | 1500 |
| ctctactacg | ttgatttcaa | aaataacctc | acacgttacg | agaaagaatc | cggcaagtat | 1560 |
| tacaaggatt | tcctcagtca | aggtgttcgt | ccatccgcgc | tcaagaagga | tgagctttaa | 1620 |
| gctatttctg | tttcaatgtg | ttttttcctat | gttttacttt | gtgagtgacc | aagattcatg | 1680 |
| aggtcttggt | tctaataaaa | agagtttatt | tttcttctca | tttttcattg | tctacatgat | 1740 |
| ttgccagatc | tataaggctc | tggttataat | aaaatgatcc | tttgtgccta | aaaaaaaaaa | 1800 | aaaaaaaaaa aaaaaaaaaa aaaaagggc                                    1829

<210> SEQ ID NO 10
<211> LENGTH: 525
<212> TYPE: PRT
<213> ORGANISM: Arabidoppsis Thaliana

<400> SEQUENCE: 10

Met Val Leu Gln Lys Leu Pro Leu Ile Gly Leu Leu Leu Leu Leu Thr
1               5                   10                  15

Ile Val Ala Ser Pro Ala Asn Ala Asp Gly Pro Val Cys Pro Pro Ser
            20                  25                  30

Asn Lys Leu Ser Arg Ala Ser Phe Pro Glu Gly Phe Leu Phe Gly Thr
        35                  40                  45

Ala Thr Ala Ala Tyr Gln Val Pro Arg Phe Asp Leu Met Lys Leu Val
    50                  55                  60

Arg Gly Pro Ala Leu Trp Asp Ile Tyr Cys Arg Tyr Pro Glu Arg
65                  70                  75                  80

Cys Asn Asn Asp Asn Gly Asp Val Ala Val Asp Phe Phe His Arg Tyr
                85                  90                  95

Lys Glu Asp Ile Gln Leu Met Lys Asn Leu Asn Thr Asp Ala Phe Arg
            100                 105                 110

Met Ser Ile Ala Trp Pro Arg Ile Phe Pro His Gly Arg Lys Glu Lys
        115                 120                 125

Gly Val Ser Gln Ala Gly Val Gln Phe Tyr His Asp Leu Ile Asp Glu
    130                 135                 140

Leu Ile Lys Asn Gly Ile Thr Pro Phe Val Thr Val Phe His Trp Asp
145                 150                 155                 160

Thr Pro Gln Asp Leu Glu Asp Glu Tyr Gly Gly Phe Leu Ser Glu Arg
                165                 170                 175

Ile Val Lys Asp Phe Arg Glu Tyr Ala Asp Phe Val Phe Gln Glu Tyr
            180                 185                 190

Gly Gly Lys Val Lys His Trp Ile Thr Phe Asn Glu Pro Trp Val Phe
        195                 200                 205

Ser His Ala Gly Tyr Asp Val Gly Lys Ala Pro Gly Arg Ser Ser
    210                 215                 220

Ser Tyr Val Asn Ala Lys Cys Gln Asp Gly Arg Ser Gly Tyr Glu Ala
225                 230                 235                 240

Tyr Leu Val Thr His Asn Leu Leu Ile Ser His Ala Glu Ala Val Glu
                245                 250                 255

Ala Tyr Arg Lys Cys Glu Lys Cys Lys Gly Gly Lys Ile Gly Ile Ala
            260                 265                 270

His Ser Pro Ala Trp Phe Glu Ala His Asp Leu Ala Asp Ser Gln Asp
        275                 280                 285

Gly Ala Ser Ile Asp Arg Ala Leu Asp Phe Ile Leu Gly Trp His Leu
    290                 295                 300

Asp Thr Thr Thr Phe Gly Asp Tyr Pro Gln Ile Met Lys Asp Ile Val
305                 310                 315                 320

Gly His Arg Leu Pro Lys Phe Thr Thr Glu Gln Lys Ala Lys Leu Lys
                325                 330                 335

Ala Ser Thr Asp Phe Val Gly Leu Asn Tyr Tyr Thr Ser Val Phe Ser
            340                 345                 350

Asn His Leu Glu Lys Pro Asp Pro Ser Lys Pro Arg Trp Met Gln Asp
        355                 360                 365

```
Ser Leu Ile Thr Trp Glu Ser Lys Asn Ala Gln Asn Tyr Ala Ile Gly
    370                 375                 380
Ser Lys Pro Leu Thr Ala Ala Leu Asn Val Tyr Ser Arg Gly Phe Arg
385                 390                 395                 400
Ser Leu Leu Lys Tyr Ile Lys Asp Lys Tyr Ala Asn Pro Glu Ile Met
                405                 410                 415
Ile Met Glu Asn Gly Tyr Gly Glu Glu Leu Gly Ala Ser Asp Ser Val
            420                 425                 430
Ala Val Gly Thr Ala Asp His Asn Arg Lys Tyr Tyr Leu Gln Arg His
        435                 440                 445
Leu Leu Ser Met Gln Glu Ala Val Cys Ile Asp Lys Val Asn Val Thr
    450                 455                 460
Gly Tyr Phe Val Trp Ser Leu Leu Asp Asn Phe Glu Trp Gln Asp Gly
465                 470                 475                 480
Tyr Lys Asn Arg Phe Gly Leu Tyr Tyr Val Asp Phe Lys Asn Asn Leu
                485                 490                 495
Thr Arg Tyr Glu Lys Glu Ser Gly Lys Tyr Tyr Lys Asp Phe Leu Ser
            500                 505                 510
Gln Gly Val Arg Pro Ser Ala Leu Lys Lys Asp Glu Leu
        515                 520                 525

<210> SEQ ID NO 11
<211> LENGTH: 350
<212> TYPE: DNA
<213> ORGANISM: Brassica Nigra
<220> FEATURE:
<221> NAME/KEY: misc_feature
<222> LOCATION: (1)...(350)
<223> OTHER INFORMATION: n = A,T,C or G

<400> SEQUENCE: 11
aattccnngg caatgatcat gaataancct gtgaacttct ttgtggttga tgcgttcact      60
gagtcanctt tcaaagggaa cccagcagca gtgtgcattc ttgaagagga ttatgagaga    120
gacnacgcat ggcttcagtc tcttnccgca gagtttaacg tttctgaaac ttgttttgtg    180
tntcccatta ctggtcacga tggtcncncc tccggtggtt tacnccttca ctcgagatgg    240
atctttgtgg tcatggaaca ttggcatctg ccttatagcc tcttcctcaa acggnnggtt    300
gattcagaca aggcacgagt ttntaacaca atcaggtatt cttacaggcc                350

<210> SEQ ID NO 12
<211> LENGTH: 286
<212> TYPE: DNA
<213> ORGANISM: Brassica Nigra

<400> SEQUENCE: 12
aattccggag tcacagcttt tccagtgaga aaaactctct gctcctcctt atcgttaacg     60
gaaccttcga ctgttccact cctacacgaa gccgagtaag ctrcgaaatc acacttgttc    120
atcttgaggc tccagtaatg tgctaatgga caatgtgcac ttccacatac agggtcctca    180
tccactccta atctggggga aagaaccga ctgcagaaat catacgcaga tccttcagga     240
gcagcagctg taacaatgat caactttcgg gacattttga aattca                   286

<210> SEQ ID NO 13
<211> LENGTH: 385
<212> TYPE: DNA
<213> ORGANISM: Brassica Nigra
<220> FEATURE:
<221> NAME/KEY: misc_feature
```

<222> LOCATION: (1)...(385)
<223> OTHER INFORMATION: n = A,T,C or G

<400> SEQUENCE: 13

| aattccggtt | tttttttta  | acataaaaa  | tgaaattatt | ttatttcatt | tcattgcaat | 60  |
| acattgcagc | atttcatttc | attacaatac | attncagcat | tatgcatgca | tgatgcatga | 120 |
| ctaagacctg | gtaacagaag | ttcgaccac  | aatactttaa | aacatagaga | catacgcctt | 180 |
| attatacctt | attcatattt | ttagacctt  | ttcatgcata | cacaagcaaa | catattaggt | 240 |
| catgacacaa | aacataaaac | agcagaacgg | aaacacaccg | taaccaaacc | aagaagggat | 300 |
| acttaatttg | tttgaaatcg | gagtattaag | ggtgacagtg | agagggtga  | ccagttctct | 360 |
| gaataccttc | cagttcagcc | gacgg      |            |            |            | 385 |

<210> SEQ ID NO 14
<211> LENGTH: 352
<212> TYPE: DNA
<213> ORGANISM: Brassica Nigra
<220> FEATURE:
<221> NAME/KEY: misc_feature
<222> LOCATION: (1)...(352)
<223> OTHER INFORMATION: n = A,T,C or G

<400> SEQUENCE: 14

| aattccggtt | tttttttat  | actctctact | ctttgatatc | ctaacaacat | ggcaatgctc | 60  |
| gtcagaaaca | aaaacataac | cttctcactg | gtcttgatat | gtctaattgt | ggtgtctcca | 120 |
| gtggctaagg | ctcaacttga | tgggcttctt | ggcagggatc | ccaaaatcgt | caatatacaa | 180 |
| gggcgtatga | tgtgctctat | cgatggtaat | ccgaattcca | ctcctccagt | tggttctccc | 240 |
| gttatgcttc | agtgtggtgg | aaaaaatgtt | gcaactacga | atacggtcgt | tggtggagga | 300 |
| ttctcgtcct | tccgacacag | tgtctactat | nctttcagaa | catcatcaac | ga         | 352 |

<210> SEQ ID NO 15
<211> LENGTH: 360
<212> TYPE: DNA
<213> ORGANISM: Brassica Nigra
<220> FEATURE:
<221> NAME/KEY: misc_feature
<222> LOCATION: (1)...(360)
<223> OTHER INFORMATION: n = A,T,C or G

<400> SEQUENCE: 15

| aattccggat | caagaaaagg | tctgaatcca | atatcaaata | gaacatttgc | agagatgacc | 60  |
| atgtatgtag | tcatgattca | aaggacaaaa | caattgattc | cagacaaaac | aaaacgatga | 120 |
| tcacaacgtt | acggcgaggt | ggcgctgacg | tgacggtggc | gtccgtcgag | gctcaggttg | 180 |
| gcgttgatgc | ttgtcatggt | attaagatgg | tcgctgatac | tctcctctct | gatattaccg | 240 |
| attctgtttt | cgaccttatt | gtgctccccg | gancttcccg | nnncgagact | cttaaaaact | 300 |
| gtaaactttg | gagaatatgg | taagaaaca  | agcacgagat | ggacgactta | aagacaaaac | 360 |

<210> SEQ ID NO 16
<211> LENGTH: 296
<212> TYPE: DNA
<213> ORGANISM: Brassica Nigra
<220> FEATURE:
<221> NAME/KEY: misc_feature
<222> LOCATION: (1)...(296)
<223> OTHER INFORMATION: n = A,T,C or G

<400> SEQUENCE: 16

```
gatcgacggt atcgataagc ttgatatcga atnccgggct caacaggaga tcatttgcac      60
agaccgtaga gaatttgttc gctctatctt tcttgtccaa agacggacga gtagagatca     120
ttgttgataa gaatggctca cattttgcct tgccagaaaa cgccaccagc tgcgaacctg     180
gtggcgtcag gggaagtcac ttacaaccac tttgtgattt agattcgatt caagactgga     240
gatgatgtct gaaatggtgc cgatggggga agagctaagt tacccacaca gagaaa        296
```

<210> SEQ ID NO 17
<211> LENGTH: 175
<212> TYPE: DNA
<213> ORGANISM: Brassica Nigra
<220> FEATURE:
<221> NAME/KEY: misc_feature
<222> LOCATION: (1)...(175)
<223> OTHER INFORMATION: n = A,T,C or G

<400> SEQUENCE: 17

```
tttttttttt tttngtcttt ttntttccag caatttaagt tgtttctcgt gtnantccag      60
tggttgtacg gaatagccaa agcaaacaaa gacccgtcat gaagaagaat cccatcatct     120
gaatngcaaa ccttccaatg acatctatac acnaactgat gaaccagtaa ccaga          175
```

<210> SEQ ID NO 18
<211> LENGTH: 214
<212> TYPE: DNA
<213> ORGANISM: Brassica Nigra

<400> SEQUENCE: 18

```
tctcttttgg agacaaacca aaattcctgt gatgaccacg ctatgtttct ttaggttttg      60
gctagggttt gggatcggtg gtgactatcc tctgtccgca acaatcatgt ctgagtacgc     120
taacaagaaa actcgtggag cgttcgtttc tgcggttttc gctatgcaag ggtttggatc     180
atggctggtg gcacttcgct ataatcactc ctct                                 214
```

<210> SEQ ID NO 19
<211> LENGTH: 260
<212> TYPE: DNA
<213> ORGANISM: Brassica Nigra
<220> FEATURE:
<221> NAME/KEY: misc_feature
<222> LOCATION: (1)...(260)
<223> OTHER INFORMATION: n = A,T,C or G

<400> SEQUENCE: 19

```
ctccaccgcg gtggcnncgc tctagaacta gtggatcccc cgggctgcag gttttttttt      60
tttttttttt tgattatata tgattttatt attgaaacaa aaagctcaga ggatagattg     120
tatcagtctt aaatagaact acacatcact atttaaataa acnccngcga cttaactgaa     180
gaancgccgg aaaataagaa gaacaaaaca gggaaggaag gtagatgact aggttagcct     240
aataaacaaa actgcgggcg                                                 260
```

<210> SEQ ID NO 20
<211> LENGTH: 236
<212> TYPE: DNA
<213> ORGANISM: Brassica Nigra
<220> FEATURE:
<221> NAME/KEY: misc_feature
<222> LOCATION: (1)...(236)
<223> OTHER INFORMATION: n = A,T,C or G

<400> SEQUENCE: 20

```
aattccgttg aatcacgccg ctttgctgaa ggatgagctc gacattgtga ttcctaccat      60
```

-continued

```
ccgtaacctc gagttcctcg agatgttgga ggcctcttct cagctacatc tcatcatcgt    120
caggacggag atcttaagac atcgtgttct gaagggtcga ttacnagctc tacaacagga    180
acgacattac gatctggccc aaagcttcct gcatttcctt caaggactct gcttgt       236
```

<210> SEQ ID NO 21
<211> LENGTH: 227
<212> TYPE: DNA
<213> ORGANISM: Brassica Nigra
<220> FEATURE:
<221> NAME/KEY: misc_feature
<222> LOCATION: (1)...(227)
<223> OTHER INFORMATION: n = A,T,C or G

<400> SEQUENCE: 21

```
cctccncaat nncnncgctc tagaactagt nnntcccccg ggctgcagga attccggatg     60
tgatngtcat ctaggaagaa cgtaaatatg tgaagagttt cgacaacaac agtcnnngca   120
tatagtaatc aaaaactctt tttcaatcta ccaaacaaaa caaaatgann ncatagggac   180 naanccccagc ccataaagga tctccaccta gaggccagaa aattact                227
```

<210> SEQ ID NO 22
<211> LENGTH: 327
<212> TYPE: DNA
<213> ORGANISM: Brassica Nigra

<400> SEQUENCE: 22

```
aattccggct tggagaagaa gcacatctgg acccagctct tcttcggctc ttaaccacta    60
gtgacttcgc gtttctcgtc tccacaagat cattcatgta ctgaacaacg gcctgagggc   120
cttttcggct atatcacgag gaggaacttg tagcggattc tcctgagcac gaaacacacg   180
cagcttcgta agcattctaa aagactcagg aagaacacgg atctggttat tgctgatatc   240
aagctcctcg agcatctcaa ggttccctaa ccgacctcgg caacgatatc atatcagcaa   300
agttgttccc acagcttcac aagcgac                                      327
```

<210> SEQ ID NO 23
<211> LENGTH: 361
<212> TYPE: DNA
<213> ORGANISM: Brassica Nigra

<400> SEQUENCE: 23

```
aattcgctgc agctggataa gcgtctggac acgacggcag caagtggtgg aagagatcga     60
tgagaatcca cagatctcta ccgccgagac caggctcgac gaggtcgaag ccgcgaggtc   120
tctgatacag aacgtggaga aggaagacca atcctggcta gaagccattg ctaaccagag   180
gaaaccctcc gaggttcccg acgagctatt cgccgtgctg caggagatga agagaggttc   240
gttcggtttc gtagcaaaga gcagataaga gaagccgcca agcttctcga tctggaaacg   300
gtcactctca cttcgacgat tatcagagag cttctgattg cattgcttct cttctcgacg   360
g                                                                  361
```

<210> SEQ ID NO 24
<211> LENGTH: 227
<212> TYPE: DNA
<213> ORGANISM: Brassica Nigra

<400> SEQUENCE: 24

```
accgcggtgg cgccgctcta gaactagtgg atcccccggg ctgcaggttt ttttttgta     60
```

-continued

```
tataagaaaa tggttgattt atatacatga tttacaacta gtaattcccc aaaaaatcag     120
cagagagaaa aagatatcgg aacaggactc gattgttgac catgaccact cgtctccatg     180
gtcttcatgg cgtctcagcc ccccctagca ctttagtttc tcttgaa                   227
```

<210> SEQ ID NO 25
<211> LENGTH: 228
<212> TYPE: DNA
<213> ORGANISM: Brassica Nigra

<400> SEQUENCE: 25

```
tcagctcgcc gccaagatcc taggaaagct tttagggttt tcgtgtcaga ctcttcgttt      60 ttttttttt ggttcacgac catcttaaga tcttattctc ttcttttctt tgccttgggc     120
gagcttgatt acgacgcatg ttgcgttttg ctgtctaagt ttttgattct cttcaaagta    180
aaaatagtga tacattatat ctggaaagaa aactagtgat ccgatct                   228
```

<210> SEQ ID NO 26
<211> LENGTH: 296
<212> TYPE: DNA
<213> ORGANISM: Brassica Nigra

<400> SEQUENCE: 26

```
aattccggtt tttttcaatg aaataactgt atggttaata acttgatata gcaatataga     60
gtctagacca acgtacagtt tacaaagaaa gagaagatga aaagcagtac tttgggtttc    120
agaacaaggc ttttattgaa ggaccctta ttgaaccaat accataacct ataggatcaa     180
aggcctaaaa gagaggtaag cttgtaggga acgaacttg catccactgc ttctcatacg     240
taaccaatgg ctccagccta actctcagca accagttcat tgcaagttct agagcg        296
```

<210> SEQ ID NO 27
<211> LENGTH: 319
<212> TYPE: DNA
<213> ORGANISM: Brassica Nigra

<400> SEQUENCE: 27

```
aattccgggg caagtcgacc tccagttatt tcatttcaac aaatgtcttt caactcaggc      60
cacattgaac gaagatttat ggaggtacca cttggggcaa catgggctga ggctacgatg    120
cgaacttcgg ggtttgatac tacacggaga ttttatattg atgcgcttca gatttgcccg    180
ttgagaaggc ctatcaagtg ggagaacgca acaacatttg catctccatc tgctaaaagc    240
tttgcgtttc agtggttagt ggtcaaacga tggaactagc tctagctcaa tctgggtcag    300
tggctggagt gcaaccaac                                                  319
```

<210> SEQ ID NO 28
<211> LENGTH: 351
<212> TYPE: PRT
<213> ORGANISM: Glycine max

<400> SEQUENCE: 28

```
Met Asp Lys Tyr Glu Ala Val Lys Asp Leu Gly Ala Gly Asn Phe Gly
 1               5                  10                  15

Val Ala Arg Leu Met Arg Asn Lys Glu Thr Lys Glu Leu Val Ala Met
            20                  25                  30

Lys Tyr Ile Glu Arg Gly Gln Lys Ile Asp Glu Asn Val Ala Arg Glu
        35                  40                  45

Ile Ile Asn His Arg Ser Leu Arg His Pro Asn Ile Ile Arg Phe Lys
    50                  55                  60
```

-continued

```
Glu Val Val Leu Thr Pro Thr His Leu Ala Ile Val Met Glu Tyr Ala
 65                  70                  75                  80

Ala Gly Gly Glu Leu Phe Glu Arg Ile Cys Asn Ala Gly Arg Phe Ser
                 85                  90                  95

Glu Asp Glu Ala Arg Tyr Phe Gln Gln Leu Ile Ser Gly Val His
            100                 105                 110

Tyr Cys His Ala Met Gln Ile Cys His Arg Asp Leu Lys Leu Glu Asn
            115                 120                 125

Thr Leu Leu Asp Gly Ser Pro Ala Pro Arg Leu Lys Ile Cys Asp Phe
130                 135                 140

Gly Tyr Ser Lys Ser Ser Leu Leu His Ser Arg Pro Lys Ser Thr Val
145                 150                 155                 160

Gly Thr Pro Ala Tyr Ile Ala Pro Glu Val Leu Ser Arg Arg Glu Tyr
                165                 170                 175

Asp Gly Lys Leu Ala Asp Val Trp Ser Cys Gly Val Thr Leu Tyr Val
                180                 185                 190

Met Leu Val Gly Ala Tyr Pro Phe Glu Asp Gln Asp Pro Arg Asn
            195                 200                 205

Phe Arg Lys Thr Ile Gln Arg Ile Met Ala Val Gln Tyr Lys Ile Pro
210                 215                 220

Asp Tyr Val His Ile Ser Gln Asp Cys Arg His Leu Leu Ser Arg Ile
225                 230                 235                 240

Phe Val Ala Asn Pro Leu Arg Arg Ile Ser Leu Lys Glu Ile Lys Ser
                245                 250                 255

His Pro Trp Phe Leu Lys Asn Leu Pro Arg Glu Leu Thr Glu Ser Ala
            260                 265                 270

Gln Ala Val Tyr Tyr Gln Arg Gly Asn Pro Ser Phe Ser Ile Gln Ser
            275                 280                 285

Val Glu Glu Ile Met Lys Ile Val Gly Glu Ala Arg Asp Pro Pro
290                 295                 300

Val Ser Arg Pro Val Lys Gly Phe Gly Trp Asp Gly Glu Glu Asp Glu
305                 310                 315                 320

Gly Glu Glu Asp Val Glu Glu Glu Asp Glu Glu Asp Glu Tyr Asp
                325                 330                 335

Lys Arg Val Lys Glu Val His Ala Ser Gly Glu Phe Gln Ile Ser
            340                 345                 350
```

<210> SEQ ID NO 29
<211> LENGTH: 354
<212> TYPE: PRT
<213> ORGANISM: Brassica napus

<400> SEQUENCE: 29

```
Met Glu Lys Tyr Glu Leu Val Lys Asp Ile Gly Ala Gly Asn Phe Gly
 1               5                  10                  15

Val Ala Arg Leu Met Lys Val Lys Asn Ser Lys Glu Leu Val Ala Met
                20                  25                  30

Lys Tyr Ile Glu Arg Gly Pro Lys Ile Asp Glu Asn Val Ala Arg Glu
            35                  40                  45

Ile Ile Asn His Arg Ser Leu Arg His Pro Asn Ile Ile Arg Phe Lys
        50                  55                  60

Glu Val Val Leu Thr Pro Thr His Leu Ala Ile Ala Met Glu Tyr Ala
 65                  70                  75                  80

Ala Gly Gly Glu Leu Phe Glu Arg Ile Cys Ser Ala Gly Arg Phe Ser
```

-continued

```
                85                  90                  95
Glu Asp Glu Ala Arg Tyr Phe Gln Gln Leu Ile Ser Gly Val Ser
                100                 105                 110
Tyr Cys His Ala Met Gln Ile Cys His Arg Asp Leu Lys Leu Glu Asn
            115                 120                 125
Thr Leu Leu Asp Gly Ser Pro Ala Pro Arg Leu Lys Ile Cys Asp Phe
        130                 135                 140
Gly Tyr Ser Lys Ser Ser Leu Leu His Ser Arg Pro Lys Ser Thr Val
145                 150                 155                 160
Gly Thr Pro Ala Tyr Ile Ala Pro Glu Val Leu Ser Arg Arg Glu Tyr
                165                 170                 175
Asp Gly Lys Met Ala Asp Val Trp Ser Cys Gly Val Thr Leu Tyr Val
            180                 185                 190
Met Leu Val Gly Ala Tyr Pro Phe Glu Asp Gln Glu Asp Pro Lys Asn
        195                 200                 205
Phe Arg Lys Thr Ile Gln Lys Ile Met Ala Val Gln Tyr Lys Ile Pro
    210                 215                 220
Asp Tyr Val His Ile Ser Gln Asp Cys Lys His Leu Leu Ser Arg Ile
225                 230                 235                 240
Phe Val Ala Asn Ser Leu Lys Arg Ile Thr Ile Ala Glu Ile Lys Lys
                245                 250                 255
His Pro Trp Phe Leu Lys Asn Leu Pro Arg Glu Leu Thr Glu Thr Ala
            260                 265                 270
Gln Ala Ala Tyr Phe Lys Lys Glu Asn Pro Thr Phe Ser Pro Gln Thr
        275                 280                 285
Ala Glu Glu Ile Met Lys Ile Val Asp Asp Ala Lys Thr Pro Pro Pro
    290                 295                 300
Val Ser Arg Ser Ile Gly Gly Phe Gly Trp Gly Gly Lys Gly Asp Glu
305                 310                 315                 320
Glu Glu Glu Glu Val Asp Glu Glu Val Val Glu Glu Glu Glu Asp
                325                 330                 335
Glu Glu Asp Glu Tyr Asp Lys Thr Val Lys Glu Ala His Ala Ser Gly
            340                 345                 350
Glu Val
```

<210> SEQ ID NO 30
<211> LENGTH: 363
<212> TYPE: PRT
<213> ORGANISM: Arabidopsis Thaliana

<400> SEQUENCE: 30

```
Met Asp Lys Tyr Glu Leu Val Lys Asp Ile Gly Ala Gly Asn Phe Gly
1               5                   10                  15
Val Ala Arg Leu Met Lys Val Lys Asn Ser Lys Glu Leu Val Ala Met
            20                  25                  30
Lys Tyr Ile Glu Arg Gly Pro Lys Ile Asp Glu Asn Val Ala Arg Glu
        35                  40                  45
Ile Ile Asn His Arg Ser Leu Arg His Pro Asn Ile Ile Arg Phe Lys
    50                  55                  60
Glu Val Val Leu Thr Pro Thr His Leu Ala Ile Ala Met Glu Tyr Ala
65                  70                  75                  80
Ala Gly Gly Glu Leu Phe Glu Arg Ile Cys Ser Ala Gly Arg Phe Ser
                85                  90                  95
Glu Asp Glu Ala Arg Tyr Phe Phe Gln Gln Leu Ile Ser Gly Val Ser
```

-continued

```
                100                 105                 110
Tyr Cys His Ala Met Gln Ile Cys His Arg Asp Leu Lys Leu Glu Asn
            115                 120                 125
Thr Leu Leu Asp Gly Ser Pro Ala Pro Arg Leu Lys Ile Cys Asp Phe
        130                 135                 140
Gly Tyr Ser Lys Ser Ser Leu Leu His Ser Arg Pro Lys Ser Thr Val
145                 150                 155                 160
Gly Thr Pro Ala Tyr Ile Ala Pro Glu Val Leu Ser Arg Arg Glu Tyr
                165                 170                 175
Asp Gly Lys Met Ala Asp Val Trp Ser Cys Gly Val Thr Leu Tyr Val
            180                 185                 190
Met Leu Val Gly Ala Tyr Pro Phe Glu Asp Gln Glu Asp Pro Lys Asn
        195                 200                 205
Phe Arg Lys Thr Ile Gln Lys Ile Met Ala Val Gln Tyr Lys Ile Pro
210                 215                 220
Asp Tyr Val His Ile Ser Gln Asp Cys Lys Asn Leu Leu Ser Arg Ile
225                 230                 235                 240
Phe Val Ala Asn Ser Leu Lys Arg Ile Thr Ile Ala Glu Ile Lys Lys
                245                 250                 255
His Ser Trp Phe Leu Lys Asn Leu Pro Arg Glu Leu Thr Glu Thr Ala
            260                 265                 270
Gln Ala Ala Tyr Phe Lys Lys Glu Asn Pro Thr Phe Ser Leu Gln Thr
        275                 280                 285
Val Glu Glu Ile Met Lys Ile Val Ala Asp Ala Lys Thr Pro Pro Pro
    290                 295                 300
Val Ser Arg Ser Ile Gly Gly Phe Gly Trp Gly Gly Asn Gly Asp Ala
305                 310                 315                 320
Asp Gly Lys Glu Glu Asp Ala Glu Asp Val Glu Glu Glu Glu Glu Glu
                325                 330                 335
Val Glu Glu Glu Glu Asp Asp Glu Asp Glu Tyr Asp Lys Thr Val Lys
            340                 345                 350
Glu Val His Ala Ser Gly Glu Val Arg Ile Ser
        355                 360
```

<210> SEQ ID NO 31
<211> LENGTH: 353
<212> TYPE: PRT
<213> ORGANISM: Arabidopsis Thaliana

<400> SEQUENCE: 31

```
Met Asp Lys Tyr Asp Val Val Lys Asp Leu Gly Ala Gly Asn Phe Gly
1               5                   10                  15
Val Ala Arg Leu Leu Arg His Lys Asp Thr Lys Glu Leu Val Ala Met
            20                  25                  30
Lys Tyr Ile Glu Arg Gly Arg Lys Ile Asp Glu Asn Val Ala Arg Glu
        35                  40                  45
Ile Ile Asn His Arg Ser Phe Lys His Pro Asn Ile Ile Arg Phe Lys
    50                  55                  60
Glu Val Ile Leu Thr Pro Thr His Leu Ala Ile Val Met Glu Tyr Ala
65                  70                  75                  80
Ser Gly Gly Glu Leu Phe Asp Arg Ile Cys Thr Ala Gly Arg Phe Ser
                85                  90                  95
Glu Ala Glu Ala Arg Tyr Phe Phe Gln Gln Leu Ile Cys Gly Val Asp
            100                 105                 110
```

```
Tyr Cys His Ser Leu Gln Ile Cys His Arg Asp Leu Lys Leu Glu Asn
            115                 120                 125

Thr Leu Leu Asp Gly Ala Pro Ala Pro Leu Leu Lys Ile Cys Asp Phe
    130                 135                 140

Gly Tyr Ser Lys Ser Ser Ile Leu His Ser Arg Pro Lys Ser Thr Val
145                 150                 155                 160

Gly Thr Pro Ala Tyr Ile Ala Pro Glu Val Leu Ser Arg Arg Glu Tyr
                165                 170                 175

Asp Gly Lys His Ala Asp Val Trp Ser Cys Gly Val Thr Leu Tyr Val
            180                 185                 190

Met Leu Val Gly Ala Tyr Pro Phe Glu Asp Pro Asn Asp Pro Lys Asn
        195                 200                 205

Phe Arg Lys Thr Ile Gln Arg Ile Met Ala Val Gln Tyr Lys Ile Pro
    210                 215                 220

Asp Tyr Val His Ile Ser Gln Glu Cys Lys His Leu Leu Ser Arg Ile
225                 230                 235                 240

Phe Val Thr Asn Ser Ala Lys Arg Ile Thr Leu Lys Glu Ile Lys Asn
                245                 250                 255

His Pro Trp Tyr Leu Lys Asn Leu Pro Lys Glu Leu Leu Glu Ser Ala
            260                 265                 270

Gln Ala Ala Tyr Tyr Lys Arg Asp Thr Ser Phe Ser Leu Gln Ser Val
        275                 280                 285

Glu Asp Ile Met Lys Ile Val Gly Glu Ala Arg Asn Pro Ala Pro Ser
    290                 295                 300

Thr Ser Ala Val Lys Ser Ser Gly Ser Gly Ala Asp Glu Glu Glu Glu
305                 310                 315                 320

Glu Asp Val Glu Ala Glu Val Glu Glu Glu Asp Asp Glu Asp Glu Glu
                325                 330                 335

Tyr Glu Lys His Val Lys Glu Ala Gln Ser Cys Gln Glu Ser Asp Lys
            340                 345                 350

Ala

<210> SEQ ID NO 32
<211> LENGTH: 359
<212> TYPE: PRT
<213> ORGANISM: Brassica napus

<400> SEQUENCE: 32

Met Glu Lys Tyr Glu Leu Val Lys Asp Ile Gly Ala Gly Asn Phe Gly
  1               5                  10                  15

Val Ala Arg Leu Met Lys Val Lys Asp Ser Lys Glu Leu Val Ala Met
                 20                  25                  30

Lys Tyr Ile Glu Arg Gly Pro Lys Ile Asp Glu Asn Val Ala Arg Glu
            35                  40                  45

Ile Tyr Asn His Arg Ser Leu Arg His Pro Asn Ile Ile Arg Phe Lys
        50                  55                  60

Glu Val Val Leu Thr Pro Thr His Leu Ala Ile Ala Met Glu Tyr Ala
65                  70                  75                  80

Ala Gly Gly Glu Leu Phe Glu Arg Ile Cys Gly Ala Gly Arg Phe Ser
                85                  90                  95

Glu Asp Glu Ala Arg Tyr Phe Gln Gln Leu Ile Ser Gly Val Ser
            100                 105                 110

Tyr Cys His Ala Met Gln Ile Cys His Arg Asp Leu Lys Leu Glu Asn
            115                 120                 125
```

```
Thr Leu Leu Asp Gly Ser Pro Ala Pro Arg Leu Lys Ile Cys Asp Phe
    130                 135                 140

Gly Tyr Ser Lys Ser Ser Leu Leu His Ser Arg Pro Lys Ser Thr Val
145                 150                 155                 160

Gly Thr Pro Ala Tyr Ile Ala Pro Glu Val Leu Ser Arg Arg Glu Tyr
                165                 170                 175

Asp Gly Lys Met Ala Asp Val Trp Ser Cys Gly Val Thr Leu Tyr Val
            180                 185                 190

Met Leu Val Gly Ala Tyr Pro Phe Glu Asp Gln Glu Asp Pro Lys Asn
        195                 200                 205

Phe Arg Lys Thr Ile Gln Lys Ile Met Ala Val Gln Tyr Lys Ile Pro
    210                 215                 220

Asp Tyr Val His Ile Ser Gln Asp Cys Lys His Leu Leu Ser Arg Ile
225                 230                 235                 240

Phe Val Ala Asn Ser Leu Lys Arg Ile Thr Ile Ala Glu Ile Lys Lys
                245                 250                 255

His Pro Trp Phe Thr Lys Asn Leu Pro Arg Glu Leu Thr Glu Thr Ala
            260                 265                 270

Gln Ala Ala Tyr Phe Lys Lys Glu Asn Pro Thr Phe Ser Ala Gln Thr
        275                 280                 285

Ala Glu Glu Ile Met Lys Ile Val Asp Asp Ala Lys Thr Pro Pro Pro
    290                 295                 300

Val Ser Arg Ser Ile Gly Gly Phe Gly Trp Gly Gly Glu Gly Asp Leu
305                 310                 315                 320

Glu Gly Lys Glu Glu Glu Val Asp Glu Glu Val Glu Glu Glu
                325                 330                 335

Glu Asp Glu Glu Asp Glu Tyr Asp Lys Thr Val Lys Glu Val His Ala
            340                 345                 350

Ser Gly Glu Val Arg Ile Ser
        355

<210> SEQ ID NO 33
<211> LENGTH: 339
<212> TYPE: PRT
<213> ORGANISM: Glycine max

<400> SEQUENCE: 33

Met Asp Glu Arg Tyr Glu Thr Leu Lys Glu Leu Gly Ser Gly Asn Phe
1               5                   10                  15

Gly Val Ala Arg Leu Ala Lys Asp Lys Glu Thr Gly Glu Leu Val Ala
            20                  25                  30

Ile Lys Tyr Ile Glu Arg Gly Lys Lys Ile Asp Ala Asn Val Gln Arg
        35                  40                  45

Glu Ile Val Asn His Arg Ser Leu Arg His Pro Asn Ile Ile Arg Phe
    50                  55                  60

Lys Glu Val Phe Leu Thr Pro Thr His Leu Ala Ile Val Leu Glu Tyr
65                  70                  75                  80

Ala Ala Gly Gly Glu Leu Phe Glu Arg Ile Cys Asn Ala Gly Arg Leu
                85                  90                  95

Ser Glu Asp Glu Ala Arg Phe Phe Phe Gln Gln Leu Ile Ser Gly Val
            100                 105                 110

Ser Tyr Cys His Ser Met Gln Ile Cys His Arg Asp Leu Lys Leu Glu
        115                 120                 125

Asn Thr Leu Leu Asp Gly Asn Pro Ala Pro Arg Leu Lys Ile Cys Asp
    130                 135                 140
```

-continued

Phe Gly Phe Ser Lys Ser Ala Leu Leu His Ser Gln Pro Lys Ser Thr
145                 150                 155                 160

Val Gly Thr Pro Ala Tyr Ile Ala Pro Glu Val Leu Ser Arg Lys Glu
                165                 170                 175

Tyr Asp Gly Lys Val Ala Asp Val Trp Ser Cys Gly Val Thr Leu Tyr
            180                 185                 190

Val Met Leu Val Gly Ala Tyr Pro Phe Glu Asp Pro Glu Asp Pro Lys
        195                 200                 205

Asn Phe Arg Lys Ser Ile Gly Arg Ile Met Ser Val Gln Tyr Ala Ile
    210                 215                 220

Pro Asp Tyr Val Arg Val Ser Lys Glu Cys Arg His Leu Ile Ser Arg
225                 230                 235                 240

Ile Phe Val Ala Asn Pro Ala Lys Arg Ile Asn Ile Ser Glu Ile Lys
                245                 250                 255

Gln His Leu Trp Phe Arg Lys Asn Leu Pro Arg Glu Ile Ile Glu Ala
            260                 265                 270

Glu Arg Arg Gly Tyr Glu Glu Thr Gln Lys Asp Gln Pro Ser Gln Ser
        275                 280                 285

Val Glu Glu Ile Met Gln Ile Ile Gln Glu Ala Arg Thr Lys Ile His
    290                 295                 300

Thr Gly Glu Gln Ala Gly Thr Gly Thr Ser Asp Val Val Arg Gly Asp
305                 310                 315                 320

Glu Ala Asn Glu Glu Val Asp Ile Asn Asp His Phe Ala Lys Tyr Leu
                325                 330                 335

Thr Leu Asp

<210> SEQ ID NO 34
<211> LENGTH: 524
<212> TYPE: PRT
<213> ORGANISM: Arabidopsis Thaliana

<400> SEQUENCE: 34

Met Val Leu Gln Lys Leu Pro Leu Ile Gly Leu Leu Leu Leu Leu Thr
1               5                   10                  15

Ile Val Ala Ser Pro Ala Asn Ala Asp Gly Pro Val Cys Pro Pro Ser
                20                  25                  30

Asn Lys Leu Ser Arg Ala Ser Phe Pro Glu Gly Phe Leu Phe Gly Thr
            35                  40                  45

Ala Thr Ala Ala Tyr Gln Val Glu Gly Ala Ile Asn Glu Thr Cys Arg
        50                  55                  60

Gly Pro Ala Leu Trp Asp Ile Tyr Cys Arg Arg Tyr Pro Glu Arg Cys
65                  70                  75                  80

Asn Asn Asp Asn Gly Asp Val Ala Val Asp Phe Phe His Arg Tyr Lys
                85                  90                  95

Glu Asp Ile Gln Leu Met Lys Asn Leu Asn Thr Asp Ala Phe Arg Met
            100                 105                 110

Ser Ile Ala Trp Pro Arg Ile Phe Pro His Gly Arg Lys Glu Lys Gly
        115                 120                 125

Val Ser Gln Ala Gly Val Gln Phe Tyr His Asp Leu Ile Asp Glu Leu
    130                 135                 140

Ile Lys Asn Gly Ile Thr Pro Phe Val Thr Val Phe His Trp Asp Thr
145                 150                 155                 160

Pro Gln Asp Leu Glu Asp Glu Tyr Gly Gly Phe Leu Ser Glu Arg Ile
                165                 170                 175

Val Lys Asp Phe Arg Glu Tyr Ala Asp Phe Val Phe Gln Glu Tyr Gly
            180                 185                 190

Gly Lys Val Lys His Trp Ile Thr Phe Asn Glu Pro Trp Val Phe Leu
        195                 200                 205

His Ala Gly Tyr Asp Val Gly Lys Lys Ala Pro Gly Arg Cys Ser Ser
    210                 215                 220

Tyr Val Asn Ala Lys Cys Gln Asp Gly Arg Ser Gly Tyr Glu Ala Tyr
225                 230                 235                 240

Leu Val Thr His Asn Leu Leu Ile Ser His Ala Glu Ala Val Glu Ala
                245                 250                 255

Tyr Arg Lys Cys Glu Lys Cys Lys Gly Gly Lys Ile Gly Ile Ala His
            260                 265                 270

Ser Pro Ala Trp Phe Glu Ala His Asp Leu Ala Asp Ser Gln Asp Gly
        275                 280                 285

Ala Ser Ile Asp Arg Ala Leu Asp Phe Ile Leu Gly Trp His Leu Asp
    290                 295                 300

Thr Thr Thr Phe Gly Asp Tyr Pro Gln Ile Met Lys Asp Ile Val Gly
305                 310                 315                 320

His Arg Leu Pro Lys Phe Thr Thr Glu Gln Lys Ala Lys Leu Lys Ala
                325                 330                 335

Ser Thr Asp Phe Val Gly Leu Asn Tyr Tyr Thr Ser Val Phe Ser Asn
            340                 345                 350

His Leu Glu Lys Pro Asp Pro Ser Lys Pro Arg Trp Met Gln Asp Ser
        355                 360                 365

Leu Ile Thr Trp Glu Ser Lys Asn Ala Gln Asn Tyr Ala Ile Gly Ser
    370                 375                 380

Lys Pro Leu Thr Ala Ala Leu Asn Val Tyr Ser Arg Gly Phe Arg Ser
385                 390                 395                 400

Leu Leu Lys Tyr Ile Lys Asp Lys Tyr Ala Asn Pro Glu Ile Met Ile
                405                 410                 415

Met Glu Asn Gly Tyr Gly Glu Glu Leu Gly Ala Ser Asp Ser Val Ala
            420                 425                 430

Val Gly Thr Ala Asp His Asn Arg Lys Tyr Tyr Leu Gln Arg His Leu
        435                 440                 445

Leu Ser Met Gln Glu Ala Val Cys Ile Asp Lys Val Asn Val Thr Gly
    450                 455                 460

Tyr Phe Val Trp Ser Leu Leu Asp Asn Phe Glu Trp Gln Asp Gly Tyr
465                 470                 475                 480

Lys Asn Arg Phe Gly Leu Tyr Tyr Val Asp Phe Lys Asn Asn Leu Thr
                485                 490                 495

Arg Tyr Glu Lys Glu Ser Gly Lys Tyr Tyr Lys Asp Phe Leu Ser Gln
            500                 505                 510

Gly Val Arg Pro Ser Ala Leu Lys Lys Asp Glu Leu
        515                 520

<210> SEQ ID NO 35
<211> LENGTH: 514
<212> TYPE: PRT
<213> ORGANISM: Brassica napus

<400> SEQUENCE: 35

Met Lys Phe Pro Leu Leu Gly Leu Leu Leu Val Thr Leu Val Gly
  1               5                  10                  15

Ser Pro Thr Arg Ala Glu Glu Gly Pro Val Cys Pro Lys Thr Glu Thr

-continued

```
                    20                  25                  30
Leu Ser Arg Ala Ser Phe Pro Glu Gly Phe Met Phe Gly Thr Ala Thr
                35                  40                  45
Ala Ser Tyr Gln Val Glu Gly Ala Val Asn Glu Gly Cys Arg Gly Pro
 50                  55                  60
Ser Leu Trp Asp Ile Tyr Thr Lys Lys Phe Pro His Arg Val Lys Asn
 65                  70                  75                  80
His Asn Ala Asp Val Ala Val Asp Phe Tyr His Arg Phe Arg Glu Asp
                85                  90                  95
Ile Lys Leu Met Lys Lys Leu Asn Thr Asp Ala Leu Arg Leu Ser Ile
               100                 105                 110
Ala Trp Pro Arg Ile Phe Pro His Gly Arg Met Glu Lys Gly Asn Ser
               115                 120                 125
Lys Glu Gly Val Gln Phe Tyr His Asp Leu Ile Asp Glu Leu Leu Lys
               130                 135                 140
Asn Asp Leu Thr Pro Leu Val Thr Ile Phe His Trp Asp Met Pro Ala
145                 150                 155                 160
Asp Leu Glu Asp Glu Tyr Gly Gly Phe Leu Ser Glu Arg Val Val Pro
               165                 170                 175
Asp Phe Val Glu Tyr Ala Asn Phe Thr Phe His Glu Tyr Gly Asp Lys
               180                 185                 190
Val Lys Asn Trp Ile Thr Phe Asn Glu Pro Trp Val Phe Ser Arg Ser
               195                 200                 205
Ala Tyr Asp Val Gly Lys Lys Ala Pro Gly Arg Cys Ser Pro Tyr Ile
               210                 215                 220
Lys Asp Phe Gly His Leu Cys Gln Asp Gly Arg Ser Gly Phe Glu Ala
225                 230                 235                 240
Tyr Val Val Ser His Asn Leu Leu Val Ser His Ala Glu Ala Val Asp
               245                 250                 255
Ala Phe Arg Lys Cys Glu Lys Cys Lys Gly Asp Lys Ile Gly Ile Ala
               260                 265                 270
His Ser Pro Ala Trp Phe Glu Pro Glu Asp Val Glu Gly Gly Gln Arg
               275                 280                 285
Thr Val Asp Arg Val Leu Asp Phe Ile Met Gly Trp His Leu Asp Pro
               290                 295                 300
Thr Thr Tyr Gly Asp Tyr Pro Gln Ser Met Lys Asp Ala Val Gly Ala
305                 310                 315                 320
Arg Leu Pro Lys Phe Thr Lys Ala Gln Lys Ala Lys Leu Lys Gly Ser
               325                 330                 335
Ala Asp Phe Val Gly Ile Asn Tyr Tyr Ser Ser Phe Tyr Ala Lys Ala
               340                 345                 350
Ser Glu Lys Pro Asp Tyr Arg Gln Pro Ser Trp Ala Thr Asp Ser Leu
               355                 360                 365
Val Glu Phe Glu Pro Lys Thr Val Asp Gly Ser Val Lys Ile Gly Ser
               370                 375                 380
Gln Pro Ser Thr Ala Lys Met Ala Val Tyr Ala Ala Gly Leu Arg Lys
385                 390                 395                 400
Leu Val Lys Tyr Ile Lys Asp Arg Tyr Gly Asn Pro Glu Ile Ile Ile
               405                 410                 415
Thr Glu Asn Gly Tyr Gly Glu Asp Leu Gly Glu Lys Asp Thr Asp His
               420                 425                 430
Ser Val Ala Leu Asn Asp His Asn Arg Lys Tyr Tyr His Gln Arg His
               435                 440                 445
```

```
Leu Leu Ser Leu His Gln Ala Ile Cys Glu Asp Lys Val Asn Val Thr
450                     455                     460

Ser Tyr Phe Val Trp Ser Leu Met Asp Asn Phe Glu Trp Leu Asp Gly
465                     470                     475                     480

Tyr Thr Ala Arg Phe Gly Leu Tyr Tyr Ile Asp Phe Gln Asn Asn Leu
                485                     490                     495

Thr Arg Met Glu Lys Glu Ser Ala Thr Cys Ser Leu Asn Ser Ser Asn
            500                     505                     510

Arg Ala

<210> SEQ ID NO 36
<211> LENGTH: 425
<212> TYPE: PRT
<213> ORGANISM: Trifolum repens

<400> SEQUENCE: 36

Leu Leu Ser Ile Thr Thr His Ile His Ala Phe Lys Pro Leu Pro
1               5                   10                  15

Ile Ser Phe Asp Asp Phe Ser Asp Leu Asn Arg Ser Cys Phe Ala Pro
                20                      25                      30

Gly Phe Val Phe Gly Thr Ala Ser Ser Ala Phe Gln Tyr Glu Gly Ala
            35                      40                      45

Ala Phe Glu Asp Gly Lys Gly Pro Ser Ile Trp Asp Thr Phe Thr His
50                      55                      60

Lys Tyr Pro Glu Lys Ile Lys Asp Arg Thr Asn Gly Asp Val Ala Ile
65                      70                      75                      80

Asp Glu Tyr His Arg Tyr Lys Glu Asp Ile Gly Ile Met Lys Asp Met
                85                      90                      95

Asn Leu Asp Ala Tyr Arg Phe Ser Ile Ser Trp Pro Arg Val Leu Pro
            100                     105                     110

Lys Gly Lys Leu Ser Gly Gly Val Asn Arg Glu Gly Ile Asn Tyr Tyr
            115                     120                     125

Asn Asn Leu Ile Asn Glu Val Leu Ala Asn Gly Met Gln Pro Tyr Val
        130                     135                     140

Thr Leu Phe His Trp Asp Val Pro Gln Ala Leu Glu Asp Glu Tyr Arg
145                     150                     155                     160

Gly Phe Leu Gly Arg Asn Ile Val Asp Asp Phe Arg Asp Tyr Ala Glu
                165                     170                     175

Leu Cys Phe Lys Glu Phe Gly Asp Arg Val Lys His Trp Ile Thr Leu
            180                     185                     190

Asn Glu Pro Trp Gly Val Ser Met Asn Ala Tyr Ala Tyr Gly Thr Phe
        195                     200                     205

Ala Pro Gly Arg Cys Ser Asp Trp Leu Lys Leu Asn Cys Thr Gly Gly
    210                     215                     220

Asp Ser Gly Arg Glu Pro Tyr Leu Ala Ala His Tyr Gln Leu Leu Ala
225                     230                     235                     240

His Ala Ala Ala Arg Leu Tyr Lys Thr Lys Tyr Gln Ala Ser Gln
                245                     250                     255

Asn Gly Ile Ile Gly Ile Thr Leu Val Ser His Trp Phe Glu Pro Ala
            260                     265                     270

Ser Lys Glu Lys Ala Asp Val Asp Ala Ala Lys Arg Gly Leu Asp Phe
        275                     280                     285

Met Leu Gly Trp Phe Met His Pro Leu Thr Lys Gly Arg Tyr Pro Glu
    290                     295                     300
```

```
Ser Met Arg Tyr Leu Val Arg Lys Arg Leu Pro Lys Phe Ser Thr Glu
305                 310                 315                 320

Glu Ser Lys Glu Leu Thr Gly Ser Phe Asp Phe Leu Gly Leu Asn Tyr
            325                 330                 335

Tyr Ser Ser Tyr Tyr Ala Ala Lys Ala Pro Arg Ile Pro Asn Ala Arg
            340                 345                 350

Pro Ala Ile Gln Thr Asp Ser Leu Ile Asn Ala Thr Phe Glu His Asn
            355                 360                 365

Gly Lys Pro Leu Gly Pro Met Ala Ala Ser Ser Trp Leu Cys Ile Tyr
    370                 375                 380

Pro Gln Gly Ile Arg Lys Leu Leu Leu Tyr Val Lys Asn His Tyr Asn
385                 390                 395                 400

Asn Pro Val Ile Tyr Ile Thr Glu Asn Gly Arg Asn Ser Ser Thr Ile
                405                 410                 415

Asn Thr Val Thr Ser Arg Ile Pro Phe
                420                 425

<210> SEQ ID NO 37
<211> LENGTH: 551
<212> TYPE: PRT
<213> ORGANISM: Prunus serotina

<400> SEQUENCE: 37

Thr Lys Leu Gly Ser Leu Leu Leu Cys Ala Leu Leu Leu Ala Gly Phe
1               5                   10                  15

Ala Leu Thr Asn Ser Lys Ala Ala Lys Thr Asp Pro Pro Ile His Cys
            20                  25                  30

Ala Ser Leu Asn Arg Ser Ser Phe Asp Ala Leu Glu Pro Gly Phe Ile
        35                  40                  45

Phe Gly Thr Ala Ser Ala Ala Tyr Gln Phe Glu Gly Ala Ala Lys Glu
    50                  55                  60

Asp Gly Arg Gly Pro Ser Ile Trp Asp Thr Tyr Thr His Asn His Ser
65                  70                  75                  80

Glu Arg Ile Lys Asp Gly Ser Asn Gly Asp Val Ala Val Asp Gln Tyr
                85                  90                  95

His Arg Tyr Lys Glu Asp Val Arg Ile Met Lys Lys Met Gly Phe Asp
                100                 105                 110

Ala Tyr Arg Phe Ser Ile Ser Trp Ser Arg Val Leu Pro Asn Gly Lys
            115                 120                 125

Val Ser Gly Gly Val Asn Glu Asp Gly Ile Lys Phe Tyr Asn Asn Leu
    130                 135                 140

Ile Asn Glu Ile Leu Arg Asn Gly Leu Lys Pro Phe Val Thr Ile Tyr
145                 150                 155                 160

His Trp Asp Leu Pro Gln Ala Leu Glu Asp Glu Tyr Gly Gly Phe Leu
                165                 170                 175

Ser Pro Asn Ile Val Asp His Phe Arg Asp Tyr Ala Asn Leu Cys Phe
            180                 185                 190

Lys Lys Phe Gly Asp Arg Val Lys His Trp Ile Thr Leu Asn Glu Pro
        195                 200                 205

Tyr Thr Phe Ser Ser Ser Gly Tyr Ala Tyr Gly Val His Ala Pro Gly
    210                 215                 220

Arg Cys Ser Ala Trp Gln Lys Leu Asn Cys Thr Gly Gly Asn Ser Ala
225                 230                 235                 240

Thr Glu Pro Tyr Leu Val Thr His His Gln Leu Leu Ala His Ala Ala
```

```
                    245                 250                 255
        Ala Val Lys Leu Tyr Lys Asp Glu Tyr Gln Ala Ser Gln Asn Gly Leu
                        260                 265                 270

Ile Gly Ile Thr Leu Val Ser Pro Trp Phe Glu Pro Ala Ser Glu Ala
                        275                 280                 285

Glu Glu Asp Ile Asn Ala Ala Phe Arg Ser Leu Asp Phe Ile Phe Gly
                        290                 295                 300

Trp Phe Met Asp Pro Leu Thr Asn Gly Asn Tyr Pro His Leu Met Arg
        305                 310                 315                 320

Ser Ile Val Gly Glu Arg Leu Pro Asn Phe Thr Glu Gln Ser Lys
                        325                 330                 335

Leu Leu Lys Gly Ser Phe Asp Phe Ile Gly Leu Asn Tyr Tyr Thr Thr
                        340                 345                 350

Arg Tyr Ala Ser Asn Ala Pro Lys Ile Thr Ser Val His Ala Ser Tyr
                        355                 360                 365

Ile Thr Asp Pro Gln Val Asn Ala Thr Ala Glu Leu Lys Gly Val Pro
                        370                 375                 380

Ile Gly Pro Met Ala Ala Ser Gly Trp Leu Tyr Val Tyr Pro Lys Gly
        385                 390                 395                 400

Ile His Asp Leu Val Leu Tyr Thr Lys Glu Lys Tyr Asn Asp Pro Leu
                        405                 410                 415

Ile Tyr Ile Thr Glu Asn Gly Val Asp Glu Phe Asn Asp Pro Lys Leu
                        420                 425                 430

Ser Met Glu Glu Ala Leu Lys Asp Thr Asn Arg Ile Asp Phe Tyr Tyr
                        435                 440                 445

Arg His Leu Cys Tyr Leu Gln Ala Ala Ile Lys Lys Gly Ser Lys Val
                        450                 455                 460

Lys Gly Tyr Phe Ala Trp Ser Phe Leu Asp Asn Phe Glu Trp Asp Ala
        465                 470                 475                 480

Gly Tyr Thr Val Arg Phe Gly Ile Asn Tyr Val Asp Tyr Asn Asp Asn
                        485                 490                 495

Leu Lys Arg His Ser Lys Leu Ser Thr Tyr Trp Phe Thr Ser Phe Leu
                        500                 505                 510

Lys Lys Tyr Glu Arg Ser Thr Lys Glu Ile Gln Met Phe Val Glu Ser
                        515                 520                 525

Lys Leu Glu His Gln Lys Phe Glu Ser Gln Met Met Asn Lys Val Gln
                        530                 535                 540

Ser Ser Leu Ala Val Val Val
        545                 550

<210> SEQ ID NO 38
<211> LENGTH: 531
<212> TYPE: PRT
<213> ORGANISM: Manihot esculenta

<400> SEQUENCE: 38

Met Leu Val Leu Phe Ile Ser Leu Leu Ala Leu Thr Arg Pro Ala Met
        1               5                   10                  15

Gly Thr Asp Asp Asp Asp Asn Ile Pro Asp Asp Phe Ser Arg Lys
                        20                  25                  30

Tyr Phe Pro Asp Asp Phe Ile Phe Gly Thr Ala Thr Ser Ala Tyr Gln
                        35                  40                  45

Ile Glu Gly Glu Ala Thr Ala Lys Gly Arg Ala Pro Ser Val Trp Asp
                        50                  55                  60
```

-continued

```
Ile Phe Ser Lys Glu Thr Pro Asp Arg Ile Leu Asp Gly Ser Asn Gly
 65                  70                  75                  80

Asp Val Ala Val Asp Phe Tyr Asn Arg Tyr Ile Gln Asp Ile Lys Asn
                 85                  90                  95

Val Lys Lys Met Gly Phe Asn Ala Phe Arg Met Ser Ile Ser Trp Ser
                100                 105                 110

Arg Val Ile Pro Ser Gly Arg Arg Glu Gly Val Asn Glu Glu Gly
                115                 120                 125

Ile Gln Phe Tyr Asn Asp Val Ile Asn Glu Ile Ser Asn Gly Leu
            130                 135                 140

Glu Pro Phe Val Thr Ile Phe His Trp Asp Thr Pro Gln Ala Leu Gln
145                 150                 155                 160

Asp Lys Tyr Gly Gly Phe Leu Ser Arg Asp Ile Val Tyr Asp Tyr Leu
                165                 170                 175

Gln Tyr Ala Asp Leu Leu Phe Glu Arg Phe Gly Asp Arg Val Lys Pro
            180                 185                 190

Trp Met Thr Phe Asn Glu Pro Ser Ala Tyr Val Gly Phe Ala His Asp
            195                 200                 205

Asp Gly Val Phe Ala Pro Gly Arg Cys Ser Ser Trp Val Asn Arg Gln
        210                 215                 220

Cys Leu Ala Gly Asp Ser Ala Thr Glu Pro Tyr Ile Val Ala His Asn
225                 230                 235                 240

Leu Leu Leu Ser His Ala Ala Ala Val His Gln Tyr Arg Lys Tyr Tyr
                245                 250                 255

Gln Gly Thr Gln Lys Gly Lys Ile Gly Ile Thr Leu Phe Thr Phe Trp
            260                 265                 270

Tyr Glu Pro Leu Ser Asp Ser Lys Val Asp Val Gln Ala Ala Lys Thr
            275                 280                 285

Ala Leu Asp Phe Met Phe Gly Leu Trp Met Asp Pro Met Thr Tyr Gly
        290                 295                 300

Arg Tyr Pro Arg Thr Met Val Asp Leu Ala Gly Asp Lys Leu Ile Gly
305                 310                 315                 320

Phe Thr Asp Glu Glu Ser Gln Leu Leu Arg Gly Ser Tyr Asp Phe Val
                325                 330                 335

Gly Leu Gln Tyr Tyr Thr Ala Tyr Ala Glu Pro Ile Pro Pro Val
            340                 345                 350

Asp Pro Lys Phe Arg Arg Tyr Lys Thr Asp Ser Gly Val Asn Ala Thr
            355                 360                 365

Pro Tyr Asp Leu Asn Gly Asn Leu Ile Gly Pro Gln Ala Tyr Ser Ser
370                 375                 380

Trp Phe Tyr Ile Phe Pro Lys Gly Ile Arg His Phe Leu Asn Tyr Thr
385                 390                 395                 400

Lys Asp Thr Tyr Asn Asp Pro Val Ile Tyr Val Thr Glu Asn Gly Val
                405                 410                 415

Asp Asn Tyr Asn Asn Glu Ser Gln Pro Ile Glu Glu Ala Leu Gln Asp
            420                 425                 430

Asp Phe Arg Ile Ser Tyr Tyr Lys Lys His Met Trp Asn Ala Leu Gly
        435                 440                 445

Ser Leu Lys Asn Tyr Gly Val Lys Leu Lys Gly Tyr Phe Ala Trp Ser
450                 455                 460

Tyr Leu Asp Asn Phe Glu Trp Asn Ile Gly Tyr Thr Ser Arg Phe Gly
465                 470                 475                 480

Leu Tyr Tyr Val Asp Tyr Lys Asn Asn Leu Thr Arg Tyr Pro Lys Lys
```

485                 490                 495
Ser Ala His Trp Phe Thr Lys Phe Leu Asn Ile Ser Val Asn Ala Asn
                500                 505                 510

Asn Ile Tyr Glu Leu Thr Ser Lys Asp Ser Arg Lys Val Gly Lys Phe
        515                 520                 525

Tyr Val Met
    530

<210> SEQ ID NO 39
<211> LENGTH: 531
<212> TYPE: PRT
<213> ORGANISM: Prunus avium

<400> SEQUENCE: 39

Leu Leu Leu Leu Gly Phe Ala Leu Ala Asn Thr Asn Ala Ala Arg Thr
1               5                   10                  15

Asp Pro Pro Val Val Cys Ala Thr Leu Asn Arg Thr Asn Phe Asp Thr
                20                  25                  30

Leu Phe Pro Gly Phe Thr Phe Gly Thr Ala Thr Ala Ser Tyr Gln Leu
            35                  40                  45

Glu Gly Ala Ala Asn Ile Asp Gly Arg Gly Pro Ser Ile Trp Asp Ala
        50                  55                  60

Phe Thr His Asn His Pro Glu Lys Ile Thr Asp Gly Ser Asn Gly Asp
65                  70                  75                  80

Val Ala Ile Asp Gln Tyr His Arg Tyr Lys Glu Asp Val Ala Ile Met
                85                  90                  95

Lys Asp Met Gly Leu Asp Ala Tyr Arg Phe Ser Ile Ser Trp Ser Arg
            100                 105                 110

Leu Leu Pro Asn Gly Thr Leu Ser Gly Gly Ile Asn Lys Lys Gly Ile
        115                 120                 125

Glu Tyr Tyr Asn Asn Leu Thr Asn Glu Leu Ile Arg Asn Gly Ile Glu
130                 135                 140

Pro Leu Val Thr Leu Phe His Trp Asp Val Pro Gln Ala Leu Glu Glu
145                 150                 155                 160

Glu Tyr Gly Gly Val Leu Ser Pro Arg Ile Val Tyr Asp Phe Lys Ala
                165                 170                 175

Tyr Ala Glu Leu Cys Tyr Lys Glu Phe Gly Asp Arg Val Lys His Trp
            180                 185                 190

Thr Thr Leu Asn Glu Pro Tyr Thr Ile Ser Asn His Gly Tyr Thr Ile
        195                 200                 205

Gly Ile His Ala Pro Gly Arg Cys Ser Ser Trp Tyr Asp Pro Thr Cys
210                 215                 220

Leu Gly Gly Asp Ser Gly Thr Glu Pro Tyr Leu Val Thr His Asn Leu
225                 230                 235                 240

Leu Leu Ala His Ala Ala Val Lys Leu Tyr Arg Glu Lys Tyr Gln
                245                 250                 255

Ala Ser Gln Glu Gly Val Ile Gly Ile Thr Val Val Ser His Trp Phe
            260                 265                 270

Glu Pro Ala Ser Glu Ser Gln Lys Asp Ile Asn Ala Ser Val Arg Ala
        275                 280                 285

Leu Asp Phe Met Tyr Gly Trp Phe Met Asp Pro Leu Thr Arg Gly Asp
    290                 295                 300

Tyr Pro Gln Ser Met Arg Ser Leu Val Lys Glu Arg Leu Pro Asn Phe
305                 310                 315                 320

-continued

```
Thr Glu Glu Gln Ser Lys Ser Leu Ile Gly Ser Tyr Asp Tyr Ile Gly
                325                 330                 335

Val Asn Tyr Tyr Ser Ala Arg Tyr Ala Ser Ala Tyr Pro Glu Asp Tyr
            340                 345                 350

Ser Ile Pro Thr Pro Pro Ser Tyr Leu Thr Asp Ala Tyr Val Asn Val
        355                 360                 365

Thr Thr Glu Leu Asn Gly Val Pro Ile Gly Pro Gln Ala Ala Ser Asp
    370                 375                 380

Trp Leu Tyr Val Tyr Pro Lys Gly Leu Tyr Asp Leu Val Leu Tyr Thr
385                 390                 395                 400

Lys Asn Lys Tyr Asn Asp Pro Ile Met Tyr Ile Thr Glu Asn Gly Met
                405                 410                 415

Asp Glu Phe Asn Asn Pro Lys Ile Ser Leu Glu Gln Ala Leu Asn Asp
            420                 425                 430

Ser Asn Arg Ile Asp Tyr Cys Tyr Arg His Leu Cys Tyr Leu Gln Glu
        435                 440                 445

Ala Ile Ile Glu Gly Ala Asn Val Gln Gly Tyr Phe Ala Trp Ser Leu
    450                 455                 460

Leu Asp Asn Phe Glu Trp Ser Glu Gly Tyr Thr Val Arg Phe Gly Ile
465                 470                 475                 480

Asn Tyr Val Asp Tyr Asp Asn Gly Leu Lys Arg His Ser Lys Leu Ser
                485                 490                 495

Thr His Trp Phe Lys Asn Phe Leu Lys Arg Ser Ser Ile Ser Lys Glu
            500                 505                 510

Lys Ile Arg Arg Cys Gly Asn Asn Asn Ala Arg Ala Arg Lys Phe Val
        515                 520                 525

Tyr Arg Ile
    530

<210> SEQ ID NO 40
<211> LENGTH: 509
<212> TYPE: PRT
<213> ORGANISM: Hordeum vulgare

<400> SEQUENCE: 40

Met Arg Ser Ser Pro Val Leu Leu Val Ile Ala Leu Val Ala Ala
1               5                   10                  15

Ala His Leu Ala Pro Leu Glu Cys Asp Gly Pro Asn Pro Asn Pro Glu
            20                  25                  30

Ile Gly Asn Thr Gly Gly Leu Ser Arg Gln Gly Phe Pro Ala Gly Phe
        35                  40                  45

Val Phe Gly Thr Ala Ala Ser Ala Tyr Gln Val Glu Gly Met Ala Arg
    50                  55                  60

Gln Gly Gly Arg Gly Pro Cys Ile Trp Asp Ala Phe Val Ala Ile Gln
65                  70                  75                  80

Gly Met Ile Ala Gly Asn Gly Thr Ala Asp Val Thr Val Asp Glu Tyr
                85                  90                  95

His Arg Tyr Lys Glu Asp Val Gly Ile Met Lys Asn Met Gly Phe Asp
            100                 105                 110

Ala Tyr Arg Phe Ser Ile Ser Trp Ser Arg Ile Phe Pro Asp Gly Thr
        115                 120                 125

Gly Lys Val Asn Gln Glu Gly Val Asp Tyr Tyr Asn Arg Leu Ile Asp
    130                 135                 140

Tyr Met Leu Gln Gln Gly Ile Thr Pro Tyr Ala Asn Leu Tyr His Tyr
145                 150                 155                 160
```

-continued

```
Asp Leu Pro Leu Ala Leu His Gln Gln Tyr Leu Gly Trp Leu Ser Pro
                165                 170                 175

Lys Ile Val Gly Ala Phe Ala Asp Tyr Ala Glu Phe Cys Phe Lys Val
            180                 185                 190

Phe Gly Asp Arg Val Lys Asn Trp Phe Thr Phe Asn Glu Pro Arg Val
        195                 200                 205

Val Ala Ala Leu Gly Tyr Asp Asn Gly Phe His Ala Pro Gly Arg Cys
    210                 215                 220

Ser Lys Cys Pro Ala Gly Gly Asp Ser Arg Thr Glu Pro Tyr Ile Val
225                 230                 235                 240

Thr His Asn Ile Ile Leu Ser His Ala Ala Val Gln Arg Tyr Arg
                245                 250                 255

Glu Lys Tyr Gln Pro His Gln Lys Gly Arg Ile Gly Ile Leu Leu Asp
            260                 265                 270

Phe Val Trp Tyr Glu Pro His Ser Asp Thr Asp Ala Asp Gln Ala Ala
        275                 280                 285

Ala Gln Arg Ala Arg Asp Phe His Ile Gly Trp Phe Leu Asp Pro Ile
    290                 295                 300

Thr Asn Gly Arg Tyr Pro Ser Ser Met Leu Lys Ile Val Gly Asn Arg
305                 310                 315                 320

Leu Pro Gly Phe Ser Ala Asp Glu Ser Arg Met Val Lys Gly Ser Ile
                325                 330                 335

Asp Tyr Val Gly Ile Asn Gln Tyr Thr Ser Tyr Met Lys Asp Pro
            340                 345                 350

Gly Ala Trp Asn Gln Thr Pro Val Ser Tyr Gln Asp Asp Trp His Val
        355                 360                 365

Gly Phe Val Tyr Glu Arg Asn Gly Val Pro Ile Gly Pro Arg Ala Asn
    370                 375                 380

Ser Asp Trp Leu Tyr Ile Val Pro Trp Gly Met Asn Lys Ala Val Thr
385                 390                 395                 400

Tyr Val Lys Glu Arg Tyr Gly Asn Pro Thr Met Ile Leu Ser Glu Asn
                405                 410                 415

Gly Met Asp Gln Pro Gly Asn Val Ser Ile Ala Asp Gly Val His Asp
            420                 425                 430

Thr Val Arg Ile Arg Tyr Tyr Arg Asp Tyr Ile Thr Glu Leu Lys Lys
        435                 440                 445

Ala Ile Asp Asn Gly Ala Arg Val Ala Gly Tyr Phe Ala Trp Ser Leu
    450                 455                 460

Leu Asp Asn Phe Glu Trp Arg Leu Gly Tyr Thr Ala Arg Phe Gly Ile
465                 470                 475                 480

Val Tyr Val Asp Phe Asn Thr Leu Lys Arg Tyr Pro Lys Asp Ser Ala
                485                 490                 495

Leu Trp Phe Lys Asn Met Leu Ser Glu Lys Lys Arg Ser
            500                 505

<210> SEQ ID NO 41
<211> LENGTH: 548
<212> TYPE: PRT
<213> ORGANISM: Brassica Napus

<400> SEQUENCE: 41

Met Lys Leu Leu His Gly Leu Ala Leu Val Phe Leu Leu Ala Ala Ala
 1               5                  10                  15

Ser Cys Lys Ala Asp Glu Glu Ile Thr Cys Glu Glu Asn Asn Pro Phe
```

```
                        20                  25                  30
Thr Cys Ser Asn Thr Asp Ile Leu Ser Ser Lys Asn Phe Gly Lys Asp
            35                  40                  45
Phe Ile Phe Gly Val Ala Ser Ala Tyr Gln Ile Glu Gly Gly Arg
 50                  55                  60
Gly Arg Gly Val Asn Val Trp Asp Gly Phe Ser His Arg Tyr Pro Glu
 65                  70                  75                  80
Lys Ala Gly Ser Asp Leu Lys Asn Gly Asp Thr Thr Cys Glu Ser Tyr
                85                  90                  95
Thr Arg Trp Gln Lys Asp Val Asp Val Met Gly Glu Leu Asn Ala Thr
                    100                 105                 110
Gly Tyr Arg Phe Ser Phe Ala Trp Ser Arg Ile Ile Pro Lys Gly Lys
                115                 120                 125
Val Ser Arg Gly Val Asn Gln Gly Gly Leu Asp Tyr Tyr His Lys Leu
    130                 135                 140
Ile Asp Ala Leu Leu Glu Lys Asn Ile Thr Pro Phe Val Thr Leu Phe
145                 150                 155                 160
His Trp Asp Leu Pro Gln Thr Leu Gln Asp Glu Tyr Glu Gly Phe Leu
                165                 170                 175
Asp Arg Gln Ile Ile Gln Asp Phe Lys Asp Tyr Ala Asp Leu Cys Phe
                180                 185                 190
Lys Glu Phe Gly Gly Lys Val Lys His Trp Ile Thr Ile Asn Gln Leu
                195                 200                 205
Tyr Thr Val Pro Thr Arg Gly Tyr Ala Ile Gly Thr Asp Ala Pro Gly
                210                 215                 220
Arg Cys Ser Pro Met Val Asp Thr Lys His Arg Cys Tyr Gly Gly Asn
225                 230                 235                 240
Ser Ser Thr Glu Pro Tyr Ile Val Ala His Asn Gln Leu Leu Ala His
                245                 250                 255
Ala Thr Val Val Asp Leu Tyr Arg Thr Lys Tyr Lys Phe Gln Lys Gly
                260                 265                 270
Lys Ile Gly Pro Val Met Ile Thr Arg Trp Phe Leu Pro Phe Asp Glu
                275                 280                 285
Ser Asp Pro Ala Ser Ile Glu Ala Ala Glu Arg Met Asn Gln Phe Phe
                290                 295                 300
His Gly Trp Tyr Met Glu Pro Leu Thr Lys Gly Arg Tyr Pro Asp Ile
305                 310                 315                 320
Met Arg Gln Ile Val Gly Ser Arg Leu Pro Asn Phe Thr Glu Glu Glu
                    325                 330                 335
Ala Glu Leu Val Ala Gly Ser Tyr Asp Phe Leu Gly Leu Asn Tyr Tyr
                340                 345                 350
Val Thr Gln Tyr Ala Gln Pro Lys Pro Asn Pro Tyr Pro Ser Glu Thr
                355                 360                 365
His Thr Ala Met Met Asp Ala Gly Val Lys Leu Thr Tyr Asp Asn Ser
    370                 375                 380
Arg Gly Glu Phe Leu Gly Pro Leu Phe Val Glu Asp Lys Val Asn Gly
385                 390                 395                 400
Asn Ser Tyr Tyr Tyr Pro Lys Gly Ile Tyr Tyr Val Met Asp Tyr Phe
                    405                 410                 415
Lys Thr Lys Tyr Gly Asp Pro Leu Ile Tyr Val Thr Glu Asn Gly Phe
                420                 425                 430
Ser Thr Pro Ser Ser Glu Asn Arg Glu Gln Ala Ile Ala Asp Tyr Lys
    435                 440                 445
```

```
Arg Ile Asp Tyr Leu Cys Ser His Leu Cys Phe Leu Arg Lys Val Ile
    450                 455                 460

Lys Glu Lys Gly Val Asn Val Arg Gly Tyr Phe Ala Trp Ala Leu Gly
465                 470                 475                 480

Asp Asn Tyr Glu Phe Cys Lys Gly Phe Thr Val Arg Phe Gly Leu Ser
                485                 490                 495

Tyr Val Asn Trp Glu Asp Leu Asp Asp Arg Asn Leu Lys Glu Ser Gly
                500                 505                 510

Lys Trp Tyr Gln Arg Phe Ile Asn Gly Thr Val Lys Asn Ala Val Lys
                515                 520                 525

Gln Asp Phe Leu Arg Ser Ser Leu Ser Ser Gln Ser Gln Lys Lys Arg
                530                 535                 540

Phe Ala Asp Ala
545

<210> SEQ ID NO 42
<211> LENGTH: 539
<212> TYPE: PRT
<213> ORGANISM: Arabidopsis Thaliana

<400> SEQUENCE: 42

Met Lys Leu Leu Gly Phe Ala Leu Ala Ile Leu Leu Val Val Ala Thr
1               5                   10                  15

Cys Lys Pro Glu Glu Ile Thr Cys Glu Asn Val Pro Phe Thr
                20                  25                  30

Cys Ser Gln Thr Asp Arg Phe Asn Lys Gln Asp Phe Glu Ser Asp Phe
                35                  40                  45

Ile Phe Gly Val Ala Ser Ser Ala Tyr Gln Ile Glu Gly Gly Arg Gly
    50                  55                  60

Arg Gly Leu Asn Val Trp Asp Gly Phe Thr His Arg Tyr Pro Glu Lys
65                  70                  75                  80

Gly Gly Ala Asp Leu Gly Asn Gly Asp Thr Thr Cys Asp Ser Tyr Arg
                85                  90                  95

Thr Trp Gln Lys Asp Leu Asp Val Met Glu Glu Leu Gly Val Lys Gly
                100                 105                 110

Tyr Arg Phe Ser Phe Ala Trp Ser Arg Ile Leu Pro Lys Gly Lys Arg
                115                 120                 125

Ser Arg Gly Ile Asn Glu Asp Gly Ile Asn Tyr Tyr Ser Gly Leu Ile
                130                 135                 140

Asp Gly Leu Ile Ala Arg Asn Ile Thr Pro Phe Val Thr Leu Phe His
145                 150                 155                 160

Trp Asp Leu Pro Gln Ser Leu Gln Asp Glu Tyr Glu Gly Phe Leu Asp
                165                 170                 175

Arg Thr Ile Ile Asp Asp Phe Lys Asp Tyr Ala Asp Leu Cys Phe Glu
                180                 185                 190

Arg Phe Gly Asp Arg Val Lys His Trp Ile Thr Ile Asn Gln Leu Phe
                195                 200                 205

Thr Val Pro Thr Arg Gly Tyr Ala Leu Gly Thr Asp Ala Pro Gly Arg
                210                 215                 220

Cys Ser Gln Trp Val Asp Lys Arg Cys Tyr Gly Gly Asp Ser Ser Thr
225                 230                 235                 240

Glu Pro Tyr Ile Val Ala His Asn Gln Leu Leu Ala His Ala Thr Val
                245                 250                 255

Val Asp Leu Tyr Arg Thr Arg Tyr Lys Tyr Gln Gly Gly Lys Ile Gly
```

```
                   260                 265                 270
    Pro Val Met Ile Thr Arg Trp Phe Leu Pro Tyr Asp Asp Thr Leu Glu
                275                 280                 285

Ser Lys Gln Ala Thr Trp Arg Ala Lys Glu Phe Phe Leu Gly Trp Phe
        290                 295                 300

Met Glu Pro Leu Thr Lys Gly Lys Tyr Pro Tyr Ile Met Arg Lys Leu
    305                 310                 315                 320

Val Gly Asn Arg Leu Pro Lys Phe Asn Ser Thr Glu Ala Arg Leu Leu
                    325                 330                 335

Lys Gly Ser Tyr Asp Phe Leu Gly Leu Asn Tyr Tyr Val Thr Gln Tyr
                340                 345                 350

Ala His Ala Leu Asp Pro Ser Pro Glu Lys Leu Thr Ala Met Thr
                355                 360                 365

Asp Ser Leu Ala Asn Leu Thr Ser Leu Asp Ala Asn Gly Gln Pro Pro
        370                 375                 380

Gly Pro Pro Phe Ser Lys Gly Ser Tyr Tyr His Pro Arg Gly Met Leu
    385                 390                 395                 400

Asn Val Met Glu His Phe Lys Thr Lys Tyr Gly Asp Pro Leu Ile Tyr
                    405                 410                 415

Val Thr Glu Asn Gly Phe Ser Thr Ser Gly Gly Pro Ile Pro Phe Thr
                420                 425                 430

Glu Ala Phe His Asp Tyr Asn Arg Ile Asp Tyr Leu Cys Ser His Leu
        435                 440                 445

Cys Phe Leu Arg Lys Ala Ile Lys Glu Lys Arg Val Asn Val Lys Gly
        450                 455                 460

Tyr Phe Val Trp Ser Leu Gly Asp Asn Tyr Glu Phe Cys Asn Gly Tyr
    465                 470                 475                 480

Thr Val Arg Phe Gly Leu Ser Tyr Val Asp Phe Asn Asn Val Thr Ala
                    485                 490                 495

Asp Arg Asp Leu Lys Ala Ser Gly Leu Trp Tyr Gln Ser Phe Leu Arg
                500                 505                 510

Asp Thr Thr Lys Asn Gln Asp Ile Leu Arg Ser Ser Leu Pro Phe Lys
                515                 520                 525

Asn Gly Asp Arg Lys Ser Leu Thr Glu Asn Asp
                530                 535

<210> SEQ ID NO 43
<211> LENGTH: 540
<212> TYPE: PRT
<213> ORGANISM: Arabidopsis Thaliana

<400> SEQUENCE: 43

Met Lys Leu Leu Met Leu Ala Phe Val Phe Leu Leu Ala Leu Ala Thr
    1               5                   10                  15

Cys Lys Gly Asp Glu Phe Val Cys Glu Glu Asn Glu Pro Phe Thr Cys
                    20                  25                  30

Asn Gln Thr Lys Leu Phe Asn Ser Gly Asn Phe Glu Lys Gly Phe Ile
                35                  40                  45

Phe Gly Val Ala Ser Ser Ala Tyr Gln Val Glu Gly Arg Gly Arg
        50                  55                  60

Gly Leu Asn Val Trp Asp Ser Phe Thr His Arg Phe Pro Glu Lys Gly
    65                  70                  75                  80

Gly Ala Asp Leu Gly Asn Gly Asp Thr Thr Cys Asp Ser Tyr Thr Leu
                    85                  90                  95
```

-continued

```
Trp Gln Lys Asp Ile Asp Val Met Asp Glu Leu Asn Ser Thr Gly Tyr
            100                 105                 110

Arg Phe Ser Ile Ala Trp Ser Arg Leu Leu Pro Lys Gly Lys Arg Ser
            115                 120                 125

Arg Gly Val Asn Pro Gly Ala Ile Lys Tyr Tyr Asn Gly Leu Ile Asp
            130                 135                 140

Gly Leu Val Ala Lys Asn Met Thr Pro Phe Val Thr Leu Phe His Trp
145                 150                 155                 160

Asp Leu Pro Gln Thr Leu Gln Asp Glu Tyr Asn Gly Phe Leu Asn Lys
                165                 170                 175

Thr Ile Val Asp Asp Phe Lys Asp Tyr Ala Asp Leu Cys Phe Glu Leu
            180                 185                 190

Phe Gly Asp Arg Val Lys Asn Trp Ile Thr Ile Asn Gln Leu Tyr Thr
            195                 200                 205

Val Pro Thr Arg Gly Tyr Ala Leu Gly Thr Asp Ala Pro Gly Arg Cys
            210                 215                 220

Ser Pro Lys Ile Asp Val Arg Cys Pro Gly Gly Asn Ser Ser Thr Glu
225                 230                 235                 240

Pro Tyr Ile Val Ala His Asn Gln Leu Leu Ala His Ala Ala Ala Val
                245                 250                 255

Asp Val Tyr Arg Thr Lys Tyr Lys Asp Asp Gln Lys Gly Met Ile Gly
            260                 265                 270

Pro Val Met Ile Thr Arg Trp Phe Leu Pro Phe Asp His Ser Gln Glu
            275                 280                 285

Ser Lys Asp Ala Thr Glu Arg Ala Lys Ile Phe Phe His Gly Trp Phe
290                 295                 300

Met Gly Pro Leu Thr Glu Gly Lys Tyr Pro Asp Ile Met Arg Glu Tyr
305                 310                 315                 320

Val Gly Asp Arg Leu Pro Glu Phe Ser Glu Thr Glu Ala Ala Leu Val
            325                 330                 335

Lys Gly Ser Tyr Asp Phe Leu Gly Leu Asn Tyr Tyr Val Thr Gln Tyr
            340                 345                 350

Ala Gln Asn Asn Gln Thr Ile Val Pro Ser Asp Val His Thr Ala Leu
            355                 360                 365

Met Asp Ser Arg Thr Thr Leu Thr Ser Lys Asn Ala Thr Gly His Ala
370                 375                 380

Pro Gly Pro Pro Phe Asn Ala Ala Ser Tyr Tyr Tyr Pro Lys Gly Ile
385                 390                 395                 400

Tyr Tyr Val Met Asp Tyr Phe Lys Thr Thr Tyr Gly Asp Pro Leu Ile
            405                 410                 415

Tyr Val Thr Glu Asn Gly Phe Ser Thr Pro Gly Asp Glu Asp Phe Glu
            420                 425                 430

Lys Ala Thr Ala Asp Tyr Lys Arg Ile Asp Tyr Leu Cys Ser His Leu
            435                 440                 445

Cys Phe Leu Ser Lys Val Ile Lys Glu Lys Asn Val Asn Val Lys Gly
450                 455                 460

Tyr Phe Ala Trp Ser Leu Gly Asp Asn Tyr Glu Phe Cys Asn Gly Phe
465                 470                 475                 480

Thr Val Arg Phe Gly Leu Ser Tyr Val Asp Phe Ala Asn Ile Thr Gly
            485                 490                 495

Asp Arg Asp Leu Lys Ala Ser Gly Lys Trp Phe Gln Lys Phe Ile Asn
            500                 505                 510

Val Thr Asp Glu Asp Ser Thr Asn Gln Asp Leu Leu Arg Ser Ser Val
```

```
                515                 520                 525
            Ser Ser Lys Asn Arg Asp Arg Lys Ser Leu Ala Asp
                530                 535                 540

<210> SEQ ID NO 44
<211> LENGTH: 444
<212> TYPE: DNA
<213> ORGANISM: Glycine max

<400> SEQUENCE: 44
ggagaggcaa gggaccctcc tccagtatct agacctgtca aaggttttgg ctgggatggc     60
gaagaagatg aagggaaga agacgtggag gaagaggagg acgaagaaga cgagtatgac    120
aagagggtca agaggttca tgcaagtgga gaatttcaaa tcagttaagc actataataa    180
ttcttgtgta cttggttaaa gtattttttt taatgctaga agtcatctat ttatgtgtac    240
tataatttat aataactact actataaacc atcgaggcag cctaacttat ggcactgtcc    300
atgtaatgtg ttagtatttt ttacctgtat catcatcgaa gccgtgtatg agaacagtag    360
ttatctgata acttcaaaat tactcatgcc tgttataaaa aaaaaaaaa aaaaaaaaa    420 aaaaaaaaaa aaaaaaaaa aaaa                                          444

<210> SEQ ID NO 45
<211> LENGTH: 323
<212> TYPE: DNA
<213> ORGANISM: Brassica napus

<400> SEQUENCE: 45
gatgacgcca aaacgcctcc gcctgtttcc agatccattg agggttttgg ctggggagga     60
aagggagacg aagaggaaga agaactggat gaagaggagg tggtggagga agaggaagac    120
gaagaagatg aatatgataa gactgtaaag gaagcacacg caagtggaga agtgtgaatc    180
agttgatttt ttttggtttg ggtatgaaag aaagttgtcg ttggtttgct gaaacttaaa    240
agtctcgttt tattattttt tgtttctcag tttatgtagc tggttggttg gttgagattt    300
aattggttag agaacaaaca gag                                          323

<210> SEQ ID NO 46
<211> LENGTH: 349
<212> TYPE: DNA
<213> ORGANISM: Brassica Napus

<400> SEQUENCE: 46
gatgacgcca aaacgcctcc gcctgtttcc cgttccattg gaggttttgg ctggggagga     60
gagggagatt tagaggggaa agaggaagag gaggtggatg aagaggaggt tgaggaagag    120
gaagacgaag aagatgaata tgataagact gtaaaggaag tacacgcaag cggagaagtg    180
agaatcagtt gaatattttt ttggtttgcg tctctgtaag aaagaagttg tcgttccttt    240
gctgaaacgt aaaagtatct tttttattt tatttgtctt tgccaataac aatgctttgg    300
tttgggttct tgaagatttg taaaattacg cagtataaga agaacaaat               349

<210> SEQ ID NO 47
<211> LENGTH: 385
<212> TYPE: DNA
<213> ORGANISM: Glycine max

<400> SEQUENCE: 47
gttacgagga aacacaaaag gaccaaccaa gccaaagtgt ggaagaaatc atgcagatca     60
```

-continued

```
ttcaagaagc aaggacaaaa atccacactg gtgagcaagc tggcacagga acttcggatg      120
ttgtgcgtgg tgatgaggct aatgaggaag ttgatattaa tgaccactt  gccaaatacc      180 taacccttga ttaatttgtg gttggctaaa ttccctctct ctctatatat atattgttta      240
ccgaagctag tgtgcattct tcgtgtgtat gatatagagt tgaatgagac acaacaactt      300
catcgaattt gaaagttggg ctattttgtt tatcaattat aataagaatt aatttttgtt      360
gtttaaaaaa aaaaaaaaaa aaaaa                                            385
```

<210> SEQ ID NO 48
<211> LENGTH: 8
<212> TYPE: PRT
<213> ORGANISM: Arabidopsis Thaliana

<400> SEQUENCE: 48

Tyr Leu Asp Ala Asn Asp Glu Glu
 1               5

PHOSPHATE STARVATION-INDUCIBLE PROTEINS

BACKGROUND OF THE INVENTION

Phosphorus is one of the most important nutrients for plants. It is essential for their growth and is a structural component of nucleic acids, phospholipids, intermediary metabolites and numerous other biological molecules.

In plants, the only readily absorbed form of exogenous phosphorus is inorganic phosphate ($P_i$) (Bieleski, 1973). When the amount of available phosphate is low, plants are unable to grow vigorously and productively. When phosphate is absent, growth is halted and the plant dies.

Because they are sessile organisms, plants must deal biochemically with environmental stresses such as temperature extremes, nutrient deficiency and drought. This is also true for other photosynthetic organisms which are either sessile or limited in movement. Plants and other photosynthetic organisms, therefore, require signal transduction pathways in order to trigger cellular responses to adverse environmental stimuli.

It has long been known that both temporal and quantitative characteristics of flowering are affected by the level of phosphate in plants relative to the level of nitrogen (Salisbury and Ross, 1985). Relatively high phosphate advances maturity in plants, whereas relatively low phosphate results in little or no flowering taking place. Phosphate levels are also known to affect the biomass ratio between root and shoot. Specifically, phosphate deprivation causes preferential growth of roots (Lefebvre et al., 1982). Thus, in many environments, the availability of phosphorus becomes a major factor limiting the growth and reproduction of photosynthetic organisms.

Numerous groups have investigated the nature of the phosphate-starvation response in plants but despite these studies, little is known of the molecular mechanisms that regulate phosphorus uptake and metabolism. In general, plants exhibit significant morphological and physiological changes in response to perturbations within the environment.

There have been many attempts to identify proteins which are induced under conditions of phosphate starvation. Fife et al. (1990) have conducted in vivo protein labeling studies in *Brassica nigra* cells grown in suspension in either rich or low phosphate medium. Using 2-dimensional gel electrophoresis, they demonstrated the novel synthesis of four proteins under $P_i$ deficiency and one protein in well-nourished cells. Other groups have reported that $P_i$ deprivation increases the synthesis of a plasma membrane protein and a soluble protein in tomato root cultures (Hawkesford and Belcher, 1991), and enhances secretion of six proteins from tomato suspension cells (Goldstein et al., 1989). It has also been shown that a gene for a protein homologous to β-glucosidases is induced to high levels in *B. nigra* suspension cells under $P_i$ starvation (Malboobi and Lefebvre, 1995).

As part of the adenosine nucleotides, ADP and ATP, which are the currency of cellular energy, phosphorus is critical to bioenergetics. Further, the covalent addition or removal of a phosphate group to or from a biological substrate (phosphorylation and dephosphorylation, respectively) often functions as a kind of regulatory "on/off switch" in cellular metabolism and signal transduction. For example, the phosphorylation and dephosphorylation of certain membrane-bound receptor protein kinases and their substrates are key to various signal transduction pathways, including pathways of plant hormones such as ethylene (Kieber et al., 1993) and abscisic acid (Anderberg and Walker-Simmons, 1992). Self-incompatiblity with respect to pollination and fertilization also involves the activity of protein kinases encoded by S-locus genes (Tantikanjana et al., 1993; Zhang and Walker, 1993).

Knowledge of the proteins which affect the uptake and accumulation of phosphorus and which are expressed in phosphate-deficient environments is essential to understand phosphate metabolism and to manipulate the growth and reproduction of photosynthetic organisms for commercial or industrial purposes. Further, the identification and synthesis of the genes which encode such proteins would allow the development of transgenic photosynthetic organisms for many purposes.

SUMMARY OF THE INVENTION

This invention provides the means to modify phosphorus metabolism in plants and other photosynthetic organisms by altering the expression and/or activity of one or more proteins involved in the response of plants or other photosynthetic organisms to phosphorus deprivation. This invention further provides means for more efficient metabolic utilization of phosphorus by plants and other photosynthetic organisms. The compounds of this invention provide the means to change plant morphology by altering phosphorus metabolism. In some applications, the modification will be restricted to seeds, where it can lower the amount of phytate, an anti-nutritive phosphorus storage compound.

This invention relates to isolated DNA (genes) encoding proteins involved in phosphorus uptake and metabolism of plants and other photosynthetic organisms inducible by phosphate deficiency (psr proteins), as well as DNA complementary to these genes, and recombinant DNA constructs and vectors containing DNA encoding such proteins or such complementary DNA, in whole or portions thereof.

In particular, the present invention provides DNA (genes) encoding protein kinases and β-glucosidases of *Arabidopsis thaliana* and *Brassica nigra*, whose transcription is inducible by phosphate starvation, and further provides the RNA so transcribed. The nucleic acids (both DNA and RNA) of this invention encode proteins which differ from other protein kinases in having a unique portion of their amino acid sequence which is different from any other known protein kinase. The β-glucosidases of this invention differ from other known β-glucosidases in sequence and because their level of expression is specifically dependent on phosphate deprivation.

Other nucleic acids of the invention include nucleic acids with sequences complementary to the nucleic acid sequences of *Arabidopsis thaliana* and *Brassica nigra*, or portions thereof; nucleic acids with sequences related to, but distinct from, the nucleic acid sequences of *Arabidopsis thaliana* and *Brassica nigra* and inducible under conditions of phosphate deficiency; and nucleic acid sequences that differ from the nucleic acid sequences of *Arabidopsis thaliana* and *Brassica nigra*, such as modified analogues, due to alteration of the sequence through mutation, substitution, deletion and the like. Primers and probes consisting of 20 or more contiguous nucleotides of the above-described nucleic acids are also included as part of this invention. Homologues and other proteins which are similar in function and are psr proteins are also encompassed by this invention.

Thus, one type of nucleic acid of the invention is an antisense oligonucleotide, a triple helix-forming oligonucleotide, or other oligonucleotide that can be used to inhibit the activity of the psr proteins encoded by the nucleic acids described herein. Such oligonucleotides can block the expression or activity of any of these proteins in a number of ways; for example, preventing transcription of a psr protein-encoding gene by triple helix formation, or by binding to the mRNA transcribed by the gene in any manner that prevents a functional protein from being assembled. Typically, and depending on the mode of action, the oligonucleotides of the invention comprise a specific sequence of about 20 to about 200 or more nucleotides which are identical or complementary to a specific sequence of nucleotides of the psr protein-encoding gene or transcribed mRNA.

The invention further provides nucleic acids of the invention operatively linked to a regulatory sequence, and plasmids or recombinant expression vectors for producing the nucleic acids encompassed by this invention. In a preferred embodiment, a recombinant expression vector, comprising the nucleic acids operatively linked to a regulatory sequence is adapted for transformation of a plant cell.

The invention also provides transgenic cells expressing one or more of the psr proteins of the invention. In a preferred embodiment, the transgenic cells are plant cells. The invention includes transgenic plants produced with nucleic acids or vectors of the invention which express psr proteins provided by the invention. The invention further includes transgenic plant parts, including seeds, as well as tissue culture or protoplasts produced with nucleic acids or vectors of the invention.

The invention also provides a recombinant expression vector adapted for transformation of a plant cell, comprising a DNA molecule operatively linked to a regulatory sequence to allow expression of an RNA molecule that is antisense to a nucleic acid sequence having substantial sequence homology with the nucleotide sequence of SEQ ID NO:1, SEQ ID NO:3, SEQ ID NO:5, SEQ ID NO:7, or SEQ ID NO:9.

The invention further provides a method of preparing a psr protein having psr protein activity using the nucleic acids of the invention. The method comprises culturing a transformant or transgenic cell including a recombinant expression vector comprising a nucleic acid of the invention and a regulatory sequence operatively linked to the nucleic acid in a suitable medium until the psr protein is expressed, and then isolating the psr protein. The invention also provides an isolated psr protein or polypeptide having psr protein activity and substantial sequence homology with either or both of the amino acid sequences shown in SEQ ID NO:2, SEQ ID NO:4, SEQ ID NO:6, SEQ ID NO:8, SEQ ID NO:10, or a portion thereof.

Antibodies and antibody fragments which bind to the novel psr proteins described herein (or to portions of these sequences) are also included in this invention. In a preferred embodiment, the antibody is a monoclonal antibody.

The invention further provides a method for reducing expression of a psr protein of a photosynthetic organism, preferably a plant, comprising the step of incorporating into the organism an isolated nucleic acid which is antisense to a nucleic acid having substantial sequence homology with the nucleotide sequence of a gene encoding a psr protein, especially SEQ ID NO:1, SEQ ID NO:3, SEQ ID NO:5, SEQ ID NO:7, or SEQ ID NO:9.

The methods of this invention can also be used to override dominant alleles thereby producing lowered expression rates or, at an extreme, the "null allele" phenotype. This occurs when a partial or complete complementary sequence to an mRNA is present in the cell. It is generally assumed that, in the presence of antisense RNA, mRNA:antisense hybrids are produced with the result that a substantial reduction in detectable levels of the target gene product is observed. The antisense transcripts can cause a reduction in steady-state sense mRNA levels, perhaps because of increased turnover, or specific duplex attack by double-stranded RNases (Murray and Crockett (1992). The construction of antisense genes must take into consideration that expression levels have to be sufficiently high and be temporally coincident with target gene expression. In addition, in order to avoid the possibility of affecting gene expression at loci of distinct functions, sequence specificity must be assured. This can be achieved by selecting fragments of the nucleic acid sequences encoding psr proteins from translated or from untranslated regions.

The invention further provides a method for reducing expression of a psr protein of a plant, comprising the step of incorporating into a plant, an isolated nucleic acid which causes co-suppression of genes which are identical to or which have substantial sequence homology to the nucleic acid sequences of psr proteins.

The invention further provides a method for lowering or increasing the activity of a par protein of a plant, comprising the step of incorporating into the plant an isolated nucleic acid which causes the production of an altered par protein such that it is either more active, or is dysfunctional and interferes with the native (naturally-occurring) functional psr protein in any way that its activity is reduced.

Thus, this invention provides means for regulating the response of a photosynthetic organism to varying levels of phosphate in its environment as well as a mechanism for modifying the phosphate metabolism of such organisms. This approach to modifying the phosphate pathways of plants has several advantages over traditional plant breeding methods, most importantly, the modifications can be made quickly and specific traits can be modified, even introducing a new trait which is not part of the plant genome.

BRIEF DESCRIPTION OF THE FIGURES

FIG. 5 shows the DNA sequence (SEQ ID NO:1) of phosphate starvation-induced protein kinase psrPK (psr1) from Arabidopsis thaliana and the encoded amino acid sequence of the protein kinase (SEQ ID NO:2).

FIG. 6 is a comparison of the cDNA sequence (SEQ ID NO:1) encoding the phosphate starvation-induced protein kinase psrPK (psr1) from Arabidopsis thaliana with the cDNA sequence (SEQ ID NO:3) encoding a homologous protein kinase from Brassica nigra. Boxed residues indicate conserved nucleotides between the two sequences.

FIG. 7 shows the DNA sequence (SEQ ID NO:1) encoding the phosphate starvation-induced psrPK from Arabidopsis thaliana with its unique 3' terminal sequence capitalized and underlined.

FIG. 8 is a comparison of the amino acid sequences of Arabidopsis thaliana psrPK (psr1) (SEQ ID NO:2) and B. nigra psr1 (SEQ ID NO:4) with the amino acid sequences of other protein kinases SPK3 (SEQ ID NO:28), BSK2 (SEQ ID NO:29), ASK1 (SEQ ID NO:30), ASK2 (SEQ ID NO:31), BSK1 (SEQ ID NO:32), and SPK2 (SEQ ID NO:33).

Figure 11:
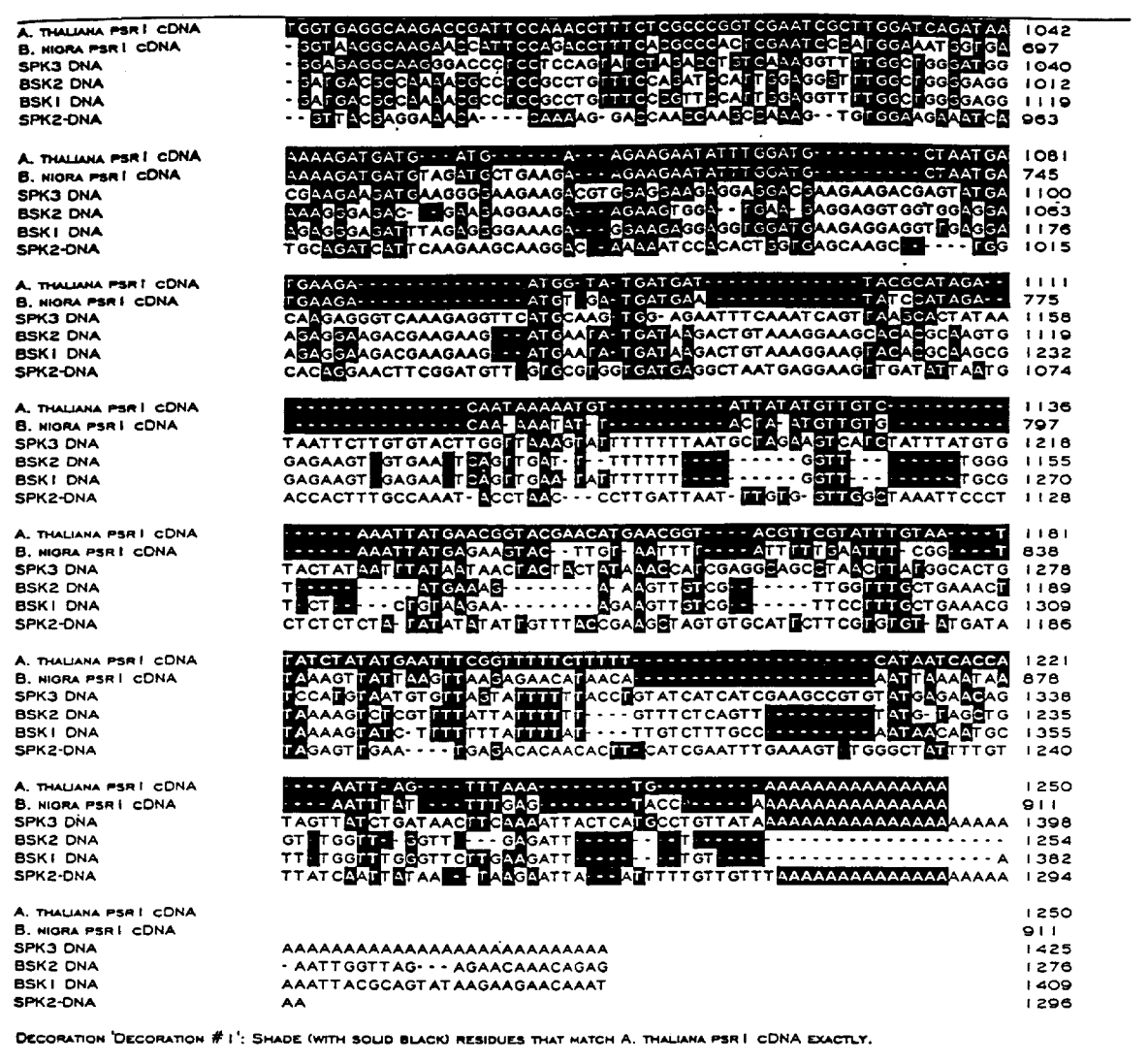

FIG. 11 is a comparison of the 3' end of the cDNA sequences of Arabidopsis thaliana psrPK (psr1) and B. nigra psr1 with the 3' end of the DNA sequences of other protein kinases SPK3 (SEQ ID NO:44), BSK2 (SEQ ID NO:45), BSK1 (SEQ ID NO:46), and SPK2 (SEQ ID NO:47).

FIGS. 14A and 14B show the DNA sequence (SEQ ID NO:5) of phosphate starvation-induced β-glucosidase (psr3.2) from Arabidopsis thaliana and its deduced amino acid sequence (SEQ ID NO:6)

FIG. 15 is the nucleotide (SEQ ID NO:7) and deduced amino acid sequence (SEQ ID NO:8) of Brassica nigra psr3.1 cDNA clone (psr3.1B).

FIG. 16 is the nucleotide (SEQ ID NO:9) and deduced amino acid sequence (SEQ ID NO:10) of Arabidopsis thaliana psr3 .1 cDNA clone (psr3.1A).

Figure 17A:
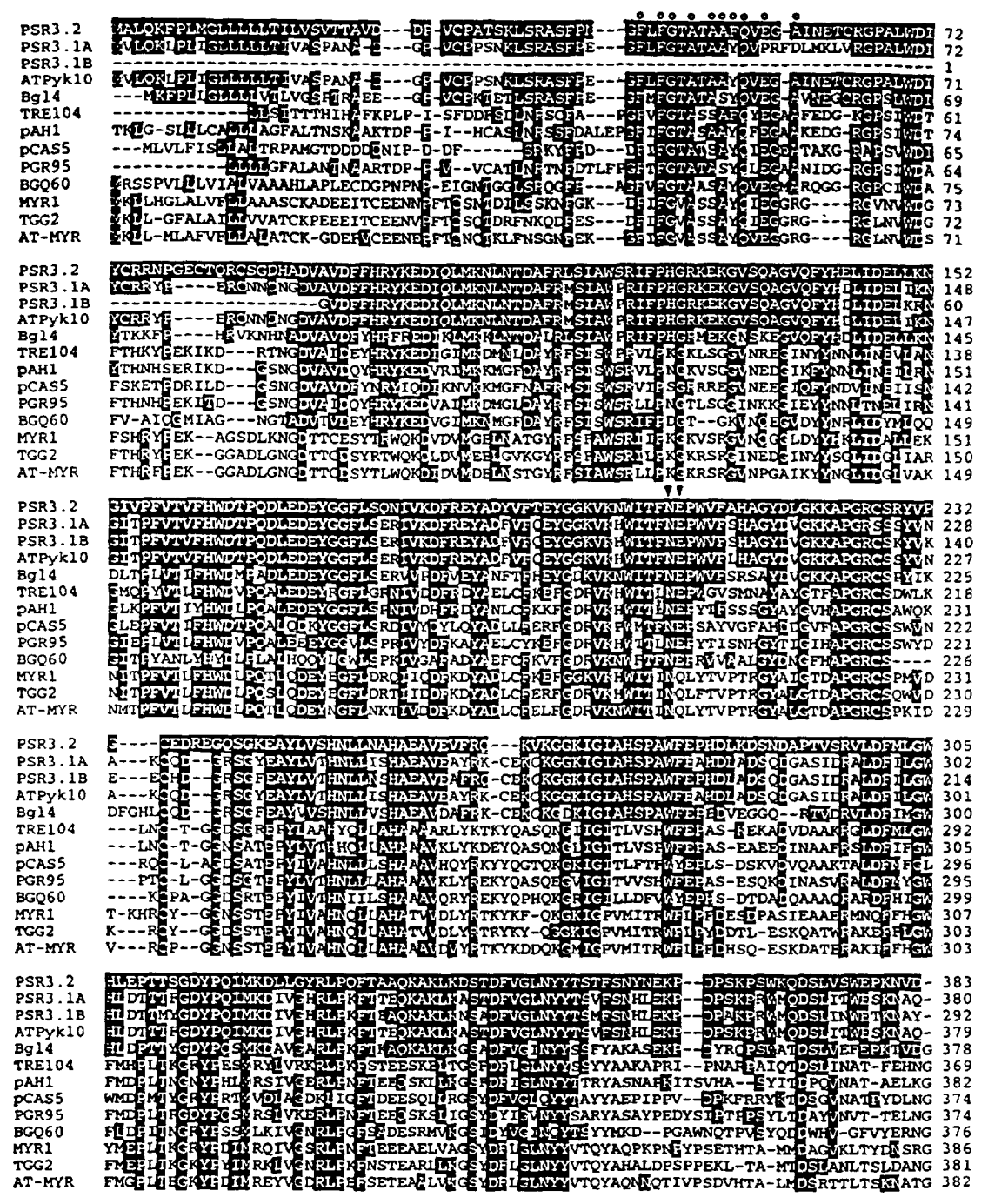

FIGS. 17A and 17B show a comparison of the amino acid sequences of Arabidopsis thaliana psr3.2, psr3.1A, and B. nigra psr3.1B with the amino acid sequences of other plant β-glucosidases ATPyk10 (SEQ ID NO:34), Bgl4 (SEQ ID NO:35), TRE104 (SEQ ID NO:36), pAH1(SEQ ID NO:37), pCAS5 (SEQ ID NO:38), PGR95 (SEQ ID NO:39), BGQ60 (SEQ ID NO:40), MYR1 (SEQ ID NO:41), TGG2 (SEQ ID NO:42), and AT-MYR (SEQ ID NO:43).

FIG. 18 is the partial DNA sequence of psr2 from Brassica nigra T3; SEQ ID NO:11 and T7; SEQ ID NO:12).

FIG. 19 is the partial DNA sequence of psr4 from Brassica nigra T3; SEQ ID NO:13 and T7; SEQ ID NO:14).

FIG. 20 is the partial DNA sequence of psr5 from Brassica nigra T3; SEQ ID NO:15 and T7; SEQ ID NO:16).

FIG. 21 is the partial DNA sequence of psr6 from Brassica nigra T3; SEQ ID NO:17 T7; SEQ ID NO: 18).

FIG. 22 is the partial DNA sequence of psr7 from Brassica nigra T3; SEQ ID NO:19 and T7; SEQ ID NO:20).

FIG. 23 is the partial DNA sequence of psr8 from Brassica nigra T3; SEQ ID NO:21).

FIG. 24 is the partial DNA sequence of psr9 from Brassica nigra T3; SEQ ID NO:22 and T7; SEQ ID NO:23).

FIG. 25 is the partial DNA sequence of psr10 from Brassica nigra T3; SEQ ID NO: 24 and T7; SEQ ID NO:25).

FIG. 26 is the partial DNA sequence of psr11 from Brassica nigra T3; SEQ ID NO:26 and T7; SEQ ID NO:27).

DETAILED DESCRIPTION OF THE INVENTION

Figure 1:
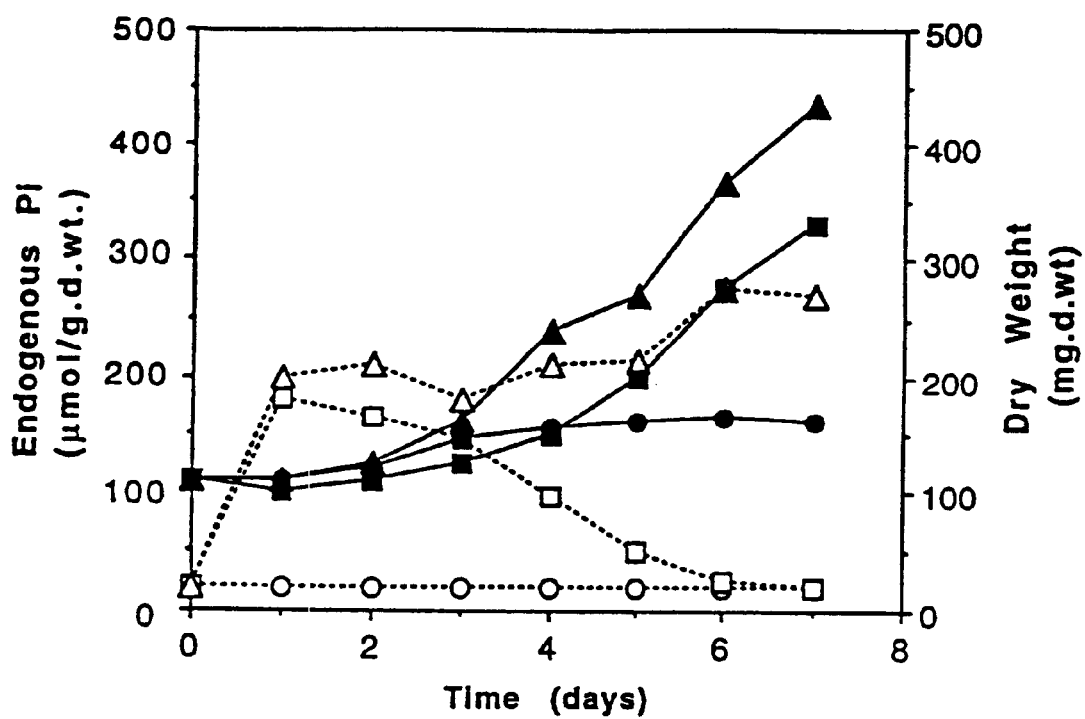
FIG. 1 is a graph of the effect of different $P_i$ treatments on endogenous phosphate content (open symbols) and dry weight accumulation (closed symbols) of Brassica nigra cells during 7 days of growth. Initial concentrations of $P_i$ in the media were zero (○, ●), 1.25 mM (□, ■) and 10 mM (Δ, ▲).

The present invention provides novel methods for producing photosynthetic organisms, especially plants, the organisms so produced and methods of their use. This invention is based, in part, on the discovery that the transcription and expression of several proteins are induced in phosphate-starved cells of photosynthetic organisms. Thus, this invention provides isolated DNA encoding at least a functional portion of a protein (psr protein) of a photosynthetic organism in which transcription of the DNA is induced by phosphate deficiency. In particular, the genes encoding two classes of psr proteins, ser/thr (serine/threonine) protein kinases and β-glucosidases have been isolated and sequenced. As shown in the figures, all nucleic acids which encode psr polypeptides, and homologues of these psr nucleic acids, are encompassed by this invention.

Isolation of clones

As an initial step in the investigation of the $P_i$-starvation response of B. nigra suspension cells, in vitro translations of mRNA extracted from $P_i$-starved and $P_i$-fed cells were compared to investigate if alterations in protein synthesis profiles of B. nigra cells might be controlled at the transcriptional level. First, B. nigra suspension cells were grown in medium containing 1.25 mM $P_i$ for 7 days, so that all cells would be in the same metabolic state. The cells were then subcultured into media with various initial concentrations of $P_i$. Growth conditions for the next 7 days were either severe $P_i$-deprivation (0 $P_i$), mild $P_i$ deprivation (1.25 mM $P_i$) or rich (10 mM $P_i$) (Lefebvre et al.,1990). In mild $P_i$ deprivation, the plant cells absorbed all the $P_i$ by day 2, whereas in the rich conditions, the cells did not take up all the $P_i$ even after 7 days in culture. Total mRNA was isolated from each culture and these isolates were subjected to in vitro translation. The resultant polypeptides were separated on a high resolution SDS-PAGE gel.

Phosphate starvation did not cause gross changes in the protein synthesis profiles of B. nigra (Fife et al., 1990). However, by comparison with the 10 mM $P_i$-fed cells, the inventors consistently isolated lower amounts of RNA from the minus $P_i$-treated cells, indicating a possible decrease in the rate of protein synthesis. This agrees with the high content of free amino acids observed in these cells (Duff et al., 1994).

Figure 2A:
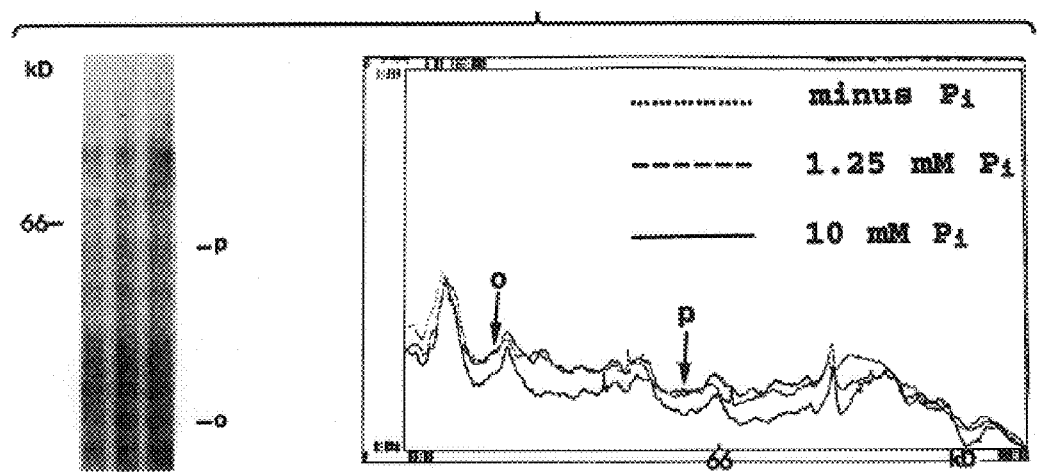
FIG. 2 is a densitometric scan of an autoradiogram of an SDS-polyacrylamide gel of $^{35}$S-labeled in vitro translation products of poly(A)+RNA extracted from B. nigra suspension cells grown for 7 days in MS media containing either no $P_i$ (dotted line), 1.25 mM $P_i$ (dashed line) or 10 mM $P_i$ (solid line). Panel A shows the high molecular weight region of the gel; panel B the medium molecular weight region; and panel C the low molecular weight region. Arrows indicate peaks corresponding to induced polypeptides. Estimated molecular weights are presented on the x-axis.
Figure 2B:
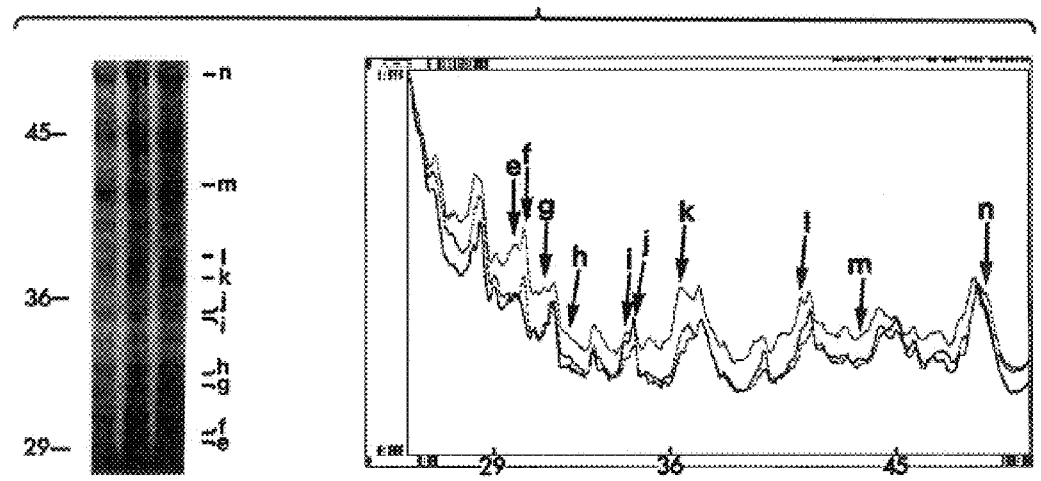
Figure 2C:
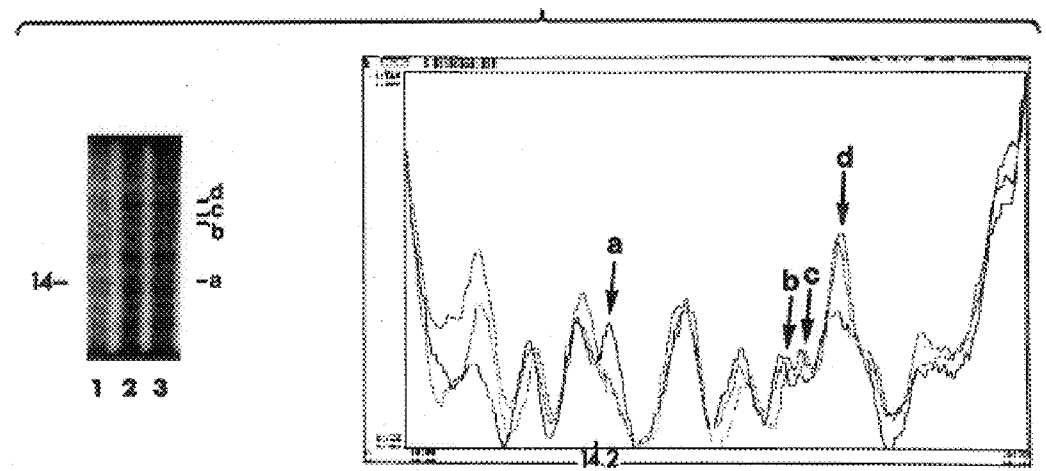

Scanning densitometry of the SDS-PAGE gel identified four polypeptides (approx. 31.7, 32.3, 52.5, and 64.8 kDa) present only in the $P_i$-starved samples (see FIG. 2). These results agree with those of the in vivo protein synthesis analysis of B. nigra suspension cells reported by Fife, et al. (1990). Using 2-dimensional gel electrophoresis, they showed the novel synthesis of four proteins (64 kDa, pI 5.2;

41 kDa, pI 5.6; 27 kDa, pI 5.7; 27 kDa, pI 5.2) under $P_i$ deficiency and one protein (33 kDa, pI 5.1) in well-nourished cells. Acknowledging that such comparisons are at best speculative since post-translational modifications can only be made in living cells, the inducible proteins reported by Fife et al. possess similar sizes to those detected in this study.

A cDNA library was constructed from mRNA isolated from the severely deprived *B. nigra* cells. Screening by differential hybridization was performed on this CDNA library using cDNA probes prepared from minus $P_i$-treated and 10 mM $P_i$-fed (well-fed) *B. nigra* cells. A number of clones representing mRNA species preferentially transcribed under $P_i$-deficiency were identified. These phosphate-starvation responsive (psr) clones (121 clones) were placed into eleven different homology groups as determined by cross-hybridization. Northern blots showed that the expression of each of the eleven distinct groups of genes is controlled at the level of transcription (Malboobi and Lefebrve, 1995). The Northern blots showed that corresponding genes are inducible in both mild and severe $P_i$-starvation conditions; that is, possible side effects of extremely stressful conditions leading to cell death on the induction of these genes can be ruled out.

Figure 3:
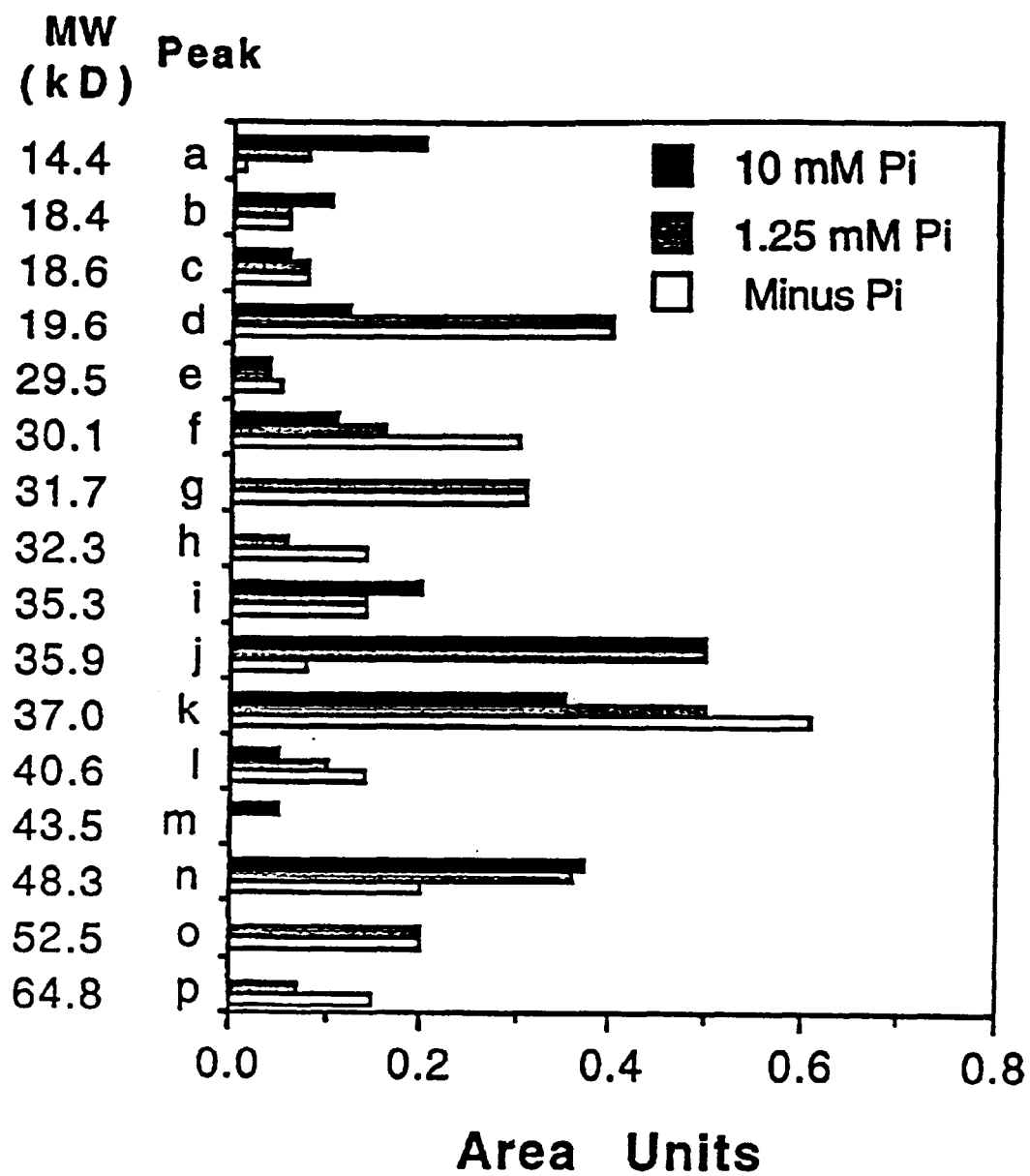
FIG. 3 is a histogram showing the relative amounts of differentially expressed mRNA species in B. nigra suspension cells cultured in various concentrations of $P_i$. The length of each bar represents the area under the corresponding peak and, therefore, the relative abundance of the mRNA species. Peak designations are as in FIG. 2. Estimated molecular weights are presented on the y-axis.

As shown in FIG. 3, the expression of certain genes (grey bars) was also induced in the 7-day old 1.25 mM $P_i$-fed cells that had undergone mild $P_i$ deprivation. The corresponding-protein sizes are approximately 31.7, 32.3, 52.5 and 64.8 Kd. If in vitro transcription rates are independent of message type, then the levels of de novo expression of four of the differentially expressed messages in minus $P_i$-treated cells were relatively high, comparable to those of the most abundant mRNAs in these cells. Based on expression patterns, the proteins encoded by these genes play active metabolic and structural roles in cellular adaptation to $P_i$ stress.

Identification and Characterization of Phosphate-inducible genes: Protein Kinase psr genes DNA sequencing and subsequent analysis permitted the identification of one of the genes, psrPK (psr1), as a protein kinase (SEQ ID NO:3) whose expression is induced in phosphate-starved *Brassica nigra* cells. A homologue (SEQ ID NO:1) which is also differentially expressed under $P_i$ deprivation was identified and isolated from *A. thaliana*.

The induced *Arabidopsis thaliana* gene encodes a polypeptide designated psrPK (or psr1) which, along with the *B. nigra* polypeptide, has regions of high homology to other protein kinases (see Example 9 and FIG. 8, infra), and possesses serine/threonine (ser/thr) protein kinase activity. However, *A. thaliana* psrPK and its *B. nigra* homologue are different from previously described protein kinases because they have a unique C-terminal region of the protein kinase. This unique region could be involved in $P_i$ concentration detection or in receiving or delivering signals, or more than one of these functions. The protein kinases substrates could be other components of the phosphate-starvation response pathway or enzymes involved in the response itself. These proteins have no apparent N-terminal signal peptide, organellar targeting sequence or membrane spanning regions, which indicates they probably function in the cytoplasm of the cell.

Protein kinases catalyze phosphorylation of protein substrates and are found in all living organisms. They are known to be involved in regulatory processes, wherein phosphorylation/dephosphorylation functions as a type of switch for the activation/deactivation (or vice versa) of the substrate protein. Certain types of protein kinases are involved in the phosphate starvation response of fungi and bacteria; however, this is the first time that a plant protein kinase has been shown to be inducible to high levels under $P_i$ starvation. Because psrPK is particularly active during periods when phosphate is unavailable, it is probable that it has a switch-like role in the control of the plant response to phosphate deprivation. The psrPK protein is homologous to SNF1, which is expressed in carbon-starved bacteria and has been shown to be involved in governing metabolic reactions under such conditions. Thus, modulation of the expression of the psrPK kinase could alter the expression of whole pathways involved in phosphate metabolism, thereby producing valuable phenotypes.

Identification and Characterization of Phosphate-inducible genes: β-glucosidase psr genes One homology group (psr3) of phosphate-starvation responsive CDNA clones from *Brassica nigra* was determined to contain a β-glucosidase based on a portion of the polypeptide sequence (Malboobi and Lefebvre, 1995). The DNA sequence (SEQ ID NO:7) encoding this phosphate starvation-induced β-glucosidase (psr 3.1B) from *Brassica nigra* and the amino acid sequence (SEQ ID NO:8) of the full-length psr3.1B protein is shown in FIG. 15.

Southern blots of *Arabidopsis thaliana* genomic DNA probed with the psr3.1 CDNA indicated that this gene exists as a single locus. A genomic library of *A. thaliana* was screened at high stringency to isolate the corresponding genomic clone. The resultant clone was designated psr3.2 (SEQ ID NO:5) because of its sequence divergence from isolated psr3.1 cDNA clones. Northern blotting with probes derived from the coding region of the genomic clone showed that this gene is expressed at high levels in $P_i$-starved roots and enhancement occurs within two days of growth in medium lacking $P_i$. The expression of this gene is repressed by heat shock and anaerobic conditions, and it is not significantly induced by high salinity, or by nitrogen or sulphur deprivation. Sequence analysis of the genomic clone revealed the existence of thirteen exons interrupted by twelve AT-rich introns and shows high homology with the *B. nigra* psr3.1B, as well as various other β-glucosidase genes from other species. Sequence similarity and divergence percentages between the deduced amino acid sequences of the psr3 clones and other β-glycosidases suggests that these genes should be included along with two other Brassicaceae genes in a distinct subfamily of the BGA glycosidase gene family. The presence of an endoplasmic reticulum retention signal at the carboxy terminus indicates that this is the cellular location of psr3.2. The possible metabolic and regulatory roles of this enzyme during the $P_i$-starvation response are described infra.

Identification and Characterization of Phosphate-inducible genes: Other Related psr genes DNA sequencing and computer analysis for the remaining nine psr clones was performed using the techniques described in Example 8. Genomic libraries of other species were screened as described in Example 9 to identify homologues of the genes.

The DNA sequence of psr2 from *Brassica nigra* most closely resembles a glutamate dehydrogenase at the T3 portion of the sequence and an ovomucoid protein at the T7 portion of the sequence (FIG. 18).

The DNA sequence of psr4 from *Brassica nigra* most closely resembles an envelope protein (FIG. 19).

The DNA sequence of psr5 from *Brassica nigra* most closely resembles an aspartate kinase (FIG. 20). This sequence shows some homology to disintegrin, another aspartate kinase, which inhibits the signal transduction pathway for the cell cycle.

The DNA sequence of psr6 from *Brassica nigra* most closely resembles a phosphate transporter protein (FIG. 21).

The DNA sequence of psr7 from *Brassica nigra* most closely resembles a histidine kinase at the T3 portion of the sequence and a skeletal muscle calcium release channel protein psr7 at the T7 portion of the sequence (FIG. 22).

The DNA sequence of psr8 from *Brassica nigra* most closely resembles a sugar transporter protein is shown in FIG. 23.

The DNA sequence of psr9 from *Brassica nigra* most closely resembles an adenylate cyclase (FIG. 24).

The DNA sequence of psr10 from *Brassica nigra* most closely resembles a calcium channel protein (G-protein) (FIG. 25).

The DNA sequence of psr11 from *Brassica nigra* most closely resembles a phosphatidylinositol kinase at the T3 portion of the sequence and a tripeptidyl peptidase protein at the T7 portion of the sequence (FIG. 26).

Isolated Nucleic Acids and Constructs

This invention provides isolated DNA or recombinant nucleic acids encoding a protein, or a functional portion thereof, of a-photosynthetic organism wherein transcription (or translation) of the DNA or nucleic acid is induced by phosphate deficiency. In a preferred embodiment the protein has protein kinase activity, especially ser/thr protein kinase activity, or β-glucosidase activity. The term "nucleic acid" includes DNA and RNA, as well as single-stranded and double-stranded species.

DNA or nucleic acids referred to herein as "isolated" are DNA or nucleic acids separated away from the nucleic acids of the genomic DNA or cellular RNA of their source or origin (e.g., as it exists in cells or in a mixture of nucleic acids such as a library), and may have undergone further processing. "Isolated" DNA or nucleic acids include DNA or nucleic acids obtained by methods described herein, similar methods or other suitable methods, including essentially pure DNA or nucleic acids, DNA or nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells on nucleic acids designed to allow and make probable a desired recombination event.

The isolated DNA can comprise: (a) SEQ ID NO:1, SEQ ID NO:3, or a truncated nucleic acid sequence which encodes a functional portion of the protein encoded by SEQ ID NO:1 or SEQ ID NO:3 or (b) a nucleic acid sequence having at least 80% homology to SEQ ID NO:1, SEQ ID NO:3, or a truncated nucleic acid sequence which encodes a functional portion of the protein encoded by a nucleic acid sequence having at least 80t homology to SEQ ID NO:1 or SEQ ID NO:3; or (c) a nucleic acid which is complementary and hybridizes under moderately stringent conditions to any of the sequences of (a) or (b). A "functional portion" means a portion of a psr protein which when expressed will affect the phosphate uptake and/or metabolism of the native (naturally-occurring) photosynthetic organism in which the endogenous psr protein is produced. A preferred embodiment is a truncated DNA sequence comprising isolated DNA consisting of nucleotide residues 984 to 1240 of SEQ ID NO:1, encoding the unique region of the protein kinase or a nucleic sequence encoding YLDANCE (SEQ ID NO:48). Further provided is DNA or RNA having 50% homology or which hybridizes under moderately stringent conditions to the DNA of claim 3. Truncated nucleic acid sequences of the above-described DNA or nucleic acids which consist of 10–20 or more contiguous nucleotides are also provided and can find use as probes and primers.

One cDNA of this invention is shown in FIG. 5 (SEQ ID NO:1) and comprises a 1020 nucleotide open reading frame, bounded by ATG start and TAG stop codons, encoding 339 amino acids. The cDNA further comprises 89 bp 5' untranslated nucleotides and 141 bp 3' untranslated nucleotides, including a 3' polyA tail for a functional mRNA. The protein encoded by this cDNA is discussed in detail below.

The isolated DNA of this invention further comprises: (a) SEQ ID NO:5, SEQ ID NO:7, SEQ ID NO:9, or a truncated nucleic acid sequence which encodes a functional portion of the protein encoded by SEQ ID NO:5, SEQ ID NO:7, or SEQ ID NO:9; or (b) a nucleic acid sequence having at least 80% homology to SEQ ID NO:5, SEQ ID NO:7, SEQ ID NO:9, or a truncated nucleic acid sequence which encodes a functional portion of the protein encoded by a nucleic acid sequence having at least 80% homology to SEQ ID NO:5, SEQ ID NO:7, or SEQ ID NO:9; or (c) a nucleic acid which is complementary and hybridizes under moderately stringent conditions to any of the sequences of (a) or (b). Polypeptides encoded by these nucleic acids are also encompassed by this invention. Further, an isolated nucleic acid encoding a protein having β-glucosidase activity and an amino acid sequence with at least 80% sequence homology with SEQ ID NO:5 or 50% homology with SEQ ID NO:6 is also provided. Truncated nucleic acid sequences of the above-described DNA or nucleic acids which consist of 10–20 or more contiguous nucleotides are also provided and can find use as probes and primers.

For the purposes of this disclosure, the term "homology" does not refer to common evolutionary origin, but rather to similarity between sequences. The degree of homology between two sequences can be determined by optimally aligning the sequences for comparison, as is commonly known in the art, and comparing a position in the first sequence with a corresponding position in the second sequence. When the compared positions are occupied by the same nucleotide or amino acid, as the case may be, the two sequences are homologous at that position. The degree of homology between two sequences is expressed as a percentage representing the ratio of the number of matching or homologous positions in the two sequences to the total number of positions compared.

The term "having substantial sequence homology" is understood to mean that the sequence in question has slight or insignificant sequence variations from, for example, the sequences of SEQ ID NO:1, SEQ ID NO:3, SEQ ID NO:2 or SEQ ID NO:4. That is, a nucleic acid sequence "having substantial sequence homology" to SEQ ID NO:1 or SEQ ID NO:3 encodes substantially the same protein product as the actual sequence; i.e., a protein kinase having a regulatory function in phosphate metabolism. It is expected that certain substitutions or other alterations will be able to be made in various portions of SEQ ID NO:1 or SEQ ID NO:3 which do not significantly affect protein function. The sequence variations may derive from mutation. Further, a protein having a homologous sequence to that of SEQ ID NO:2 or SEQ ID NO:4 would have a similar catalytic activity to that of the protein whose sequence is shown in SEQ ID NO:2 or SEQ ID NO:4. Alternatively, isoforms of the protein of SEQ ID NO:2 or SEQ ID NO:4 that have protein kinase activity could exist. For example, a sequence having substantial homology to that of SEQ ID NO:2 can be a homologue from another plant variety or species, as is SEQ ID NO:4. Such isoforms and homologous proteins may be immunologically cross-reactive.

It is expected that a nucleic acid encoding a protein comprising an amino acid sequence having about 80% homology with the amino acid sequence of SEQ ID NO:2 or SEQ ID NO:4, or about 50% homology with the amino acid residues 190 to 340 of SEQ ID NO:2, will produce a functional protein kinase, and the invention provides such a nucleic acid. Proteins comprising an amino acid sequence that is about 60%, 70%, 80% or 90% homologous with the amino acid sequence of SEQ ID NO:2 or SEQ ID NO:4, or greater, are also expected to have protein kinase activity.

The invention encompasses isolated nucleic acids encoding a protein having protein kinase activity, and having a sequence that differs from the nucleotide sequence of SEQ ID NO:1 or SEQ ID NO:3 due to degeneracy in the genetic code. "Degeneracy" is understood to mean that each of several different amino acids is designated by more than one nucleotide triplet or codon. For example, AAA and AAG each code for lysine. This is an example of a "silent mutation" occurring in the third (or "wobble") nucleotide of a codon wherein the amino acid encoded remains the same.

The invention also encompasses mutations that are not silent or other alterations wherein at least 80% amino acid homology with SEQ ID NO:2 or SEQ ID NO:4, or at least 50% homology with amino acid residues 190 to 340 of SEQ ID NO:2, is maintained.

It would be understood by a person skilled in the art that the invention includes different forms of the nucleic acids of the invention arising from alternative splicing of an mRNA corresponding to a cDNA of the invention.

The invention further provides a nucleic acid that hybridizes under high or moderate stringency conditions to a nucleic acid encoding at least a portion of the amino acid sequence shown in SEQ ID NO:2 or SEQ ID NO:4. Stringency conditions for hybridization is a term of art which refers to the conditions of temperature and buffer concentration which permit hybridization of a particular nucleic acid to another nucleic acid in which the first nucleic acid may be perfectly complementary to the second, or the first and second may share some degree of complementarity which is less than perfect. See, sections 2 and 6 in *Current Protocols in Molecular Biology* (Ausubel, F. M. et al., eds., Vol. 1, Supplement 29, 1995). Hybridization conditions are described generally in Maniatis et al., 1982 and Sambrook et al., 1989.

High stringency hybridization procedures, for example, can (1) employ low ionic strength and high temperature for washing, such as 0.015 M NaCL/0.0015 M sodium citrate, pH 7.0 (0.1× SSC) with 0.1% sodium dodecyl sulfate (SDS) at 50° C.; (2) employ during hybridization, 50% (vol/vol) formamide with 5× Denhardt's solution (0.1% weight/volume highly purified bovine serum albumin/0.1% wt/vol Ficoll/0.1% wt/vol polyvinylpyrrolidone), 50 mM sodium phosphate buffer at pH 6.5 and 5× SSC at 42° C.; or (3) employ hybridization with 50% formamide, 5× SSC, 50 mM sodium phosphate (pH 6.8), 0.1% sodium pyrophosphate, 5×Denhardt's solution, sonicated salmon sperm DNA (50 $\mu$g/ml), 0.1% SDS, and 10% dextran sulfate at 42° C., with washes at 42° C. in 0.2× SSC and 0.1% SDS.

By varying hybridization conditions from a level of stringency at which no hybridization occurs to a level at which hybridization is first observed, conditions which will allow a given sequence to hybridize with the most similar sequences in the sample can be determined.

This invention also provides nucleic acids and polypeptides with structures that have been altered by different means, including but not limited to, alterations using transposons, site-specific and random mutagenesis, and engineered nucleotide substitution, deletion, or addition.

Proteins

This invention also relates to psr proteins or psr polypeptides, for example the proteins encoded by SEQ ID NO:1, SEQ ID NO:3, SEQ ID NO:5, SEQ ID NO:7, SEQ ID NO:9, or homologous nucleic acids. As shown in the figures, all psr polypeptides and homologues are encompassed by this invention.

The proteins and polypeptides of the present invention can be isolated and/or recombinant. Proteins or polypeptides referred to herein as "isolated" are proteins or polypeptides purified to a state beyond the naturally-occurring state in which they exist endogenously in cells. A preferred embodiment is an essentially pure protein or polypeptide free of other proteins or polypeptides. "Isolated" proteins or polypeptides include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Proteins or polypeptides referred to herein as "recombinant" are proteins or polypeptides produced by the expression of recombinant nucleic acids.

The transcription of these proteins is induced under conditions of phosphate deficiency and the proteins have protein kinase activity. Preferably, the amino acid sequence of these proteins shows at least 80% sequence homology with SEQ ID NO:2, SEQ ID NO:4, SEQ ID NO:6, or 50% homology with amino acid residues 190 to 340 of SEQ ID NO:2.

Isolation of Homologues

Nucleic acids or portions thereof provided by this invention can be used to isolate homologous nucleic acids from cells of other species of photosynthetic organisms which contain genes encoding one or more psr proteins similar in function to the nucleic acids of this invention. The term "psr protein" means a protein whose expression is induced to higher levels under conditions of phosphate deficiency than under conditions of phosphate sufficiency. The protein may not be expressed at all if the cell has adequate levels of available phosphate. Further such a protein is not associated with mechanisms which bring about cell death.

As described in the examples below, the inventors have isolated nucleic acids of the invention using *B. nigra* suspension cells as starting material. In brief, the inventors created a cDNA library from *B. nigra* suspension cells that had been starved for phosphate for seven days. The library was screened using two sets of cDNA probes generated from *B. nigra* suspension cells that had been grown under conditions of no phosphate or 5 mM phosphate, respectively. Clones that hybridized strongly to the first set of probes, but not the second set, were isolated. The cDNA inserts of these clones were subjected to dideoxy nucleotide sequencing (Sanger, 1981) to determine nucleotide sequence, and amino acid sequence was predicted therefrom. The psrPK gene was recognized to encode a novel protein kinase. Other differential hybridization, cloning and sequencing methods are known to those skilled in the art, and can be employed to obtain the protein kinase genes isolated by the inventors or homologues thereof.

Alternatively, a nucleic acid of the invention can be isolated in the following manner. A nucleic acid probe comprising at least a portion of the sequence of SEQ ID NO:1 or a homologue is chemically synthesized or prepared using recombinant DNA techniques. The probe is radiolabelled and used to screen a cDNA or genomic DNA library according to standard techniques. It can be prepared from B. nigra, a different organism or another source having a homologue or transgene of the invention that could be identified under appropriate hybridization conditions. The DNA identified by screening the library is then cloned and sequenced using standard techniques.

A third alternative method for isolating a nucleic acid of the invention is to isolate or chemically synthesize a peptide of the protein kinase and use this peptide to produce an antibody to the protein kinase in an animal. The antibody is then used according to standard techniques to screen a cDNA library, from B. nigra or another source, for immunoreactive clones. DNA from such clones are then sequenced as is known in the art.

A fourth alternative method for isolating a nucleic acid of the invention is to selectively amplify such a nucleic acid using polymerase chain reaction (PCR) (Saiki et al., 1985; Konat et al., 1991) and DNA or RNA as a template. In the latter case, total mRNA may be isolated from cells using one of the methods common in the art, described in Maniatis et al., 1982. The retroviral enzyme reverse transcriptase is then used to synthesize cDNA complementary to the mRNA. Appropriate oligonucleotide primers for the amplification of the chosen nucleic acid are designed and synthesized, and PCR performed on a mixture of the primers and cDNA using standard technology (Innis et al., 1990). The PCR protocol can additionally include 5' or 3' RACE (rapid amplification of cDNA ends) methodology (Innis et al., 1990). The amplified DNA fragment produced is cloned into an appropriate vector.

An RNA molecule of the invention can also be constructed by cloning an appropriate cDNA or an amplified DNA molecule as described above into one of the commonly available transcription vectors. The DNA would usually be cloned downstream of a promoter, for example, the SP6 promoter of the vector PGEM 3Z (Promega, Madison, Wis.), the appropriate RNA polymerase (in this example, SP6 polymerase) added, and transcription reactions performed according to the manufacturer's specifications. Other useful promoters carried by commonly used transcription vectors are the bacteriophage T7 and T3 promoters.

Another well-known method of producing a nucleic acid or oligonucleotide of the invention is chemical synthesis. Various machines for DNA synthesis are well-known in the art, such as, for example, those sold by Applied Biosystems, Inc. of Foster City, Calif. and by Millipore Corp. of Bedford, Mass. and can be used for such syntheses.

Alteration of Protein Expression with Recombinant Expression Vectors

Alteration of psrPK expression can be achieved in a variety of ways. In one embodiment, recombinant nucleic acids are constructed in which psrPK is operatively linked to regulatory sequences, such as promoters, that control the level, timing or tissue-specificity of gene expression.

Standard recombinant DNA techniques can be employed to engineer a recombinant expression vector including a nucleic acid of the invention that allows expression of at least a portion of a protein kinase of the invention. See, e.g., Sambrook, et al., 1989. The engineered vector would also include a regulatory sequence "operatively linked" to the nucleic acid of the invention to allow such expression. For the purposes of this disclosure, the term "regulatory sequence" includes promoters, enhancers and other sequences that control expression or message stability, as are well-known in the art. Examples of known promoters suitable for these purposes are given infra. Those of skill in the art can recognize that these examples are not limiting and other promoters can be adapted for particular purposes of modulating the phosphate uptake and metabolism of photosynthetic organisms.

In some cases, the regulatory element can provide tissue-specific expression. The two-part term "operatively linked" means both that the regulatory sequence contains sufficient element(s) to allow expression of the nucleic acid in question and that the nucleic acid is linked to the regulatory sequence appropriately. For example, the nucleic acid of the invention is in the appropriate orientation and in phase with an initiation codon.

In the context of this disclosure, the term "promoter" or "promoter region" refers to a sequence of DNA, usually upstream (5') to the coding sequence of a structural gene, which controls the expression of the coding region by providing recognition and binding sites for RNA polymerase and/or other factors required for transcription to start at the correct site.

There are generally two types of promoters, constitutive and inducible promoters. The term "constitutive" as used herein does not necessarily indicate that a gene is expressed at the same level in all cell types, but that the gene is expressed in a wide range of cell types, although some variation in abundance is often detected.

An inducible promoter is a promoter that is capable of directly or indirectly activating transcription of one or more DNA sequences or genes in response to an inducer. In the absence of an inducer the DNA sequences or genes will not be transcribed. Typically a protein factor (or factors), that binds specifically to an inducible promoter to activate transcription, is present in an inactive form which is then directly or indirectly converted to an active form by the inducer. The inducer can be a chemical agent such as a protein, metabolite, growth regulator, herbicide or phenolic compound, or a physiological stress imposed directly by heat, cold, salt, or toxic elements or indirectly through the action of a pathogen or disease agent such as a virus. The inducer can also be an illumination agent such as light, darkness and light's various aspects which include wavelength, intensity, fluence, direction and duration. A cell containing an inducible promoter may be exposed to an inducer by externally applying the inducer to the cell or plant such as by spraying, watering, heating or similar methods. If it is desirable to activate the expression of a gene at a particular time during plant development, the inducer can be so applied at that time.

Examples of such inducible promoters include heat shock promoters, such as the inducible hsp70heat shock promoter of *Drosphilia melanogaster* (Freeling, et al., 1985; a cold inducible promoter, such as the cold inducible promoter from B. napus (White, et al., 1994,); and the alcohol dehydrogenase promoter which is induced by ethanol (Nagao, et al., 1986).

Among sequences known to be useful in providing for constitutive gene expression are regulatory regions associated with Agrobacterium genes, such as nopaline synthase (Nos), mannopine synthase (Mas) or octopine synthase (Ocs), as well as regions regulating the expression of viral genes such as the 35S and 19S regions of cauliflower mosaic virus (CaMV) (Brisson, et al. 1984), or the coat promoter of TMV (Takamatsu, et al., 1987).

Other useful plant promoters include promoters which are highly expressed in phloem and vascular tissue of plants such as the glutamine synthase promoter (Edwards, et al., 1990) the maize sucrose synthetase 1 promoter (Yang et al., 1990), the promoter from the Rol-C gene of the TLDNA of Ri plasmid (Sagaya, et al., 1989), and the phloem-specific specific region of the pRVC-S-3A promoter (Aoyagi, et al., 1988). Alternatively, plant promoters such as the small subunit of Rubisco (Rbcs) promoter (Coruzzi, et al., 1984; Broglie, et al., 1984), or heat shock promoters, e.g., soybean HPS17.5-E or HPS17.3-B (Gurley, et al., 1986) can be used.

Other promoters which can be used according to the present invention include, but are not limited to:

(a) low temperature and ABA-responsive promoters, such as Kin1, cor6.6 (Wang et al., 1995; Wang and Cutler, 1995) and the ABA inducible promoter from EM gene wheat (Marcotte Jr. et al., 1989).

(b) phloem-specific sucrose synthase promoters, such as the ASUS1 promoter from Arabidopsis (Martin et al., 1993);

(c) root and shoot promoters, such as the ACS1 promoter (Rodrigues-Pousada et al., 1993);

(d) seed-specific promoters, such as the 22 kDa zein protein from maize (Unger et al., 1993) the psi lectin promoter from pea (de Pater et al., 1993), the phaseolin promoter from Phaseolus vulgaris (Frisch et al., 1995);

(e) late-embryo-abundant promoters, such as the lea promoter (T. L. Thomas, 1993);

(f) fruit-specific promoters, such as the E8 gene promoter from tomato, (Cordes et al., 1989);

(g) meristematic tissue-specific promoters such as the PCNA promoter (Kosugi et al., 1995);

(h) pollen-specific promoters, such as the NTP303 promoter (Weterings et al., 1995);

(i) late embryogenesis stage-specific promoters, such as the OSEM promoter (Hattori et al., 1995);

(j) ADP-glucose pyrophosphorylase tissue-specific promoters for guard cells and tuber parenchyma cells, such as the ADP GP from potato (Muller-Rober et al., 1994);

(k) conductive tissue-specific promoters, such as the Myb promoter from barley (Wissenbach et al., 1993); and (l) Plastocyanin promoters in young green tissues, such as the plastocyanin promoter from Arabidopsis (Vorst et al., 1993).

Depending on the type of regulatory sequence employed, a plant transformed with a recombinant nucleic acid of this invention would over- or under-express a psr protein, either in chosen plant parts or throughout the plant, and/or at different times in the life history of the plant. Changes in plant size, relative sizes of different plant parts, time of flowering, level of phytate, starch and oil accumulated in seeds, or other phenotypic characteristics can thus be engineered.

Numerous recombinant expression vectors are known that are suitable for expression in a variety of cell types. A recombinant expression vector can be engineered for expression of a psr protein, such as psrPK, in prokaryotic cells, for example, *Escherichia coli,* or in eukaryotic cells, for example, *Saccharomyces cerevisiae* (yeast) and *Arabidopsis thaliana,* tobacco or canola. The recombinant expression vector can be a plasmid, a bacteriophage or a virus. Plant gene constructs of the present invention can be introduced using Ti plasmids, Ri plasmids, plant virus vectors, direct DNA transformation, microinjection, electroporation, and the like, as described, supra. Common expression vectors often include a marker gene that permits easy screening for transformed cells. Some common vectors also include a sequence encoding at least a portion of another functional protein, such as firefly luciferase or bacterial β-galactosidase. In a scheme employing this kind of vector, a nucleic acid of the invention would be linked in frame to this coding sequence such that a fusion protein would be produced comprising at least a portion of the protein kinase of the invention and the other functional protein. Cells transformed with the engineered vector could be screened for expression of the luciferase, β-galactosidase or other fused protein. Alternatively, the other protein fused to the protein kinase may not be useful for screening, but can instead provide a useful property such as increased solubility, or can be exploited in a protein purification scheme or in industrial applications such as the addition of purified enzyme to a reaction.

Accordingly, the inventors vectors can be constructed containing nucleic acids encoding a psr protein with which to transform a wide variety of crop and horticultural plants, including monocots, dicots and gymnosperms. Modification can be targeted to the whole plant, or a specific tissue, organ or plant part, such as a seed. Further, expression of the gene can be limited to particular developmental stages or environmental conditions. The gene delivery systems used to incorporate the constructs will vary depending on the target plant species; however, those of skill in the art can recognize that present molecular techniques can be applied to successfully modify particularly useful crop plants, such as rice, wheat-, barley, rye, corn, soybeans, canola, sunflower, potato, carrots, sweet potato, beans, peas, lettuce, cabbage, cauliflower, broccoli, turnip, radish, spinach, onion, garlic, pepper, carrots, pumpkins, cucumber, apples, pears, melons, plum, cherry, peaches, nectarines, apricot, strawberry, grape, raspberry, pineapple, tobacco, bananas, sorghum, sugarcane, and the like.

For example, several plant species, canola, tobacco and Arabidopsis, have been genetically engineered to include vectors designed both to lower and to increase the amount of protein kinase within the entire plant or in the developing seeds.

In one embodiment, eight different constructs were incorporated into Arabidopsis cells with either constitutive (CaMV 35S) or seed-specific (Arabin) promoters. These constructs are described in Table 1 below.

TABLE 1

| Construct | Promoter | A. thaliana protein kinase | sense/ antisense |
| --- | --- | --- | --- |
| 1 | Constitutive | complete gene sequence | sense |
| 2 | Seed-specific | complete gene sequence | sense |
| 3 | Constitutive | complete gene sequence | antisense |
| 4 | Seed-specific | complete gene sequence | antisense |
| 5 | Constitutive | truncated gene sequence | sense |
| 6 | Seed-specific | truncated gene sequence | sense |
| 7 | Constitutive | truncated gene sequence | antisense |
| 8 | Seed-specific | truncated gene sequence | antisense |

The first four of these constructs containing complete gene sequence are depicted in FIGS. 12A–12D.

Transformant Cells

The invention provides host cells transformed with a recombinant expression vector of the invention. For the purposes of this disclosure, the terms "transformed with", "transformant", "transformation", "transfect with", "transformant" and "transfection" all refer to the introduction of a nucleic acid into a cell by one of the numerous methods known to persons skilled in the art. Transformationof prokaryotic cells, for example, is commonly achieved by treating the cells with calcium chloride so as to render them "competent" to take up exogenous DNA, and then mixing such DNA with the competent cells. Prokaryotic cells can also be infected with a recombinant bacteriophage vector.

Nucleic acids can be introduced into cells of higher organisms by viral infection, bacteria-mediated transfer (e.g., Agrobacterium T-DNA delivery system), electroporation, calcium phosphate co-precipitation, microinjection, lipofection, bombardment with nucleic-acid coated particles or other techniques, depending on the particular cell type. For grasses such as corn and sorghum, microprojectile bombardment as described, for example, in Sanford, J. C., et al., U.S. Pat. No. 5,100,792 (1992) can be used. Other useful protocols for the transformation of plant cells are provided in Gelvin et al., 1992. Suitable protocols for transforming and transfecting cells are also found in Sambrook et al., 1989. The nucleic acid constructs of this invention can also be incorporated into specific plant parts such as those described infra through the transformation and transfection techniques described herein.

To aid in identification of transformed plant cells, the constructs of this invention are further manipulated to include genes coding for plant selectable markers. Useful selectable markers include enzymes which provide for resistance to an antibiotic such as gentamycin, hygromycin, kanamycin, or the like. In the constructs of FIGS. 12A–12D, the NOS/NPTII kanamycin-resistant gene is used to detect transfected plant cells. Similarly, enzymes providing for production of a compound identifiable by colour change such as GUS (β-glucuronidase), or by luminescence, such as luciferase, are useful.

The invention provides transformant cells in which the introduced DNA has integrated into the genome, and transformant cells in which the introduced DNA exists as an extrachromosomal element. In the latter case, maintenance of an extrachromosomal element can be easily obtained by including a selectable marker in the recombinant expression vector and then, after introduction of the vector, growing the cells under conditions where expression of the marker gene is required. In one embodiment of this invention, cells transformed with a recombinant expression vector of the invention are screened using protein kinase activity as a selectable marker. Such transformed cells can be screened, for example, under conditions of phosphate starvation.

Plants and other photosynthetic organisms containing the nucleic acid constructs described herein are provided by this invention. The term "photosynthetic organism" is meant to include the members of the kingdom Planta, including vascular and nonvascular plants (angiosperms, gymnosperms, ferns, mosses, bryophytes, etc.), the algae, photosynthetic protists (single-celled eukaryotes), the Cyanophyta (blue-green algae or cyanobacteria) and the photosynthetic bacteria. Suitable plants include both monocotyledons and dicotyledons. Examples of preferred monocotyledons are commercially-important crop plants such as rice, corn, wheat, rye, sugarcane and sorghum. Examples of preferred dicotyledons are canola, sunflower, tomato, broccoli, and lettuce. Algae can be used as a hosts for the constructs described herein. Examples of such algae are *Chlamydomonas reinhardtii, Chlamydomonas moewusii, Euglena gracilis, Porphyra purpurea,* Cryptomonas sp., and *Ochromonas sinensis.* Prokaryotes can also provide suitable host cells. Specific examples include *Anacystis nidulans,* Synechococcus sp., *Rhodobacter sphaeroides, Rhodobacter capsulatus, Chloroflexus aurantiacus,* and *Heliobacterium chlorum.*

The constructs of the present invention can be introduced into plants, plant parts, or other cells of photosynthetic organisms using Ti plasmids, Ri plasmids, plant virus vectors, direct DNA transformation, micro-injection, electroporation, etc. For reviews of such techniques see, for example, Weissbach and Weissbach, (1988) and Grierson and Corey, *Plant Molecular Biology,* 2d Ed., Blackie, London, Ch. 7–9 (1988).

The method of obtaining transformed cells and/or regenerated plants is not critical to this invention. In general, transformed plant cells are cultured in an appropriate medium, which can contain selective agents such as antibiotics, where selectable markers are used to facilitate identification of transformed plant cells. Selected transformed plant cells can be induced to form callus tissue. Once callus forms, shoot formation can be encouraged by employing the appropriate plant hormones in accordance with known methods and the shoots transferred to rooting medium for regeneration of plants.

The transformants or descendants of transgenic plants so produced can be evaluated with respect to growth and productivity. Transgenic plants can also be assessed for flowering characteristics, root and shoot size ratios, and seed phytate, starch and oil content. The transformants would be used directly or could be subjected to further modifications by genetic engineering or classical techniques.

Transgenic plants containing the constructs of this invention can also be regenerated from plant tissues, plant parts, or protoplasts by methods known to those of skill in the art. Plant part is meant to include any portion of a plant capable of producing a regenerated plant. Thus, this invention encompasses cells, tissue (especially meristematic and/or embryonic tissue), protoplasts, epicotyls, hypocotyls, cotyledons, cotyledonary nodes, pollen, ovules, stems, roots, leaves, and the like. Plants can also be regenerated from explants. Methods will vary according to the plant species.

Seed can be obtained from the regenerated plant or from a cross between the regenerated plant and a suitable plant of the same species. Alternatively, the plant can be vegetatively propagated by culturing plant parts under conditions suitable for the regeneration of such plant parts. The plants can then be used to establish repetitive generations containing an altered genotype with respect to phosphate-inducible protein kinase activity, either from seeds or using vegetative propagation techniques.

Homology-dependent gene silencing including antisense nucleic acids

The invention further encompasses homology-dependent gene silencing including silencing for the nucleic acid of the invention mediated by DNA—DNA pairing and by RNA. In the former, DNA interaction between an introduced nucleic acid or oligonucleotide and the native homologue(s) result in co-suppression of the genes. RNA-mediated silencing includes antisense technologies in which a nucleic acid or oligonucleotide that is antisense to a nucleic acid of the invention is introduced into cells. Such an antisense molecule is capable of base-pairing (hydrogen bonding) with the nucleic acid of the invention in an anti-parallel manner, according to the standard pair rules, i.e., G pairs with C, and A pairs with T or U. The antisense molecule can be complementary to a coding or non-coding region of a nucleic acid of the invention, including a non-coding regulatory region, or to portions of both (Gogarten et al., 1992; Shotkoski and Fallon, 1994). The region of complementarity can precede or span the first codon of SEQ ID NO:1. An antisense molecule according to the invention can include a region complementary to a regulatory sequence, for example a non-coding regulatory sequence that is operatively linked to a gene of the invention in an expression construct. Alternatively, catalytic antisense RNA directed at the protein kinase gene transcript (a ribozyme) can be employed to reduce gene expression (Heinrich et al., 1993; de Feyter et al., 1996). The antisense molecule can be produced by chemical synthesis, PCR or an expression vector, using certain of the techniques discussed in the previous section, or by other standard techniques. (Meyer, P. and Saedler, H., 1996).

Antisense constructs include, but may not be limited to, the following:

1. A whole psr gene placed in reverse orientation in respect to a promoter;
2. An antisense sequence complementary to the unique 3' region (nucleotides 930 through 1272) of FIG. 7;
3. The first one-third of the antisense sequence described in (2) above (nucleotides 930 through 1080) which includes the partially conserved nucleic acid sequence encoding the EEEXXD sequence;
4. The second one-third of the antisense sequence described in (2) above (from nucleotide 1073) which includes the codon for the conserved "D" residue at position 336 of the amino acid sequence of FIG. 8;
5. An antisense sequence complementary to the 3'-untranslated region up to the polyA tail (nucleotides 1008–1240); or
6. An antisense sequence complementary to the 5'-untranslated region (nucleotides 10 through 88).

If cell death occurs with an antisense construct under the control of a seed specific or constitutive promoter, an inducible promoter could be used. Sense or antisense nucleic acid according to the invention can be delivered to cells using any of a variety of methods known to persons skilled in the art.

Isolated Proteins

This invention provides an isolated protein having protein kinase, β-glucosidase, or other psr protein activity and, in particular, an amino acid sequence with substantial sequence homology with the amino acid sequence shown as SEQ ID NO:2, SEQ ID NO:4, SEQ ID NO:6, SEQ ID NO:8, or SEQ ID NO:10. Alternatively, an isolated protein of the invention can be encoded by a nucleic acid that hybridizes under low or high stringency conditions to the nucleotide sequence of SEQ ID NO:1, SEQ ID NO:3, SEQ ID NO:5, SEQ ID NO:7, SEQ ID NO:9, or a protein encoded by any psr gene. It should be understood that the invention includes protein fragments demonstrating such homology and having psr protein activity (i.e., functional portions).

Figure 9:
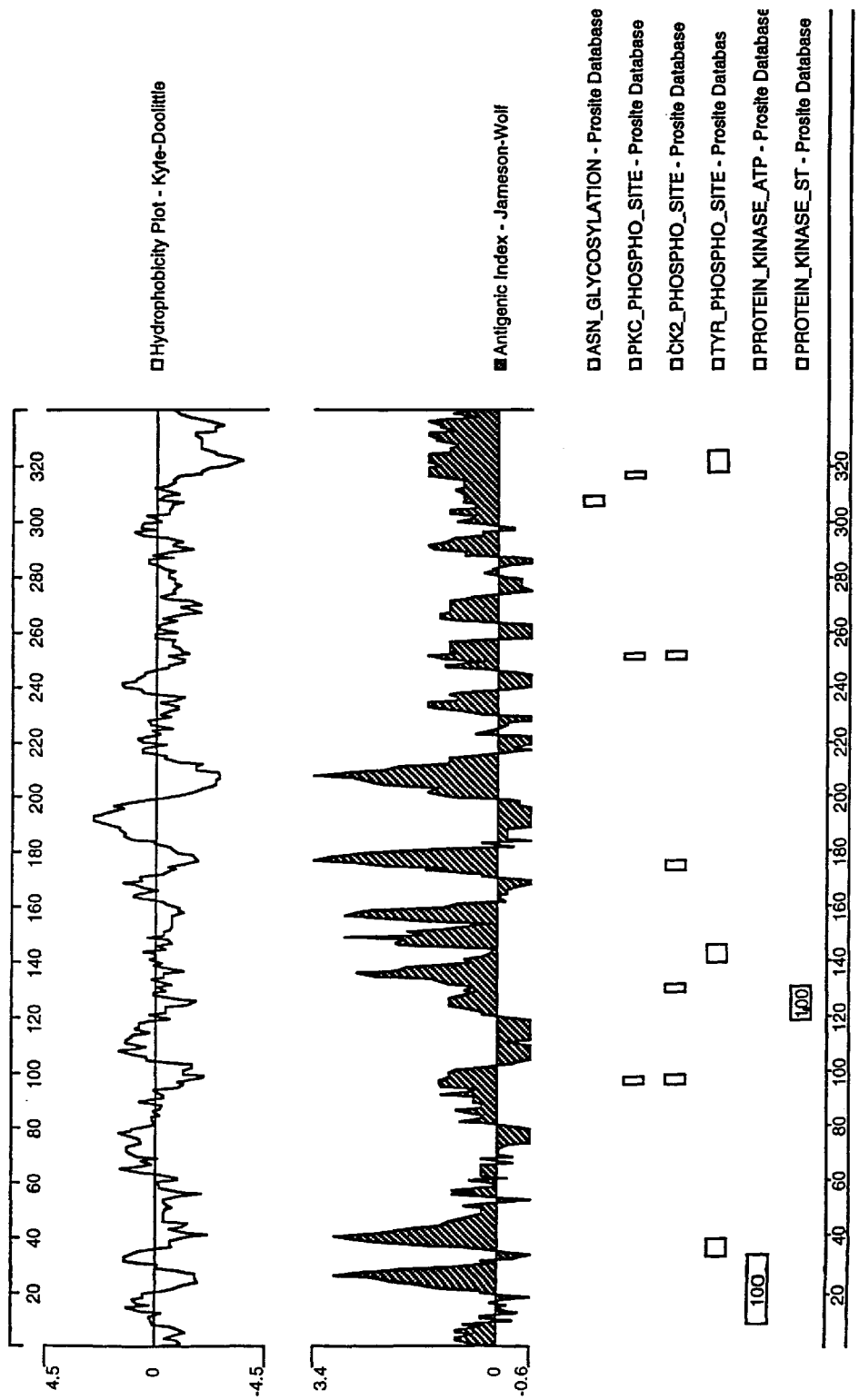
FIG. 9 shows a computer analysis of Arabidopsis thaliana psrPK protein deduced amino acid sequence.

The mature, unmodified protein having the amino acid sequence shown as SEQ ID NO:2 is predicted to have a molecular weight of 39,040 kDa. Prosite searches were used to determine the following characteristics of the PSRPK protein. It contains ser/thr protein kinase active site between amino acid positions 119–131, and an ATP-binding site between positions 9–33. An hydrophobicity plot of the protein does not indicate any long regions of membrane associated protein and antigenicity plot of the protein indicates several areas that would be appropriate for employment as peptides for antibody production against the protein. These include but are not restricted to the last 150 amino acids at the C-terminus. As there are no apparent N-terminal signal peptides or organellar targeting sequences, the protein appears to be cytoplasmically localized. There are a number of potential phosphorylation sites which include, but may not be restricted to, positions that are indicated by motifs for PKC, CK2, and tyrosine kinase phosphorylation sites as shown in FIG. 9. These may or may not be autophosphorylation sites. There is a putative glycosylation site in the C-terminal region.

A psr protein of the invention can be purified from cells or from culture medium into which it has been secreted. Alternatively, it can be chemically synthesized, as is well-known in the art. As discussed above, for the purposes of this disclosure, the term "isolated" means that the protein is substantially free of other cellular material or culture medium when produced by recombinant DNA techniques, or chemical precursors or other chemicals when produced by chemical synthesis.

The invention further provides a method of preparing a protein having protein kinase activity, β-glucosidase activity, or other psr protein activity, or a fragment of such a protein, which includes the following steps: (i) transforming cells with a recombinant expression vector including a nucleic acid of the invention and a regulatory sequence operatively linked to the nucleic acid, (ii) culturing the transformant cells in a suitable medium until the psr protein is formed, and (iii) isolating the psr protein. A person skilled in the art would be able to devise a scheme for the isolation of the protein from other cellular material and culture medium using conventional techniques (Scopes, 1982). These include chromatographic methods such as gel filtration, ion-exchange chromatography and affinity chromatography, as well as batch methods employing ion-exchange or affinity resins. Precipitation with ammonium sulfate, followed by resuspension and dialysis is another common purification and concentration protocol.

In another embodiment of the invention, a fusion protein comprising at least a functional portion of the psr protein of the invention can be prepared by the method whose steps are detailed above. In some embodiments, the psr protein or functional portion thereof can be fused to a signal sequence which directs secretion of the fusion protein from the transformant cells. The secreted protein can be isolated using standard techniques.

Antibodies

The invention encompasses an antibody that is specific for a psr protein of this invention. The invention includes both polyclonal and monoclonal antibodies. For purposes of this disclosure, the term "antibody" includes antibody fragments that are specific for a psr protein, such as a protein kinase or β-glucosidase, described herein. Such fragments include $F_{ab}$ fragments generated by proteolysis of an antibody. In some embodiments, an antibody can be directed to an epitope unique to the psr protein of the invention. If the protein is a protein kinase of this invention, for example, these can include the protein kinase active site and the ATP-binding site as well as the unique C-terminus sequence of 41 amino acids.

Intact psr proteins or an immunogenic fragment thereof can be used to prepare antibodies. The protein or fragment chosen as the antigen can be injected into an animal (e.g., rabbit, hamster, goat, mouse), causing the animal to produce antibodies specific to the injected antigen. The antigen is often combined with an adjuvant, such as Freund's adjuvant.

In some cases, prior to injection, the antigen is conjugated to a hapten, or carrier molecule. A person skilled in the art would be aware of appropriate antigen dosages for the size and species of animal, how to design a schedule of repeated injections if required, and how to titer and purify the antibody raised in the animal's serum. Methods of preparing antibodies including these and other aspects are described in Harlow and Lane, 1988.

For the production of monoclonal antibodies, lymphocytes raised against the antigen are first harvested, and then fused with myeloma cells using standard procedures (Harlow and Lane, 1988). The immortalized hybridoma cells so produced are screened for protein kinase-specific antibodies using conventional immunoassay methods such as ELISA (enzyme-linked immunosorbent assay). The antibodies can then be purified as is known in the art.

An antibody of the invention can be physically coupled to any of a number of detectable substances that are known in the art. These include: a radioisotope, a fluorescent molecule, and an enzyme capable of catalyzing a calorimetric reaction. Examples of such an enzyme include alkaline phosphatase and horseradish peroxidase, which are commonly used in laboratory assays.

Thus, this invention provides a method of detecting the expression of a phosphate-starvation inducible protein, such as a protein kinase or a β-glucosidase, in a plant or plant part or other photosynthetic organism comprising: (a) inducing the protein expression by depriving the plant, plant part, or other photosynthetic organism of sufficient levels of available phosphorus; (b) contacting a portion of a plant, plant part, or other photosynthetic organism with antibody to the protein so that an antibody:antigen complex is formed by the binding of the antibody to an epitope of the protein; and (c) detecting the antibody:antigen complex; wherein the detection of the antibody:antigen complex is indicative of the expression of the protein.

Transgenic Plants and Photosynthetic Organisms

The classical approach to optimizing plant characteristics utilizes traditional plant breeding methods 30 wherein plants with desirable traits are crossed to produce new, true-breeding cultivars carrying the traits. This approach has at least two serious drawbacks. First, traditional plant breeding relies on the availability of desired traits within known cultivars. The desired phosphate-related traits discussed supra are either not part of the genome of certain species or varieties or cannot be acquired to the required level of expression in plants wherein they occur. Second, traditional breeding is a relatively slow process.

A more modern approach to modifying the characteristics of plants (and other photosynthetic organisms) is to subject plants to mutagenesis by radiation or chemical treatment. Such exposure randomly generates mutations in the DNA molecules comprising the plant genome which sometimes produces the desired traits. The mutagenized plants are screened for the traits and subsequently bred. While mutagenesis has the advantage of producing variations in plant DNA much faster than natural selection, it is not possible to select and generate preferred traits; the process is random. Further, exposing plants to mutagenic agents can induce additional, undesirable mutations to the plant genome. Some of these may not be immediately apparent and, further, may not be able to be "bred out" of a plant carrying a useful mutation.

The nucleic acids and vectors of the invention can also be used to produce transgenic plants and other photosynthetic organisms which express the protein of the invention. The genome of a transgenic organism includes an integrated DNA transgene that was introduced either into that particular organism or into its ancestor. The introduced DNA including the transgene can comprise regulatory element(s) appropriate for the type of organism or tissue being transfected. For example, when introduced as a transgene, a nucleic acid of the invention can be operatively linked to a tissue-specific DNA regulatory sequence such that protein kinase is specifically produced in the target tissue. A seed-specific promoter would permit expression of the protein kinase only in seeds. Also, a suitable 3' region such as the 3' region containing a polyadenylation signal of Agrobacterium tumor inducing (Ti) plasmid genes can be included. Or other suitable 3' sequences derived from any characterized gene from plants as well as from other organisms such as animals, if they are deemed appropriately functional in the environment of a transgenic plant cell, can be used. To aid in identification of transformed plant cells, the constructs of this invention can be further manipulated to include genes coding for plant selectable markers.

Thus, genetic engineering provides a method of producing a transgenic plant or other photosyntheic organism having altered growth, reproduction, or metabolic content by introducing into a cell or tissue of a plant or other photosynthetic organism, an exogenous nucleic acid which encodes a β-glucosidase which is transcribed under conditions of phosphate deprivation in naturally-occurring species in which it occurs, and whose presence in the transgenic plant or photosynthetic organism results in altered growth, reproduction, or metabolic content, and by maintaining the cell or tissue containing the exogenous nucleic acid under conditions appropriate for growth of the cell or tissue, whereby a transgenic plant or other photosynthetic organism having an altered growth, reproduction, or metabolic content can be produced. More specifically, the nucleic acids comprising the psrPK, psr3.2, psr3. 1A, psr3. 1B genes and homologues can be used in this method to produce a transgenic plant from a species which belongs to the vascular plants including angiosperms, gymnosperms, monocots, and dicotsand the algae are plants, and the algae. Thus plants and other photosynthetic organisms are provided wherein the naturally-occurring phosphate-starvation induced protein kinase or β-glucosidase activity is reduced. Because the introduced gene is stably integrated into the genome, seed of a transgenic plant and, therefore future generations of descendants, with this alteration, are also provided by this invention.

Applications and Utilities

Photosynthetic organisms have evolved a number of adaptive strategies to cope with growth-limiting amounts of exogenous inorganic phosphate. These strategies include enhancing the availability of endogenous phosphate (Lefebvre et al., 1990; Sachay et al., 1991), and using it efficiently in order to maintain essential metabolic pathways (Duff et al., 1994), as well as, in times of plenty, storing excess phosphate in vacuoles (Lee et al., 1990; Mimura et al., 1990; Tu et al., 1990) so that it can later be used to replenish the cytoplasmic pool as required (Rebeille et al., 1983). Also, root systems secrete acids and phosphatases that increase phosphate availability by releasing $P_i$ from rock phosphate and phosphate esters, respectively (Lefebvre et al., 1990; Sachay et al., 1991). The mechanisms of these relief strategies involve changes in either protein synthesis and degradation (Duff et al., 1991), or secretion of pre-existing proteins, including phosphatases (Goldstein, 1992). They invoke changes in phosphate-dependent reactions of photosynthesis (Rao et al., 1990; Usuda and Shimogawara, 1993), respiration (Duff et al., 1989b; Duff et al., 1994;

Hoefnagel et al., 1993; Nagano and Ashihara, 1993; Rychter and Mikulska, 1990; Theodorou and Plaxton, 1993), nucleotide synthesis (Ashihara et al., 1988; Rychter et al., 1992), protein synthesis (Sadka et al.,1994) and synthesis of cell wall and other metabolites (Fife et al., 1990).

The physiological consequences of $P_i$ limitation in the *Brassica nigra* (*B. nigra*) cell culture system have been studied extensively. These include the accumulation of lipids, starch and phenolic compounds (Fife et al., 1990), an elevated potential for $P_i$ absorption (Lefebvre et al., 1990) and the apparent deployment of alternative enzymes that act to "bypass" $P_i$- or nucleotide-dependent reactions (Duff et al., 1989b; Duff et al., 1994; Theodorou and Plaxton, 1993).

Recently, in an effort to define components of the regulation of homeostasis of $P_i$ concentration in plant cells, a mutant of *Arabidopsis thaliana*, pho2, was isolated that accumulates excess $P_i$ in the shoot (Delhaize and Randall, 1995). The authors suggested that this mutation could affect the regulation of $P_i$ transport across cell membranes. Another mutant, pho1, of this species identified previously is defective in loading of $P_i$ into xylem (Poirier et al., 1991).

It has been proposed that ribonucleases and phosphatases act in tandem to cleave and dephosphorylate RNA molecules in a $P_i$ recycling process (Goldstein, 1992). One extracellular (Glund and Goldstein, 1993; Nurnberger et al., 1990) and four intracellular ribonucleases were reported to be induced in $P_i$-starved tomato (Loffler et al., 1992). The activities of phosphatase enzymes are known to increase in plants experiencing $P_i$ deficiency (Duff et al., 1989a; Duff et al., 1991; Duff et al., 1994; Goldstein et al., 1989) and it has been shown that acid phosphatases are synthesized de novo in $P_i$-starved cell cultures of *B. nigra* (Duff et al., 1989b). The synthesis of the a-subunit of $PP_i$-dependent phosphofructokinase is also induced in *B. nigra* cells under $P_i$ stress (Theodorou et al., 1992). Recently, high concentrations of $P_i$ have been shown to down-regulate a sucrose-inducible phosphatase gene (vspB) in soybean (Sadka et al., 1994).

A $P_i$-starvation inducible β-glucosidase could be involved in the deglycosylation and, hence regulation of, certain enzymes during $P_i$ stress (Balou and Fisher, 1986; Gellatly et al., 1994).

The nucleic acids, constructs, and methods of this invention can be applied to regulate aspects of the phosphate-starvation response of photosynthetic organisms, as well as phosphate metabolism of such organisms in general. By altering the activity of a psr protein, i.e., changing the level of expression or modifying its activity, a change in regulation of the phosphate metabolism pathways can be effected. Thus, phosphate metabolism efficiency could be improved, allowing growth of organisms in phosphate-poor soils without addition of phosphate fertilizers, or improved growth even in phosphate-sufficient environments. Reducing the amount of phosphate fertilizer required for crop plants and/or improvement in yields, would have significant and desirable economic and environmental ramifications.

Also, the timing of certain plant phenomena that depend on phosphate metabolism can be altered. For example, the temporal and quantitative aspects of flowering can be modified in photosynthetic organisms in which reproductive evocation is responsive to the ratio of nitrogen to phosphorus in their environments. Earlier flowering would shorten the growing season for crops and reduce the seed to flowering time for bedding plants. Conversely, delay in flowering is desirable in crops harvested for their biomass, such as lettuce and spinach.

Alteration of phosphate metabolism of plants can also result in an altered biomass ratio between root and shoot, and be used to produce a commercial benefit in root crops, such as carrots. Additionally, the ability to induce larger root systems on plants early in the growing season would contribute to drought tolerance later during drier months.

Further, photosynthetic organisms can be modified to increase the nutritive value of vegetative or reproductive organs. For example, seed plants such as canola, soybean and corn, store phosphate in the form of phytate (the salt of 1, 2, 3, 4, 5, 6-cyclohexanehexolphosphoric acid). The presence of phytate is a problem where the seed is made into meal and used as feed for animals. Monogastric animals cannot metabolize phytate and utilize its phosphate. In addition, phytate binds to essential minerals, such as calcium, manganese and zinc, making them relatively unavailable to the animal. Alteration of phosphate metabolic pathways in plants could be altered to reduce the level of phytate in seeds in favour of a phosphate storage form that is more usable for animals and humans.

The advantages of the compounds and methods of this invention are multifold and those of skill in the art will recognize that the examples given above are just a few of the applications provided by this invention.

Increased Expression of Protein Kinase

The following examples indicate what can occur if psrPK is over expressed or modified to increase its activity. Part of this invention is also to implement the opposite strategy in which this gene or its homologues are underexpressed or modified to decrease activity. Those of skill in the art will recognize that similar techniques can be used to alter the expression of other psr proteins.

General constitutive promoters can be employed to increase expression of psrPK and similar genes throughout the transformed organism to increase its ability to utilize phosphate, thereby growing better under conditions of phosphate limitation and imparting the ability of the plant or other organism to grow better under any regime of phosphate nutrition.

Tissue-specific expression in the roots can have the effect of increasing root size as well as increasing the root's ability to acquire phosphate from the environment and to use it more efficiently in their root metabolism.

Shoot-specific expression is anticipated to alter the temporal aspects and magnitude of flowering, as well as increasing the efficiency phosphate utilization in the shoot.

Seed-specific expression can alter the efficiency of phosphate utilization in the seed thereby causing more seeds to set and larger seeds to be formed. This strategy can also reduce phytate storage pools in the seed. This can also increase the starch and oil storage capacity of the seed. Phosphate-deprived *B. nigra* suspension cells store more fixed carbon than phosphate-sufficient cells (Lefebvre et al. 1990).

Other tissue-specific expression can include root hairs for increased phosphate uptake, and other tissues where excessive or inadequate expression can be deleterious to cells and can cause cell death. This can be employed in the production of male sterile lines for hybridization purposes, among other applications.

Methods of Reducing Protein Kinase Expression

The invention encompasses methods of reducing expression of a nucleic acid or a protein of the invention. For example, a transgenic organism can be produced which expresses a molecule that binds directly to an endogenous psrPK protein and reduces its protein kinase activity or its ability to bind a substrate or cofactor. Further, expression of a molecule which binds to a cis-acting regulatory element or a trans-acting regulatory factor so as to interfere with their function can decrease protein kinase expression.

A third method can employ the modification of a nucleic acid or a protein such that it is dysfunctional and interferes with the native (naturally-occurring) functional protein in any way so that its protein kinase activity is reduced or eliminated.

A fourth method can employ an antisense molecule as described in section II above. The inventors contemplate that, when an antisense molecule of the invention is delivered to target plant cells, it will hydrogen bond with endogenous nucleic acid molecules encoding the protein kinase, thereby reducing gene expression of the protein kinase. The antisense molecule can be designed such that its region of complementarity with an endogenous protein kinase-encoding nucleic acid molecule includes the initiation codon of the sense strand. The antisense molecule can include regions complementary to coding or noncoding regions of the sense strand, or both.

A fifth method can employ transformation such that the introduced nucleic acid comprising part or all of the nucleic acid of the invention in the sense orientation reduces protein kinases expression by any means including gene co-suppression (Meyer and Saedler, 1996).

Although this invention is described in detail with reference to preferred embodiments thereof, these embodiments are offered to illustrate but not to limit the invention. It is possible to make other embodiments that employ the principles of the invention and that fall within its spirit and scope as defined by the claims appended hereto.

All references cited herein are hereby incorporated by reference.

EXAMPLES

Example 1
Plant Cell Culture

Non-photosynthetic, rapidly growing *Brassica nigra* cell suspensions were cultured as described (Lefebvre et al., 1990) in MS medium (Murashige and Skoog, 1962) containing 6% sucrose (17.5 mM), and 2 mg/l 2,4-dichlorophenoxyacetic acid (2,4-D) at 24° C. with 130 r.p.m. rotary shaking. To assure the same nutritional state for all cultured cells, 6 ml of 7-day old cultures containing 3 ml of cells (packed cell volume) were inoculated into 44 ml of fresh MS medium containing 1.25 mM $P_i$. Packed cell volume was determined by allowing the cells to settle from the culture medium in sterile graduated cylinders for 45 min. After 7 days of culture, the same quantity of cells was subcultured into 44 ml of fresh MS medium containing either 10 mM, 1.25 mM, or no phosphate and incubated for an additional 7 days. For the 10 mM $P_i$ treatments, filter-sterilized $KH_2PO_4$ adjusted to pH 5.8 with KOH was added to the 1.25 mM $P_i$ medium. In the minus $P_i$ treatments, an equal molarity of KCl replaced the $KH_2PO_4$.

The patterns of growth and endogenous phosphate concentrations of these cultured cells are shown in FIG. 1. Cells fed with 10 mM $P_i$ had ample supplies of this nutrient for the duration of the culture period. Cells fed with 1.25 mM $P_i$, in comparison to minus $P_i$-treated cells, underwent only mild $P_i$ deprivation by relying on conversion of their own internal phosphate. Quantitative determination of endogenous phosphate was performed as previously described (Lefebvre et al., 1990).

After 7 days growth, the cultured cells were collected on fritted glass filters with 10 μm pore size, and rinsed with 100 ml of 0.5 mM $CaCl_2$ before freezing in liquid nitrogen and storage at −70° C. until required.

Example 2
Extraction of Total RNA and mRNA

Total RNA from the harvested *B. nigra* cells of Example 1 was isolated as described by Chirgwin (Chirgwin et al., 1979). The cells were homogenized at ice-cold temperature using a homogenization buffer containing 4 M guanidinium isothiocyanate (GIBCO/BRL, Burlington, Canada). Poly (A)+ RNA (mRNA) was purified by using the mRNA purification kit and recommended protocol of Pharmacia (Uppsala, Sweden and Piscataway, N.J.). Total RNA and mRNA isolated from minus $P_i$-treated, 1.25 mM $P_i$-fed and 10 mM $P_i$-fed cells were quantified spectrophotometrically and examined on formaldehyde/agarose gels (Sambrook et al., 1989).

Example 3
Analysis of Changes in the Populations of mRNA Species Using in Vitro Translation It is well known that the protein synthesis profiles of $P_i$-starved and $P_i$-fed *B. nigra* cells differ. Such differences in response to $P_i$ starvation could be mediated in various ways. To investigate whether any alterations in protein levels are due to changes at the transcriptional level, in vitro translations of mRNA extracted from $P_i$-starved and $P_i$-fed *B. nigra* cells were compared. In vitro translation of mRNA purified as above was carried out according to the protocol of Promega (Madison, Wis.), using wheat germ extract (Promega) and [$^{35}$S]-methionine (ICN, Costa Mesa, Calif.) diluted with unlabeled methionine to a final concentration of 0.5 mCi/ml.

After translation, a 5 μl aliquot was removed from each reaction mixture and combined with 20 μl of gel-loading buffer to a final concentration of 1% SDS (Laemmli, 1970). The samples were placed in a boiling water bath for 5 min and then subjected to denaturing SDS-polyacrylamide gel electrophoresis (SDS-PAGE) using an LKB 2010 Macrophor electrophoresis apparatus (Pharmacia Biotech, Inc., Baie d'Urfé, Canada) and the discontinuous system of Laemmli (Laemmli, 1970). Molecular weight standards electrophoresed in parallel were $^{14}$C-labeled α-lactalbumin, carbonic anhydrase, glyceraldehde-3-phosphate dehydrogenase, chicken egg albumin and bovine serum albumin having molecular weights of 14, 29, 36, 45 and 66 kDa, respectively (Sigma, St. Louis, Mo.). The gels were 0.4 mm thick slabs containing 1% SDS. The acrylamide monomer concentrations were 5% (w/v) for the stacking gel and 10% for the separating gel. The separating gel was 35 cm long, to maximize resolution of protein species. Electrophoresis was performed at 25° C. for 5 h at a constant current of 30 mA.

Upon completion of electrophoresis, the gel, bound to a bind-silane-treated (Pharmacia) glass plate, was incubated in 600 ml of fixing solution containing 20% trichloroacetic acid (TCA) and 10% methanol for 20 The gel was then washed three times in 600 ml of post-fixing wash solution containing 10% ethanol and 5% acetic acid, and dried to the glass plate overnight in a fume hood at room temperature. The dried gel was exposed to X-ray film using a Cronex intensifying screen (DuPont, Wilmington, Del.) at −70° C. and the film was developed using Kodak developer and fixer solutions. The autoradiogram was inspected visually, and scanned using an LKB enhanced UltraScan XL Laser Densitometer (Pharmacia). The densitometric scan was analyzed with GelScan XL Software, Version 2 (Pharmacia).

Results of such analysis are presented in FIG. 2. It was assumed for convenience that the density of each band was proportional to the amount of that polypeptide synthesized in vitro and, therefore, also proportional to the amount of 4 mRNA coding for the polypeptide. Differences in the densities of corresponding bands between different $P_i$ treatments were thus taken to represent differences in the abundance of the mRNA species that produced that band. One should nonetheless keep in mind that, since the proteins were labeled with $^{35}S$-methionine, the signal is proportional to the methionine content of each polypeptide; to compensate somewhat for this factor, only signals of the same molecular weight were compared between treatments.

The majority of [$^{35}S$]-methionine-labeled translation products were detected in all $P_i$ treatments. Sixteen polypeptides, however, varied in their signal intensities among the three treatments. FIG. 3 is a summary of the standardized data of the expression differences between polypeptides produced from 10 mM $P_i$-fed, 1.25 mM $P_i$-fed and $P_i$-deprived cells. Based on these analyses, $P_i$ deprivation caused the copy number of mRNAs to increase for ten polypeptides, whereas six others decreased. Of translatable mRNAs showing altered expression, four species corresponding to proteins with estimated molecular weights of 31.7, 32.3, 52.5, and 64.8 kDa were only detected in the $P_i$-starved treatment. By comparison with the other polypeptides, these were expressed at relatively high levels during $P_i$ deprivation. The repression of a 43.5 kDa polypeptide was also noted in minus $P_i$-treated cells. The other six polypeptides representing mRNAs preferentially expressed during $P_i$ starvation had estimated molecular weights of 19.6, 40.6, 30.1, 37.0, 18.6, and 29.5 kDa. These were expressed at approximately 3.3, 2.8, 2.7, 1.7, 1.3, and 1.2 times higher levels, respectively, in the minus $P_i$-treated cells than in the 10 mM $P_i$-fed cells. In addition, there were 20-, 6.6-, 1.8-, 1.6-, and 1.4-fold decreases in the minus $P_i$-treated cells in the expression of polypeptides with estimated molecular weights of 14.4, 35.9, 48.3, 18.4, and 35.5 kDa, respectively. In the 1.25 mM $P_i$-fed cells, the mRNAs coding for the sixteen differentially expressed polypeptides appeared to be present either at intermediate levels or at levels similar to those in the minus $P_i$-treated cells.

No difference was detected between the patterns of gel electrophoresis of the in vitro translation products when using either total RNA or poly(A)$^+$RNA. The above results were consistent in three independent experiments.

Example 4

Construction of cDNA Library from Minus $P_i$-Treated Brassica nigra Cells

Approximately 10 µg of poly(A)$^+$RNA purified from cells deprived of $P_i$ for 7 days was used to synthesize a double-stranded CDNA library using the c-CLONE II CDNA Synthesis kit (Clontech, Palo Alto, Calif.) according to manufacturer's instructions. The oligo-d(T)-tailed cDNA products produced were fractionated on a Chroma Spin-400 column (Bio/Can Scientific, Mississauga, Canada) to obtain cDNA molecules greater than 400 bp in length. The size range of such molecules was estimated to be from about 0.5 kb to about 3 kb in length. Using EcoRI restriction site sticky ends, the size-selected cDNA molecules were ligated into EcoRI predigested/phosphatase-treated λZAPII bacteriophage arms as recommended by the manufacturer (Stratagene, La Jolla, Calif.). Recombinant phages were packaged with Stratagene's Gigapack II Gold and titered on a lawn of $E. coli$ XL1-Blue bacteria grown on LB agar plates according to the manufacturer's protocol. The ligation efficiency at an optimal ratio of cDNA: vector (44 ng: 500 ng) was $7.5 \times 10^6$ plaque forming units (pfu)/µg cDNA.

Example 5

Differential Hybridization and Cross-Hybridization Screening of the cDNA Library from Minus $P_i$-Treated Brassica nigra Cells The cDNA library from minus $P_i$-treated $B.$ nigra cells described above was differentially screened by hybridizing to cDNA probes from both minus $P_i$-treated and 10 mM $P_i$-fed $B.$ nigra cells, in order to identify genes responsible for the differences in protein and mRNA profiles between these cells.

Single-stranded cDNA probes were synthesized from mRNAs isolated from the $P_i$-deprived and 10 mM $P_i$-fed cells to make -P and +P probes, respectively. This was done as previously described (Sambrook et al., 1989), using a mixture of 5 µg of mRNAs and 7.4 µg of random hexadeoxyribonucleotides (Pharmacia). Incorporation of radiolabel was achieved by including α-$^{32}$P-dATP (ICN) in the reaction mixture. Reaction products were extracted with phenol:chloroform and purified on Sephacryl S-300 columns (Pharmacia).

The unamplified cDNA library was plated on a lawn of $E. coli$ strain XL1-Blue growing at low density (2,000 pfu per 90 mm LB plate). A total of about 50,000 plaques were screened as follows: First, duplicate lifts were prepared from each plate. The plaques' DNA was denatured and immobilized on nitrocellulose filters (Amersham, Oakville, ON, Canada) by standard methods (Sambrook et al., 1989). The filters were baked, prewashed in a solution of 5× SSC, 0.5% SDS, 1 mM EDTA (pH 8.0) for 1 h at 68° C. and prehybridized in a solution of 6× SSC, 0.05× BLOTTO, 25 µg/ml of denatured, fragmented salmon sperm DNA (Pharmacia) at 68° C. for 2–3 h. (1×BLOTTO contains 5% non-fat dried milk (Carnation Inc., Toronto) and 0.02% sodium azide (Sigma).) For each pair of duplicate filters, one was hybridized to the radiolabeled -P probes and the other to the radiolabeled +P probes at 68° C. overnight. The filters were then washed under conditions of increasing stringency as follows: three times in 2× SSC, 0.1% SDS at room temperature for 5 min.; twice in 1× SSC, 0.1% SDS at 68° C. for 1–1.5 h; and once in 0.2× SSC, 0.1% SDS at 68° C. for 1 h. (1× SSC solution consists of 0.15 M NaCl and 15 mM trisodium citrate.) Autoradiography was performed as described above. Clones that hybridized to -P probes but not to +P probes were identified as "positive". These clones were then subjected to second and third rounds of screening.

Three rounds of screening resulted in the isolation of 131 clones that were preferentially expressed in the starved cells. Because the total number of plaques screened was deliberately large (so as not to miss anything), the 131 clones included multiple separate cloning events of the same gene (s). Therefore, it was necessary to cross-hybridize the isolated clones to each other, in order to distinguish duplicate from novel cloning events.

The isolated clones were digested with EcoRI, PstI and TaqI restriction enzymes and the resulting DNA fragments were separated on 1i agarose gels and transferred to Nytran membranes (Schleicher & Schuell, Keene, NH) in 10× SSC overnight (Sambrook et al., 1989). $^{32}$P-labeled single-stranded probes were generated from the liberated $B.$ nigra inserts of individual clones using PCR (Konat et al., 1991), employing $T_3$ and $T_7$ primers in the first round and either $T_3$ or $T_7$ primers in the second round of reactions.

Membranes to which DNA from the isolated clones was bound were first baked for 30 min. at 80° C., then prehybridized for 5 min. at 65° C. in 0.25 M NaH$_2$PO$_4$ (pH 7.2), 7% SDS, 1 mM EDTA. Next, radiolabeled probe was added and hybridization was allowed to proceed for 2 hr. The membranes were then washed twice in 40 mM $NaH_2PO_4$ (pH 7.2), 5% SDS, 1 mM EDTA and twice in 40 mM $NaH_2PO_4$ (pH 7.2), 1% SDS, 1 mM EDTA, each time for 30–60 min. at 65° C. Autoradiography was as described above. The membranes were stripped of bound probe by washing twice in 0.1× SSC and 0.5% SDS at 95° C. for 20 min.

The results of the cross-hybridization analysis (not shown) permitted the majority of the $P_i$-inducible clones to be placed into eleven different homology groups, which were designated plant "$P_i$-starvation responsive" (psr) groups1 to 11. Because these genes are particularly active during periods where phosphate is unavailable, they are assumed to be involved in the plant response to phosphate starvation.

Example 6
RNA Analysis of psr cDNA Clones Using Northern Blots

Figure 4:
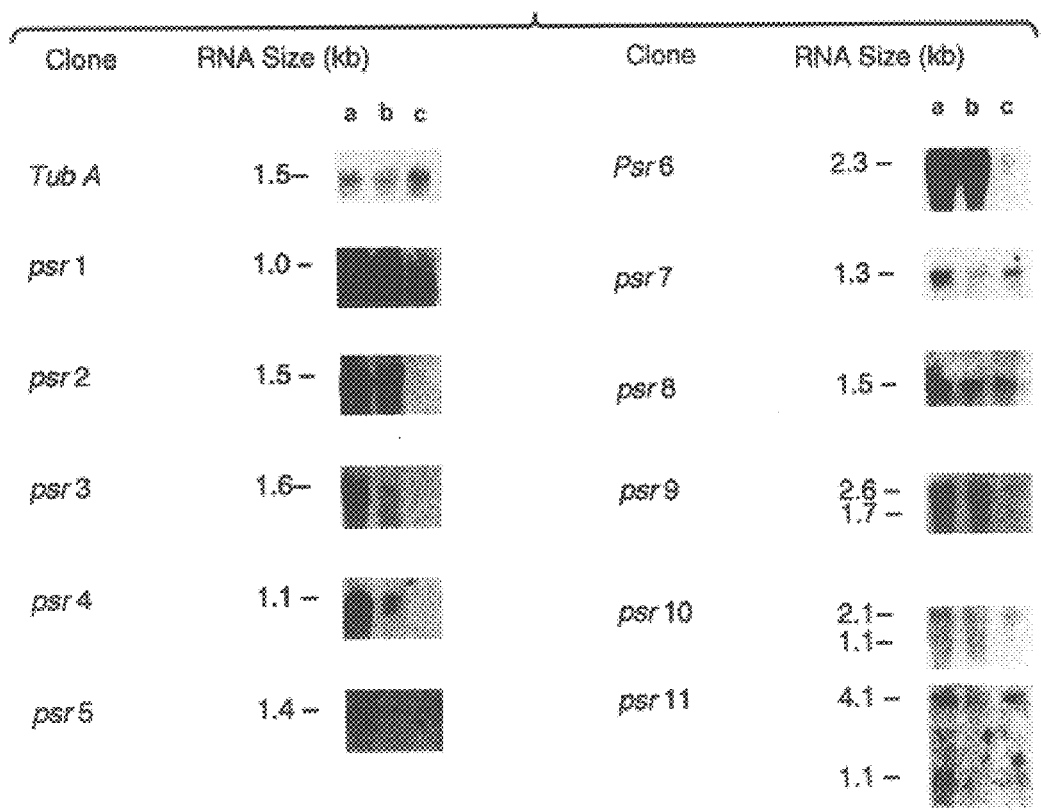
FIG. 4 shows northern blots of total RNA extracted from 7-day old (a) minus $P_i$-treated, (b) 1.25 mM $P_i$-fed, and (c) 10 mM $P_i$-fed B. nigra suspension cells. Tub A is the α-tubulin gene that was used as a standard. Values given to the left of each panel are size estimates of mRNA species corresponding to the respective psr clones. Each lane contained 30 μg total RNA.

The induction and relative abundance of psr mRNAs under the different phosphate growth conditions were further assessed by northern blotting, results of which are shown in FIG. 4.

Cloned psr cDNA inserts were liberated from vector DNA by digestion with EcoRI. The reaction products were electrophoresed on a 1% agarose gel and bands containing insert DNA were excised. This DNA was subsequently purified using GeneClean II (Bio 101 Inc., Vista, Calif.) and radiolabeled by random-priming reactions (Sambrook et al., 1989). The radiolabeled probes were purified using Chroma Spin-30 columns (Clontech, Palo Alto, Calif.). A control DNA probe (α-tubulin) was similarly radiolabeled and purified.

30μg of total RNA extracted from each of the minus $P_i$-treated, 1.25 mM $P_i$-fed and 10 mM $P_i$-fed cells were electrophoresed on a 2.2 M formaldehyde/ 1% agarose gel (Sambrook et al., 1989) and transferred to Nytran Plus membrane (Schleicher & Schuell) according to the manufacturer's protocol.

Individual blots were incubated at 42° C. for 30 min. in prehybridization buffer that contained 50% formamide, 0.12 M $NaH_2PO_4$ (pH 6.8), 0.25 M NaCl, 7% SDS, and 1 mM EDTA. They were transferred to 10 ml of fresh hybridization buffer containing 2–5×$10^7$ cpm of probe at approximately 4 ×$10^9$ cpm/ μg specific activity. Hybridization was overnight at 42° C. followed by washing for 30 min. each in 2× SSC, 0.1% SDS at room temperature; 0.5× SSC, 0.1% SDS at room temperature and 0.1× SSC, 0.1% SDS at 65° C. Autoradiography was for 1–4 days. To reuse the blots, bound probes were removed by washing in 0.1% SDS for 5 min, followed by equilibration in 5× SSC, 0.1% SDS at room temperature for 20 min. and stripping in the same solution for 2 min. at 95° C.

Based on comparisons to the α-tubulin internal standard, most of the psr genes were relatively highly expressed and all were induced in both the minus $P_i$-treated and the 1.25 mM $P_i$-fed cells, with somewhat less expression in the latter cells. In 10 mM $P_i$-fed cells, low levels of mRNA expression were observed for psr7, 8, 9, 10 and 11, whereas transcripts for the other genes were not detected. High stringency washing did not remove the additional bands seen in all $P_i$ treatments when probing with psr9, 10 and 11. For each of these, the differentially expressed mRNA species was the smallest size of those detected.

Example 7
Nuclear run-Off Experiments

Figure 10:
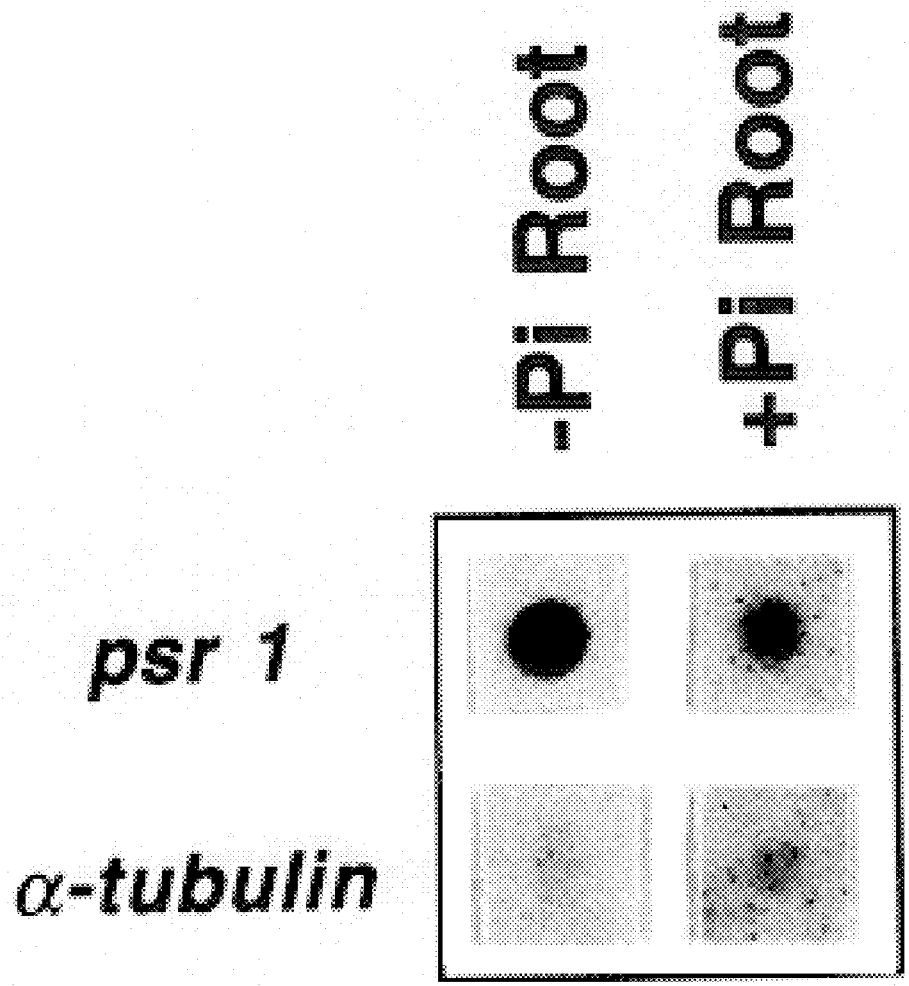
FIG. 10 shows the results of a nuclear runoff experiment.

Plasmid DNA carrying the *B. nigra* psr1 cDNA or *A. thaliana* α-tubulin inserts were alkaline denatured and applied to Nytran-Plus (Schleicher and Schuell, Guelph, Canada) using Bio-Dot Microfilteration apparatus (Bio-Rad) at five μg per dot. In order to produce probe from newly synthesizing mRNA species, transcriptionally active nuclei were isolated from 5–6 g of 5 mM $P_i$-fed and $P_i$-starved root tissues as described (Willimizer and Wagner, 1981). Transcription was allowed in the presence of 32P-UTP for 60 min at 30° C. using the method of Chappel and Hahlbrock (1984). Labelled RNA were purified as described by Somssich et al. (1989). Approximately $10^6$ cpm of RNA probe was used for hybridization with the dot blots as described (Malboobi and Lefebvre, 1995). After the last wash, the blot was treated with 20 μg/ml of ribonuclease A in 2× SSC for 30 min at room temperature. The blot was then washed with 2× SSC, 0.5% SDS, twice and 2× SSC, twice. Dot blots were exposed to X-ray film for 7 or more days. The results are shown in FIG. 10.

Example 8
Plant Culture

Arabidopsis thaliana (var. Columbia) seeds were surface sterilized for ten minutes in 30% bleach (Javex), 0.03% triton X-100 (Sigma) and washed with sterilized water six times. Seeds were transferred onto a 1 $cm^2$ piece of steel mesh placed on solid MS (Murashige and Skooge) plates containing 0.5% agar and 2% sucrose. After 11 days, plantlets grown and rooted through the mesh were transferred to 15 ml of half strength liquid MS medium containing 1.25 mM $P_i$ and 1% sucrose in 125 ml Erlenmeyer flasks at 24° C., 540 lux light with 80 r.p.m. rotary shaking. Three days later, plants were transferred into MS medium with various concentrations of nutrients as follows. For treatments with differing concentrations of $P_i$, filter-sterilized $KH_2PO_4$ adjusted to pH 5.8 with KOH was added to the 1.25 mM $P_i$ medium up to 5 mM. For the minus $P_i$ treatments, filter-sterilized KCl replaced the $KH_2PO_4$ to 5 mM concentration.

Example 9
DNA Sequencing and Computer Analysis

The psr cDNA inserts were excised in vivo from selected recombinant λZAPII phages into Bluescript™ plasmid vectors in the presence of R408 helper phage according to supplier's instructions (Stratagene). Plasmid DNA was prepared by CsCl gradient centrifugation (Sambrook et al., 1989).

Both strands of the isolated DNA was then sequenced using a Sequenase Version 2 Kit (United States Biochemical Corp., Cleveland, Ohio) with $T_3$ and $T_7$ primers, and other appropriate primers along the sequence (Stratagene). Sequencing of the 5' and 3' ends of these clones immediately indicated clear distinctions between the eleven psr groups.

Homology searches on the obtained sequences were performed with the BLASTX program (Gish et al., 1993) against the GenBank database through NCBI (The National Center for Biotechnology Information). Assembling and editing of the coding sequence and analysis of DNA and predicted protein sequences was performed using related programs of LASERGENE software for Macintosh (DNASTAR, Madison, Wis.).

Clone psr1 was identified as a gene coding for a phosphate-starvation inducible protein kinase. It has therefore been given the additional name psrPK. The psrPK sequence possesses high homology to protein kinases isolated from other plants, such as Glycine max protein kinase 2 (SPKZ, GB accession #L19360, 63% homology), *Arabidopsis thaliana* protein kinase 2 (ASK2, GB Accession # Z12120, 70% homology) (Park et al., 1993), *Brassica napus* serine threonine kinase 1 (BSK1, GB Accession #L12393, 69% homology), *Glycine max* protein kinase 3 (SPK3, GB Accession #L19361, 76% homology), *Brassica napus* serine threonine kinase Z (BSKZ GB Accession # L12394, 71% homology), *Arapidopsis thaliana* protein kinase 1 (ASK1, GB Accession # P43291, 71% homology) (Park et al., 1993).

An *A. thaliana* λPRL2 cDNA library (CD4-7) was obtained from the Ohio State Arabidopsis Biological Resource Center.

It was screened at high stringency with a probe consisting of the entire *B. nigra* psrPK cDNA insert. The *B. nigra* psrPK cDNA insert was used for random priming probe synthesis and subsequent hybridization in non-radioactive Du Pont's Renaissance™ kit according to the manufacturer (Du Pont NEN, Boston, Mass.). A strongly hybridizing plaque (designated psr1—1) was purified and its bacteriophage DNA isolated. The *A. thaliana* insert of the phage was subjected to dideoxy nucleotide sequencing of both strands after in vivo excision of Bluescript plasmid.

FIG. 5 shows the cDNA sequence of *B. nigra* psrPK, aligned with the cDNA sequence of the corresponding protein kinase from *Arabidopsis thaliana*.

Example 10
Genomic Clone Isolation

A genomic library of *A. thaliana* (Var. Colombia) in EMBL3 is screened at high stringency with a probe consisting of the unique 3' sequence of the *A. thaliana* psrPK cDNA insert. This insert is used for random priming probe synthesis and subsequent hybridization in non-radioactive Du Pont Renaissance™ kit according to the manufacturer (DuPont NEN, Boston). Positive clones are then rescreened until homogenous and subjected to Southern blot analysis using the same probe as above. Inserts from positive clones are excised and digested with appropriate restriction enzymes and subcloned into plasmids. The inserts are then sequenced by dideoxy nucleotide sequencing of both strands.

Example 11
Plant Transformation with psrPK Constructs

*Arabidopsis thaliana* was transformed in planta with eight different constructs employing constitutive and tissue-specific promoters attached to sense and antisense nucleic acids of the entire and partial sequences of psrPK from A. thaliana. See FIGS. 12A–12D.

In these constructs, the GUS gene present in the pBI121 vector (CLONTECH, Palo Alto, Calif., www.clontech.com) was replaced by the psrPK gene in either a sense (psr1) (FIG. 12A) or antisense (α-psr1) (FIG. 12B) direction to produce a sense or antisense construct under the control of a constitutive (CMV-35S) promoter. The CMV-35S promoter (cauliflower mosaic virus 35S promoter) of pBI121 is fused upstream of GUS gene. The GUS gene was removed from this vector by SmaI and EcoRI digestion. A cDNA encoding psrPK was cloned in pZL1 vector (isolated from Arapidopsis Resource Center cDNA library). This clone was digested by SmaI and BamHI enzymes. The BamHI site was subsequently filled in by Klenow fragment of DNA polymerase I. The resultant vector and psrPK gene were subjected to blunt-end ligation. As a result, both sense and antisense construct of psrPK genes under the control of CMV-35S promoter were obtained.

Competent *E. coli* DH 5-αwas transformed by the ligation products and plated on LB/kan. The growing colonies were picked and mini-prepped. Digestion with SalI and EcoRI enzymes distinguished the sense and antisense constructs by appearance of 1.6 Kb and 0.3 Kb fragments, respectively.

Figure 12A:
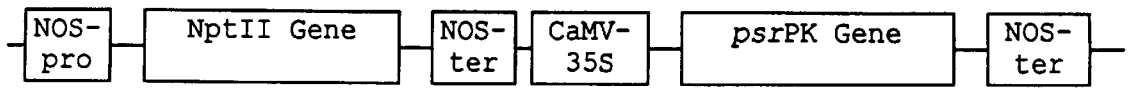
FIGS. 12A –12D depict schematic representations of sense and antisense psrPK constructs in which a constitutive (CMV-35S) or a seed-specific (Arabin-pro) promoter is fused with the sense (psr1) or antisense (α-psr1) psrPK genes.
Figure 12B:
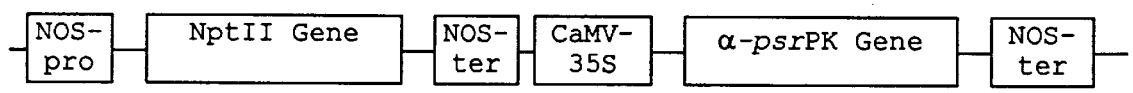
Figure 12C:
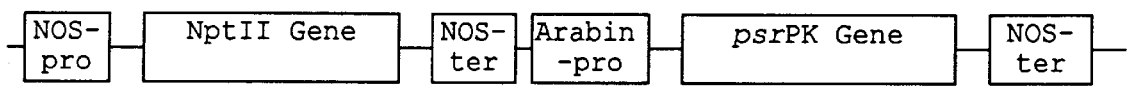
Figure 12D:
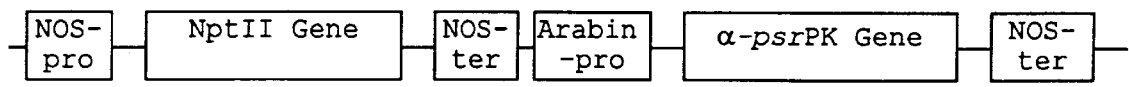
Figure 13:
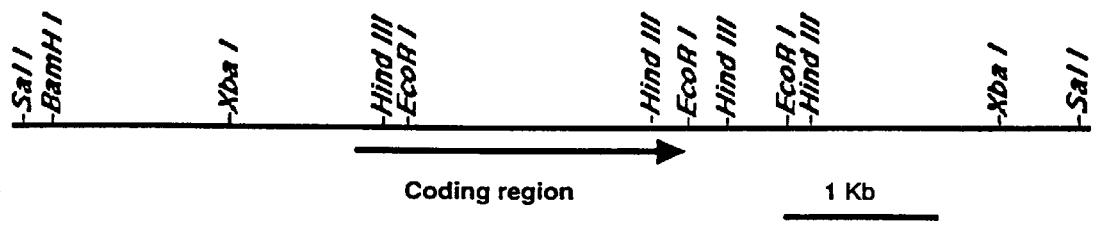
FIG. 13 is a map of the Arabidopsis thaliana clone (determined by Southern blotting of the restriction enzyme-digested DNA probed with the B. nigra psr3.1 CDNA) with the location of the psr3.2 indicated by an arrow.

Constructs depicted in FIGS. 12C and 12D were produced in a similar manner except that the promoterless pBI101 vector was used and an Arabin promoter (Arabin-pro) was inserted as a HindIII-SalI fragment fused upstream of the GUS gene in the pBI101vector. The GUS gene present in the promoterless pBI101 vector (CLONTECH, Palo Alto, Calif., www.clontech.com) was then replaced by the psrPK gene in either a sense (psr1) (FIG. 12C) or antisense (α-psr1) (FIG. 12D) direction to produce a sense or antisense construct under the control of a seed-specific (Arabin) promoter.

The in planta transformation protocol is described by Katavic et al. (1994). Briefly, *Agrobacterium tumefaciens* strain GV3101 bearing the helper nopaline plasmid MP90 and a binary vector containing the psrPK gene construct and a plant selectable marker was grown overnight. Wound sites of excised primary and secondary inflorescence shoots were exposed to cultures of the transformed Agrobacterium cells three times to inoculate the plant tissues.

The treated plants are grown to maturity, and the seeds are harvested and screened for transformants on selective medium. Confirmation of transformation is made by determining if the plants contain the transferred genes through Southern blots or polymerase chain reaction techniques using the psrPK and associated sequences.

Example 12
Bacterial Expression of psrPK and Determination of Protein Kinase Activity The psrPK protein was expressed in the *E. coli* expression vector pGEX (Promega). The insert was amplified out of the Bluescript plasmid containing the Arabidopsis psrPK such that a fragment was produced which contained the translational start and which stopped one codon short of the stop codon (i.e. excluding the stop codon). This fragment was cloned into a modified PGEX plasmid containing six extra codons for histidine at the 3' end of the inserted psrPK cDNA. The protein was then expressed in the bacteria and the psrPK protein was purified from crude extract using columns which exploit the affinity properties of the added histidine residues.

Protein kinase activity was determined by three different experiments using the purified psrPK protein. Manser, et al. (1994); Manser, et al., (1992); Manser, et al., (1995).

The first two experiments involve activity determinations on proteins obtained from plants grown in minus phosphate. Between 1–5 g of plant tissue was homogenized in a buffer containing 15 mM Hepes/KOH pH 7.6, 40 mM KCl, 5mM $MgCl_2$, 1 mM dithiothreitol (DTT), 0.1 mM phenylmethyl-sulfonyl fluoride (PMSF) (Sigma). The homogenate was kept on ice for 30 min. before centrifuging at 13000 xg for 15 min, twice. The protein concentration was determined by using Bio-Rad Protein Assay dye Reagent Concentrate as described by the manufacturer (Bio-Rad Lab., Richmond, Calif.). Fifty µg of each protein extract was loaded on to a denaturing SDS-PAGE or a native gel (Lammeli, 1970). For the SDS-PAGE, the final concentration of acrylamide monomer concentration in the 0.75 mm min gel (Bio-Rad) was 4k for the staking gel and 10% for the separating gel. The SDS-PAGE was run at 200V at room temperature and stained with Coomassie R-250 (Sigma). SDS was eliminated form the native gel composition in which the final concentration of acrylamide monomers was 3% for the stacking gel and 7% for the separating gel. The gel was run at 4° C. at 200V for 1 hr prior to loading samples and then run at 200V for 45 min. at 4° C.

The separated proteins were blotted onto Immobilon P PVDF membrane (Millipore, Mississallga, Ontario) and, in the case of the SDS denaturing samples, the blots were exposed to denaturing steps of 6M Guanidine Hcl in MES buffer, diluted 50% with MES buffer, five cycles, followed by a renaturing step of PBS buffer for 3 hours. These were then exposed to 25 mM MES, pH 6.5 buffered solution containing either purified protein and 25 $\mu$Ci $\gamma^{32}$P-ATP alone or 25 $\mu$Ci $\gamma^{32}$P-ATP for 5 min. at 22° C., then 10 min. at 4° C. The blots were then washed, dried, and exposed to X-ray film for detection purposes.

For native gel separation, the blots were immediately exposed to 25 mM MES, pH 6.5 buffered solution containing either purified protein and 25 $\mu$Ci $\gamma^{32}$P-ATP or 25 $\mu$Ci $\gamma^{32}$P-ATP alone for 5 min. at 220° C., then 10 min. at 4° C. These blots were also washed, dried and exposed to X-ray film for detection purposes.

The third activity experiment used casein or histones as artificial substrates for psrPK (Uesono, et al., (1992)). The psrPK protein expressed and purified from bacteria was dialyzed into 20 mM Tris HCl (pH 8.0), 10 mM $MgCl_2$, and 1 mM $\beta$-mercaptoethanol. An equal volume of this mixture was added to 20 $\mu$M ATP, 2 $\mu$M/ml dephosphorylated casein (or histone) and 25 $\mu$Ci $\gamma^{32}$P-ATP. The sample was run on an SDS-Page gel as described above and the gel dried and exposed to X-ray film for detection purposes. The psrPK protein phosphorylated both casein and histone.

Example 13
Plant Culture for psr $\beta$-Glucosidase Expression Analysis Under Other Stresses

*Arabidopsis thaliana* (var. Columbia) seed were germinated and grown essentially as described in Example 8. The concentration of $P_i$ was kept at 5 mM when investigating responses to other environmental stresses. For the high salt treatment, sterilized NaCl solution was added to a final concentration of 100 mM, a sublethal concentration (Saleki, et al., (1993). For media with no nitrogen, $KNO_3$ and $NH_4NO_3$ were replaced by an equal molarity of KCl. For medium lacking sulphur, $MgSO_4$ was replaced by an equal molarity of $MgCl_2$. Heat shock was performed by incubating 14 day-old plants at 390° C. for 2 hours. Anaerobic conditions were created by blowing argon gas into the flasks containing 13 day-old plants through sterilized tubes plugged with cotton for 24 hours. In all cases, the culture medium was removed and replaced with fresh medium every 4 days to ensure that there was no depletion of supplied nutrients. Treated plants were harvested after 14 days except for plants grown without nitrogen that were harvested on day 11 due to onset of severe deprivation symptoms, and plants starved for $P_i$ for 14 days and resupplied with 5 mM $P_i$ that were harvested after a further 1 or 3 days. Only $P_i$ deprivation caused significant increases in MRNA levels for $\beta$-glucosidase.

Example 14
Southern Blots and Genomic Library Screening

Genomic DNA was extracted from *A. thaliana* plant material in a CTAB extraction buffer according to Saghai-Maroof and colleagues 38]. About 10 $\mu$g of genomic DNA was digested with either BamHl, EcoRI, Sall, or BamHI/Sall restriction enzymes overnight at 370° C. After separating the digestion products on a 0.8% agarose gel, DNA fragments were transferred on to Nytran-Plus membrane as described by the manufacturer (Schleicher and Schuell, Guelph, Canada). The Brassica nigra psr3.1 CDNA insert (Malboobi and Lefebvre, (1995)) was used for random priming probe synthesis and subsequent hybridization using the non-radioactive DuPont Renaissance™ system according to the manufacturer (Du Pont NEN, Boston, Mass.).

A genomic library of A. thaliana ecotype Columbia cloned into EMBL3 was provided by Kenton Ko, Queen's University, Kingston, Canada. About 200,000 plaque forming units (pfu) were screened with probe derived from he *B. nigra* psr3.1 cDNA clone at high stringency conditions (Malboobi and Lefebvre, (1995)). Positive clones were carried through secondary and tertiary screening. Probes derived from the isolated genome DNA inserts were used in Southern blotting to determine which genomic clones corresponded to the *B. nigra* psr3.1. A genomic clone with a similar blotting pattern to that of *B. nigra* psr3.1 cDNA clone was chosen for restriction enzyme site mapping and subcloning by standard methods (Sambrook, et al., (1989)).

Example 15
RNA Isolation and Northern Blots

Total RNA was extracted from plant tissues according to Chirgwin and colleagues (Chirgwin, et al., (1979). Twenty five $\mu$g of each RNA extract was loaded or to a 1% agarose/formaldehyde gel (Sambrook, et al., 1989). Northern blotting and laser densitometric scanning of autoradiograms were carried out as previously described (Malboobi and Lefebvre, (1995)).

Example 16
Sequence Determination and Computer Analysis

The restriction enzyme DNA fragments of EcoRI, and EcoRI/SalI digestions of the psr3 genomic clone were prepared and inserted into the Bluescript KS-vector (Stratagene, La Jolla, Calif.) and used to transform competent *E. coli* strait DH5-$\alpha$(GIBCO BRL, Burlington, Canada) through standard cloning techniques (Sambrook, et al., 1989). Plasmid DNA was prepared with the Wizard™ Megapreps DNA Purification System (Promega, Madison, Wiss.). Both strands of the inserts were sequenced by dideoxy nucleotide method in a Sequenase Version 2 Kit (United States Biochemical Corp., Cleveland, Ohio). Homology searches of databases were conducted using the BLASTX program (Gish and State (1993) against DNA and protein sequences. Assembling and editing of the coding sequence and analysis of DNA and predicted protein sequences was performed using the appropriate prograrcks of LASERGENE software or Macintosh (DNASTAR, Madison, Wis.). Similar sequencing and homology searches were performed for all cDNA clones of psr genes.

Example 17
Primer Extension Analysis

Transcriptional start sites for $\beta$-glucosidase were determined by primer extension analysis. The oligonucleotide, AGCAAAAGCGCCCATGAGAGGAA, was labelled with T4 poly-nucleotide kinase (Promega, Madison, Wis.) in the presence of [$\gamma$-$^{32}$P] -DATP as described (Sambrook, et al., (1989)). Labelled oligonucleotides were purified using the MERMAID system (Bio/Can Scientific, Mississauga, Canada) and annealed to RNA extracted from $P_i$-.starved roots for primer extension by AMV reverse transcriptase (Pharmacia, Baie D'Urfé, Canada) as described in Ausubel, et al., (1995).

Example 18
Protein Extraction and gel Electrophoresis for $\beta$-Glucosidase Approximately ten mg fresh wt of root tissue was homogenized in 500 $\mu$l of a buffer containing 15 mM HEPES/KOH pH7.6, 40 mM KCl, 5 mM $MgCl_2$ 1 mM dithiothreitol (DTT), O. 1 mM phenylmethylsulfonyl fluoride (PMSF) (Sigma, St. Louis, Mo.). The homogenate was kept on ice for 30 min. before spinning at 13000 g for 15 min. The supernatant was removed and centrifuged for a further 15 min. The protein concentration of this final supernatant was determined using Bio-Rad Protein Assay Dye Reagent Concentrate as described by manufacturer (Bio-Rad, Richmond, Calif.). Fifty μg of total protein was run in each lane in either denaturing SDS-PAGE or native PAGE gels (Laemeli, (1970)). For the SDS-PAGE, the final concentration of acrylamide monomer in the 0.75 mm thick mini-gel (Bio-Rad) was 4% and 10% in the stacking and separating gels, respectively. The gel was run at 200V at room temperature and stained with Coomassie R-250 (Sigma). For the native gel, SDS was eliminated from all reagents and the final concentrations of acrylamide monomer were 3k and 7% for the stacking and separating gels, respectively. The native gel was prerun at 40° C. and 100 V for 30 min prior to sample loading and then run at 200V for 3 h at 40° C. To detect β-glucosidase activity, the native gel was equilibrated in a 100 mM sodium acetate, pH 6.5 (Sigma) buffer containing 20 mM $CaCl_2$ for 15 min. This was followed by incubation for 3 hours in the same solution plus 0.02% (w/v) Fast Garnet GBC salt (Sigma) and 0.04% (w/v) β-naphthyl β-D-glucopyranoside (Sigma) at room temperature.

References

Anderberg, R. J. and Walker-Simmons, M. K., *Proc. Natl. Acad. Sci. USA* 89: 10183–10187 (1992).
Aoyagi, et al., *Mol. Gen. Genet.* 213: 179–185.
Ashihara, H., et al., *Ann. Bot.* 61: 225–232 (1988).
Ausubel, F. M. et al., eds. *Current Protocols in Molecular Biology,* Greene Publishing Associates and John Wiley & Sons Inc., (1993).
Balou, L. M., and Fisher, E. H., In Boyer, et al. eds. *The Enzymes,* Vol.17, pp. 311–361, Academic Press, NY (1986).
Bieleski, R. L., *Annu. Rev. Plant. Physiol.* 24: 225–252 (1973).
Brisson, et al., *Nature* 310: 511–514 (1984).
Broglie, et al., *Science,* 224: 838–43 (1984).
Chappell, J. and Hahlbrock, K., Nature 311: 76–78 (1984).
Chirgwin, J. M., et al., Biochemistry 18: 5294–5299 (1979).
Cordes, et al., *Plant Cell* 1: 1025–1034 (1989).
Coruzzi, et al., EMBO J. 3: 1671–1679 (1984).
de Feyter, R., et al., *Mol. Gen. Genet.* 250: 329–338 (1996).
de Pater, et al., *Plant Cell* 5: 877–866 (1993).
Delhaize, E., and Randall, P. J., *Plant Physiol.* 107: 207–213 (1995).
Duff, S. M. G., et al., *Plant Physiol.* 90: 734–741 (1989a).
Duff, S. M. G., et al., *Plant Physiol.* 90: 1275–1278 (1989b).
Duff, S. M. G., et al., *Proc. Natl. Acad. Sci. USA* 88: 9538–9542 (1991).
Duff, S. M. G., et al., Physiol. Plant 90: 791–800 (1994).
Edwards, et al., *Proc. Natl. Acad. Sci. USA,* 87: 3459–3463 (1990).
Fife, C.A., et al., *Can. J. Bot.* 68: 1840–1847 (1990).
Freeling, M., et al.,*Ann. Rev. Genetics,* 19: 297–323 (1985).
Fritsch, et al., *Plant J.* 7: 503–512 1995).
Gellatly, K.S., et al., *Plant Physiol.* 106: 223–232 (1994).
Gelvin, S., et al., *Plant Molecular Biology Manual,* Kluwer Academic Publishers, Amsterdam (1992).
Gish, W., and State, D. J., *Nature Genet.* 3:266–272 (1993).
Glund, K., and Goldstein, A. H., In Verma, ed., *Control of Plant Gene Expression,* CRC Press, Boca Raton, Fla., pp. 311–323 (1993).
Gogarten, J. P., et al., *The Plant Cell* 4:851–864 (1992).
Goldstein, A. H., et al., *Plant Physiol.* 91: 175–182 (1989).
Goldstein, A. H., In Wary, ed., *Inducible Plant Proteins,* Cambridge University Press, NY, pp. 25–44 (1992).
Grierson and Corey, *Plant Molecular Biology,* 2d Ed., Blackie, London, Ch. 7–9 (1988).
Gurley, et al., *Mol. Cell. Biol.* 6: 559–565 (1986).
Harlow, E., and Lane, D.,*Antibodies: A Laboratory Manual,* Cold Spring Harbor Laboratory, Cold Spring Harbor, N.Y. (1988).
Hattori, et al. Plant J. 7: 913–925 (1995).
Hawkesford, M. J., and Belcher, A. R., Planta 185: 323–329 (1991).
Heinrich, J. C., et al., Antisense Res. Dev. 5: 155–160 (1995).
Hoefnagel, M. H. N., et al., *Physiol. Plant* 87: 297–304 (1993).
Innis, M. A., et al., *PCR Protocols:* A Guide to Methods and Applications, Academic Press, Inc., San Diego, Calif. (1990).
Katavic, V., et al., *Mol. Gen. Genet.* 245: 363–370 (1994).
Kieber, J. J., et al., *Cell* 72: 427–441 (1993).
Konat, G., et al., *Technique* 3: 64–68 (1991).
Kosugi, et al., Plant J. 7: 877–886 (1995).
Laemmli, U. K., *Nature* 227: 680–685 (1970).
Lee, R. B., et al., *J. Exp. Bot.* 41: 1063–1078 (1990).
Lefebvre, D. D. and Glass, A.D.M., *Physiologia Plantarum* 54: 199–206 (1982).
Lefebvre, D. D., et al., Plant Physiol. 93: 504–511 (1990).
Loffler, A., et al., *Plant Physiol.* 98: 1472–1478 (1992).
Malboobi, M. A., and Lefebvre, D. D., *Plant Mol. Biol.* 28: 859–870 (1995).
Maniatis, T., et al., *Molecular Cloning: A Laboratory Manual,* Cold Spring Harbor Laboratory, Cold Spring Harbor, N.Y. (1982).
Manser, E., et al., *Nature* 367: 40–46 (1994).
Manser, E., et al.,*J. Biol. Chem.* 267: 16025–16028 (1992).
Manser, E., et al., *Methods in Enzymol.* 256: 215–227, Ch. 24, (1995).
Marcotte Jr., et al., *Plant Cell* 1: 969–976 (1989).
Martin, et al. *Plant J.* 4: 367–377 (1989).
Meyer, P. and Saedler, H., *Annu. Rev. Plant Physiol. Plant Mol. Biol.* 47: 23–48 (1996).
Mimura, T., et al., *Planta* 180: 136–146 (1990).
Muller-Rober, et al., *Plant Cell* 6: 601–612 (1994).
Murashige, T., and Skoog, F., *Physiol. Plant* 15: 473–497 (1962).
Murray and Crockett, In, Antisense RNA and DNA, Murray, ed. pp. 1–49 (1992).
Nagano, M., and Ashihara, H., *Plant Cell Physiol.* 34: 1219–1228 (1993).
Nagao, R. T., et al., *Oxford Surveys of Plant Molecular and Cell Biology,* Miflin, B. J., Ed., 3: 384–438, Oxford University Press, Oxford (1986).
Nurnberger, T., et al., *Plant Physiol.* 92: 970–976 (1990).
O'Reilly, D. R., et al., *Baculovirus Expression Vectors. A Laboratory Manual,* W. H. Freeman and Co., NY (1992).
Park, Y. S., et al., *Plant Mol. Biol.* 22: 615–624 (1993).
Poirier, Y., et al., *Plant Physiol.* 97: 1087–1093 (1991).
Rao, I. M., et al., Plant Physiol. 92: 29–36 (1990).
Rebeille, F., et al. *Arch. Biochem. Biophys.* 225: 143–148 (1983).
Rodrigues-Pousada, et al., *Plant Cell* 5: 897–911 (1993).
Rychter, A. M., and Mikulska, M., *Physiol. Plant* 79: 663–667 (1990).
Rychter, A. M., et al., Plant 84: 80–86 (1992).
Sachay, J. E., et al., *Plant Soil* 132: 85–90 (1991).
Sadka, A., et al., *Plant Cell* 6: 737–739 (1994).
Sagaya, et al., Plant Cell Physiol., 3: 649–653 (1989).
Saiki, R. K., et al., Science 230: 1350–1354 (1985).
Saleki, R., et al., Plant Physiol. 101: 839–845 (1993).
Salisbury, F. B. and Ross, C. W., *Plant Physiology* (3rd ed.), Wadsworth Publishing Co., Belmont, Calif., pp. 96–113 (1985).

Sambrook J., et al., *Molecular Cloning: A Laboratory Manual* (2nd Ed.), Cold Spring Harbor Laboratory, Cold Spring Harbor, N.Y. (1989).
Sanford, J. C., et al., U.S. Pat. No. 5,100,792 (1992)
Sanger, F., *Science* 214: 1205–1210 (1981).
Scopes, R., *Protein Purification*, Springer-Verlag, New York (1982).
Shotkoski, F. A. and Fallon, A. M., *Am. J. Trop. Med. Hyg.* 50: 433–439 (1994).
Somssich, I. E. et al., *Plant Mol. Biol.* 12: 227–234 (1989).
Takamatsu, et al., *EMBO J.* 6: 307–311 (1987).
Tantikanjana, T., et al., *Plant Cell* 5: 657–666 (1993).
Theodorou, M. E., et al., *J. Biol. Chem.* 267: 21901–21905 (1992).
Theodorou, M. E., and Plaxton, W. C., *Plant Physiol.* 101: 339–344 (1993).
Thomas, T. L., *Plant Cell* 5: 1401–1410 (1993).
Tu, S. I., et al., *Plant Physiol.* 93: 778–784 (1990).
Uesono, Y., et al., *Mol. Gen. Genet.* 231: 426–432 (1992).
Unger, et al., *Plant Cell* 5: 831–841 (1993).
Usuda, H., and Shimogawara, K., *Plant Cell Physiol.* 34: 767–770 (1993).
Vorst, et al., *Plant J.* 4: 933–945 (1993)
Walker, V. K., *Advances in Cell Culture* 7: 87–124 (1989).
Wang, et al. *Plant Mol. Biol.* 28: 605–634 (1995).
Wang and cutler, *Plant Mol. Biol.* 28: 619–617 (1995).
Weissbach and Weissbach, *Methods for Plant Molecular Biology*, Academic Press, New York, Section VIII, pp. 421–463 (1988).
Weterings, et al., *Plant J.* 8: 55–63 (1995).
White, T. C., et al., *Plant Physiol.*, 106:917.
Willmitzer, L., and Wagner, K. G., *Exp. Cell Res.* 135: 64–77 (1981).
Wissenbach, et al. *Plant J.* 4: 412–422 (1993).
Yang, et al. *Proc. Natl. Acad. Sci., USA,* 87: 4144–4148 (1990).
Zhang, R. and Walker, J. C., *Plant Mol. Biol.* 21: 1171–1174 (1993).

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. Isolated DNA encoding a protein kinase of a plant in which transcription of the DNA is induced by phosphate deficiency in the plant.

2. Isolated DNA encoding a protein kinase of a plant in which transcription of the DNA is induced by phosphate deficiency in said plant according to claim 1, which DNA comprises:
   (a) SEQ ID NO:1, SEQ ID NO:3, or a nucleic acid sequence which encodes SEQ ID NO:48;
   (b) a nucleic acid sequence which is hybridizable to a nucleic acid sequence which encodes SEQ ID NO:48, in a hybridization procedure with 50% formamide, 5× SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with a wash at 42° C. in 0.2× SSC and 0.1% SDS; or
   (c) a nucleic acid which is complementary to any of the nucleic acid sequences of (a) or (b).

3. Isolated DNA encoding a protein kinase of plant in which transcription of the DNA is induced by phosphate deficiency in said plant, the DNA comprising nucleotide residues 1041 to 1106 of SEQ ID NO:1.

4. Isolated nucleic acid encoding a protein kinase of a plant in which transcription of the nucleic acid is induced by phosphate deficiency in said plant, the nucleic acid comprising nucleotide residues 1065 to 1088 of SEQ ID NO: 1, in a hybridization procedure with 50% formamide, 5× SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with a wash at 42° C. in 0.2× SSC and 0.1% SDS.

5. An isolated nucleic acid encoding a protein kinase of a plant in which transcription of the nucleic acid is induced by phosphate deficiency in said plant, the isolated nucleic acid encoding an amino acid sequence comprising 40 consecutive amino acids of SEQ ID NO:2 or comprising 20 consecutive amino acids of amino acid residues 318 to 339 of SEQ ID NO:2.

6. The isolated DNA encoding a protein kinase of a plant in which transcription of the DNA is induced by phosphate deficiency in said plant according to claim 1, which DNA is isolated from Brassica sp. or Arabidopsis sp.

7. The isolated DNA encoding a protein kinase of a plant in which transcription of the DNA is induced by phosphate deficiency in said plant according to claim 1, which DNA is recombinant or synthetic DNA.

8. Isolated DNA encoding a protein kinase of a plant in which transcription of the DNA is induced by phosphate deficiency in said plant, which DNA comprises nucleotides 1065 to 1088 of SEQ ID NO:1.

9. Isolated DNA encoding a protein kinase of a plant in which transcription of the DNA is induced by phosphate in said plant, which DNA comprises a nucleic acid sequence which is complementary or which hybridizes to nucleotides 1065 to 1088 of SEQ ID NO:1 in a hybridization procedure with 50% formamide, 5× SSC, 50 mM sodium phosphate (pH 6.8), 0.1% sodium pyrophosphate, 5× Denhat's solution, sonicated salmon sperm DNA (50 µg/ml), 0.1% SDS, and 10% dextran sulfate at 42° C., with a wash 42° C. in 0.2× SSC and 0.1% SDS.

10. A probe or primer comprising 16 or more nucleotides which hybridizes to nucleotides 1041–1106 of SEQ ID NO:1 in a hybridization procedure with 50% formamide, 5× SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with a wash at 42° C. in 0.2× SSC and 0.1% SDS.

11. An isolated nucleic acid encoding a protein kinase of a plant in which transcription of nucleic acid is induced by phosphate deficiency in said plant, the nucleic acid comprising 16 or more contiguous nucleotides of a DNA consisting of nucleotides 1065 to 1088 of SEQ ID NO:1.

12. An isolated nucleic acid encoding a protein kinase of a plant in which transcription of the nucleic acid is induced by phosphate deficiency in said plant, the nucleic comprising 20 or more contiguous nucleotides of a DNA consisting of nucleotides 1065 to 1088 of SEQ ID NO:1.

13. An isolated nucleic acid encoding a protein kinase of plant in which transcription of the nucleic acid is induced by phosphate deficiency in said plant, wherein the nucleic acid hybridizes to a nucleic acid comprising 16 or more contiguous nucleotides of a DNA consisting of nucleotides 1065 to 1088 of SEQ ID NO:1 in a hybridization procedure with 50% formamide, 5× SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with a wash at 42° C. in 0.2× SSC and 0.1% SDS.

14. An isolated nucleic acid encoding a protein kinase of a plant in which transcription of the nucleic acid is induced by phosphate deficiency in said plant, wherein the nucleic acid hybridizes to a nucleic acid comprising 20 or more contiguous nucleotides of a DNA consisting of nucleotides 1065 to 1088 of SEQ ID NO:1 in a hybridization procedure with 50% formamide, 5× SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C. with a wash at 42° C. in 0.2× SSC and 0.1% SDS.

15. A transgenic cell of a photosynthetic organism containing:

a) the DNA of claim 2;

b) DNA complementary to the DNA of a); or c) either (a) or (b), and one or more other exogenous nucleic acids.

16. A cell according to claim 15 which is a root cell.

17. A cell according to claim 15 which is the cell of a seed.

18. A cell according to claim 15 which is a photosynthetic cell.

19. Isolated DNA encoding a protein kinase of a plant in which transcription of the DNA is induced by phosphate deficiency in said plant, which DNA comprises a nucleic acid encoding SEQ ID NO:48.

20. Isolated nucleic acid encoding a protein kinase of a plant in which transcription of the nucleic acid is induced by phosphate deficiency in said plant, which nucleic acid hybridizes to a nucleic acid which encodes SEQ ID NO:48 in a hybridization procedure with 50% formamide, 5× SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with a wash at 42° C. in 0.2× SSC and 0.1% SDS.

21. A probe or primer comprising 16 or more nucleotides which hybridizes to a nucleic acid encoding a protein kinase of a plant in which transcription of the nucleic acid is induced by phosphate deficiency in said plant, wherein the probe or primer hybridizes to a nucleic acid encoding SEQ ID NO:48 in a hybridization procedure with 50% formamide, 5× SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with a wash at 42° C. in 0.2× SSC and 0.1% SDS.

22. An isolated nucleic acid encoding a protein kinase of a plant in which transcription of the nucleic acid is induced by phosphate deficiency in said plant, the nucleic acid comprising 16 or more contiguous nucleotides of DNA which encodes SEQ ID NO:48.

23. An isolated nucleic acid encoding a protein kinase of a plant in which transcription of the nucleic acid is induced by phosphate deficiency in said plant, the nucleic acid comprising 20 or more contiguous nucleotides of a DNA which encodes SEQ ID NO:48.

24. Isolated nucleic acid encoding a protein kinase of a plant in which transcription of the nucleic acid is induced by phosphate deficiency in said plant, wherein the nucleic acid hybridizes to a nucleic acid comprising 16 or more contiguous nucleotides of a DNA which encodes SEQ ID NO:48 in a hybridization procedure with 50% formamide, 5× SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with a wash at 42° C. in 0.2× SSC and 0.1% SDS.

25. Isolated nucleic acid encoding a protein kinase of a plant in which transcription of the nucleic acid is induced by phosphate deficiency in said plant, wherein the nucleic acid hybridizes to a nucleic acid comprising 20 or more contiguous nucleotides of a DNA which encodes SEQ ID NO:48 in a hybridization procedure with 50% formamide, 5× SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with a wash at 42° C. in 0.2× SSC and 0.1% SDS.

* * * * *

UNITED STATES PATENT AND TRADEMARK OFFICE
CERTIFICATE OF CORRECTION

PATENT NO. : 6,096,545
DATED : August 1, 2000
INVENTOR(S) : Daniel D. Lefebvre and Mohammed A. Malboobi It is certified that error appears in the above-identified patent and that said Letters Patent is hereby corrected as shown below:

Column 4,
Lines 24 and 26, "par" should be -- psr --;

Column 7,
Line 10, "CDNA" should be -- cDNA --;

Column 8,
Lines 16 and 24, "CDNA" should be -- cDNA --;

Column 9,
Line 58, "80t" should be -- 80% --;

Column 10,
Line 2, "nucleic sequence encoding YLDANCE" should be -- nucleic acid sequence encoding YLDANDEE --;

Column 21,
Lines 20-21, "calorimetric" should be -- colorimetric --;
Line 39, "methods 30 wherein" should be -- methods wherein --;

Column 23,
Line 33, "a-subunit" should be -- α-subunit --;

Column 27,
Line 51, "CDNA" should be -- cDNA --; (two occurrences)

Column 28,
Line 56, "1i" should be -- 1% --;

UNITED STATES PATENT AND TRADEMARK OFFICE
CERTIFICATE OF CORRECTION

PATENT NO.    : 6,096,545
DATED         : August 1, 2000
INVENTOR(S)   : Daniel D. Lefebvre and Mohammed A. Malboobi It is certified that error appears in the above-identified patent and that said Letters Patent is hereby corrected as shown below:

<u>Column 32,</u>
Line 32, "PGEX" should be -- pGEX --;
Line 54, "4k" should be -- 4% --;

<u>Column 33,</u>
Line 10, "200°C" should be -- 22°C --;
Line 36, "390°C" should be -- 39°C --;
Line 48, "MRNA" should be -- mRNA --;
Line 56, "370°C" should be -- 37°C --;
Line 60, "CDNA" should be -- cDNA --;

<u>Column 34,</u>
Line 49, "DATP" should be -- dATP --;

<u>Column 35,</u>
Line 11, "3k" should be -- 3% --;

<u>Column 104,</u>
Line 44, "kinase of plant" should be -- kinase of a plant --;

<u>Column 108,</u>
Line 32, "phosphate in" should be -- phosphate deficiency in --;
Line 37, "Denhat's" should be -- Denhardt's --;
Line 39, "wash" should be -- wash at --;
Line 48, "of nucleic" should be -- of the nucleic --;
Line 54, "nucleic comprising" should be -- nucleic acid comprising --;
Line 58, "plant" should be -- a plant --;

UNITED STATES PATENT AND TRADEMARK OFFICE
CERTIFICATE OF CORRECTION

PATENT NO.    : 6,096,545
DATED         : August 1, 2000
INVENTOR(S)   : Daniel D. Lefebvre and Mohammed A. Malboobi It is certified that error appears in the above-identified patent and that said Letters Patent is hereby corrected as shown below:

<u>Column 110,</u>
Line 12, "of DNA" should be -- of a DNA --;

Signed and Sealed this

Twenty-first Day of January, 2003

JAMES E. ROGAN
*Director of the United States Patent and Trademark Office*